(12) United States Patent  
Lee et al.

(10) Patent No.: US 9,405,884 B2  
(45) Date of Patent: Aug. 2, 2016

(54) METHODS AND SYSTEMS FOR THE ANALYSIS OF PROTEIN SAMPLES

(75) Inventors: David H. Lee, Arlington, MA (US); Anton V. Manuilov, Burlington, MA (US)

(73) Assignee: AbbVie Inc., North Chicago, IL (US)

(*) Notice: Subject to any disclaimer, the term of this patent is extended or adjusted under 35 U.S.C. 154(b) by 1211 days.

(21) Appl. No.: 13/332,077

(22) Filed: Dec. 20, 2011

(65) Prior Publication Data

US 2012/0245857 A1    Sep. 27, 2012

Related U.S. Application Data

(63) Continuation-in-part of application No. 13/161,907, filed on Jun. 16, 2011.

(60) Provisional application No. 61/355,269, filed on Jun. 16, 2010, provisional application No. 61/466,912, filed on Mar. 23, 2011.

(51) Int. Cl.
*G06F 19/00* (2011.01)
*G01N 33/68* (2006.01)
*G01N 30/72* (2006.01)
*G06F 19/24* (2011.01)

(52) U.S. Cl.
CPC .......... *G06F 19/00* (2013.01); *G01N 33/6848* (2013.01); *G01N 30/72* (2013.01); *G01N 33/6803* (2013.01); *G06F 19/24* (2013.01); *Y10T 436/24* (2015.01)

(58) Field of Classification Search
CPC ................................ G01N 30/72; G06F 19/00

USPC ............................................ 702/22; 436/173  
See application file for complete search history.

(56) References Cited

U.S. PATENT DOCUMENTS

| | | |
|---|---|---|
| RE30,985 E | 6/1982 | Cartaya |
| 4,399,216 A | 8/1983 | Axel et al. |
| 4,510,245 A | 4/1985 | Cousens et al. |
| 4,560,655 A | 12/1985 | Baker |
| 4,634,665 A | 1/1987 | Axel et al. |
| 4,657,866 A | 4/1987 | Kumar |
| 4,767,704 A | 8/1988 | Cleveland et al. |

(Continued)

FOREIGN PATENT DOCUMENTS

| | | |
|---|---|---|
| EP | 1 686 372 A1 | 8/2002 |
| EP | 1 420 254 A2 | 5/2004 |

(Continued)

OTHER PUBLICATIONS

Tamar Geiger, Juergen Cox, Pawel Ostasiewicz, Jacek R Wisniewski & Matthias Mann "Super-SILAC mix for quantitative proteomics of human tumor tissue" published online Apr. 4, 2010, Nature Methods, vol. 7 No. 5 pp. 383-385 and Online Methods pp. 1-2.*

(Continued)

*Primary Examiner* — Christopher A Hixson  
*Assistant Examiner* — Emily Berkeley  
(74) *Attorney, Agent, or Firm* — Lathrop & Gage LLP; Andrew T. Wilkins; Michael A. Mattoni

(57) ABSTRACT

The present invention relates to methods for analyzing protein samples, e.g., monoclonal antibodies, via the SITRS technique, as well as methods and systems that facilitate the processing of data generated by the SITRS technique.

23 Claims, 34 Drawing Sheets

(56) References Cited

U.S. PATENT DOCUMENTS

| | | |
|---|---|---|
| 4,816,397 A | 3/1989 | Boss et al. |
| 4,816,567 A | 3/1989 | Cabilly et al. |
| 4,927,762 A | 5/1990 | Darfler |
| 4,968,615 A | 11/1990 | Koszinowski et al. |
| 5,122,469 A | 6/1992 | Mather et al. |
| 5,168,062 A | 12/1992 | Stinski |
| 5,179,017 A | 1/1993 | Axel et al. |
| 5,223,409 A | 6/1993 | Ladner et al. |
| 5,225,539 A | 7/1993 | Winter |
| 5,476,996 A | 12/1995 | Wilson et al. |
| 5,530,101 A | 6/1996 | Queen et al. |
| 5,585,089 A | 12/1996 | Queen et al. |
| 5,693,762 A | 12/1997 | Queen et al. |
| 5,698,767 A | 12/1997 | Wilson et al. |
| 6,180,370 B1 | 1/2001 | Queen et al. |
| 6,914,128 B1 | 7/2005 | Salfeld et al. |
| 2006/0134723 A1 | 6/2006 | Fischer et al. |
| 2007/0154900 A1 | 7/2007 | Schneider et al. |
| 2008/0057592 A1* | 3/2008 | Oda ................. B01J 20/286 436/86 |
| 2008/0058246 A1 | 3/2008 | Bhaskaran et al. |
| 2008/0299595 A1 | 12/2008 | Wong et al. |
| 2009/0011447 A1 | 1/2009 | Banoub et al. |
| 2009/0181004 A1 | 7/2009 | Kaariainen et al. |
| 2010/0143912 A1 | 6/2010 | Wells et al. |
| 2010/0286927 A1 | 11/2010 | Horn et al. |
| 2011/0136160 A1 | 6/2011 | Sanchez et al. |
| 2011/0312010 A1 | 12/2011 | Manuilov et al. |
| 2012/0241603 A1 | 9/2012 | Scigocki |
| 2012/0264154 A1 | 10/2012 | Mann et al. |

FOREIGN PATENT DOCUMENTS

| | | |
|---|---|---|
| EP | 2 309 262 | 4/2011 |
| WO | WO 87/00195 | 1/1987 |
| WO | WO 90/03430 | 4/1990 |
| WO | WO 91/17271 | 11/1991 |
| WO | WO 92/01047 | 1/1992 |
| WO | WO 92/09690 | 6/1992 |
| WO | WO 92/15679 | 9/1992 |
| WO | WO 92/18619 | 10/1992 |
| WO | WO 92/20791 | 11/1992 |
| WO | WO 93/01288 | 1/1993 |
| WO | 2006096704 A2 | 9/2006 |

OTHER PUBLICATIONS

Tamar Geiger, Juergen Cox, Pawel Ostasiewicz, Jacek R Wisniewski & Matthias Mann "Supplementary figures and text: Super-SILAC mix for quantitative proteomics of human tumor tissue" published online Apr. 4, 2010 Nature Methods: doi: 10.1038/nmeth.1446.*
U.S. Appl. No. 13/161,907 (US 2011/0312010), Jun. 16, 2011 (Dec. 22, 2011).
Barbas, et al., "Assembly of Combinatorial Antibody Libraries on Phage Surfaces: The Gene III Site ", *PNAS*, 88(18):7978-7982 (1991).
Bird, et al. ,"Single-Chain Antigen-Binding Proteins", *Science*, 242(4877):423-426 (1988).
Gram, et al., "In Vitro Selection and Affinity Maturation of antibodies from a Naïve combinatorial Immunoglobulin Library", *PNAS*, 89(8):3576-3580 (1992).
Greiger, et al., "Use of Stable Isotope Labeling by Amino Acids in Cell Culture as A Spike-In Standard in Quantitative Proteomics", *Nature Protocols*, 6(2):147-157 (2011).
Holliger, et al., "Diabodies: Small Bivalent and Bispecific Antibody Fragments", *PNAS*, 90(14):6444-6448 (1993).
Huse, et al., "Generation of a Large Combinatorial Library of the Immunoglobulin Repertoire in Phage Lambda", *Science*, 246(4935):1275-1281 (1989).
Huston, et al., "Protein Engineering of Antibody Binding Sites: Recovery of Specific Activity in an Anti-Digoxin Single-Chain Fv Analogue Produced in *Escherichia Coli*", *PNAS*, 85(16):5879-5883 (1988).
International Search Report and Written Opinion for PCT/US2011/066003, dated Jul. 18, 2012 (corresponds to U.S. Appl. No. 13/332,077).
International Search Report for PCT/US2011/040669, dated Oct. 27, 2011 (corresponds to U.S. Appl. No. 13/161,907).
Manuilov, et al., "Comparability Analysis of Protein Therapeutics by Bottom-UP LC-MS with Stable Isotope-Tagged Reference Standards", *MABS*, 3(4):387-395 (2011).
Urlaub, et al., "Isolation of Chinese Hamster Cell Mutants Deficient in Dihydrofolate Reductase Activity", *PNAS USA*, 77(7):4216-4220 (1980).

* cited by examiner

|  | Seq Loc |
|---|---|
| SEQ ID: 1    DIQMTQSPSSMSVSVGDR | LC(1-18) |
| SEQ ID: 2  DIQMTQSPSSMSVSVGDRVTITCHSSQDINSNIGWLQQKPGK | LC(19-42) |
| SFK | LC(43-45) |
| SEQ ID: 3  GLIYHGTNLDDGVPSR | LC(46-61) |
| SEQ ID: 4  FSGSGSGTDYTLTISSLQPEDFATYYCVQYAQFPWTFGGGTK | LC(62-103) |
| SEQ ID: 5 LEIKR | LC(104-108) |
| SEQ ID: 6 TVAAPSVFIFPPSDEQLK | LC(109-126) |
| SEQ ID: 7 SGTASVVCLLNNFYPR | LC(127-142) |
| SEQ ID: 8  VQWK | LC(146-149) |
| SEQ ID: 9 VDNALQSGNSQESVTEQDSK | LC(150-169) |
| SEQ ID: 10 DSTYSLSSTLTLSK | LC(170-183) |
| SEQ ID: 11 ADYEK | LC(184-188) |
| SEQ ID: 12 HKVYACEVTHQGLSSPVTK | LC(189-207) |
| SEQ ID: 13 SFNRGEC | LC(208-214) |
| SEQ ID: 14 pEVQLQESGPGLVKPSQTLSLTCTVSGYSISSDFAWNWIR | HC(pE1-39) |
| SEQ ID: 15 QPPGK | HC(40-44) |
| SEQ ID: 16 GLEWMGYISYSGNTR | HC(45-59) |
| SEQ ID: 17 YQPSLK | HC(60-65) |
| SEQ ID: 18 SRITISR | HC(66-72) |
| SEQ ID: 19 ITISR | HC(68-72) |
| SEQ ID: 20 DTSKNQFFLK | HC(73-82) |
| SEQ ID: 21 LNSVTAADTATYYCVTAGR | HC(83-101) |
| SEQ ID: 22 GFPYWGQGTLVTSSASTK | HC(102-120) |
| SEQ ID: 23 GPSVFPLAPSSK | HC(121-132) |
| SEQ ID: 24  STSGGTAALGCLVK | HC(133-146) |
| SEQ ID: 25 DYFPEPVTVSWNSGALTSGVHTFPAVLQSSGLYSLSSVVTVPSSSLGTQTYICNVNHKPSNTK | HC(147-209) |
| VDK | HC(210-212) |
| SEQ ID: 26 KVEPK | HC(213-217) |
| SEQ ID: 27 VEPK | HC(214-217) |
| SEQ ID: 28 SCDKTHTCPPCPAPELLGGPSVFLFPPKPK | HC(218-247) |

FIG. 8

| | unlabled/labeled %ratio | | | | | | Sample | | |
|---|---|---|---|---|---|---|---|---|---|
| Sample B | std dev | Sample A | std dev | B/A | stdev | B as % A | stdev | diff |
| 111.94 | 0.80 | 109.20 | 0.69 | 1.0251 | 0.009807 | 99.86 | 0.96 | −0.1 |
| 112.45 | 0.63 | 108.93 | 0.44 | 1.0323 | 0.007109 | 100.56 | 0.69 | 0.6 |
| 109.18 | 0.95 | 106.53 | 0.47 | 1.0249 | 0.009971 | 99.84 | 0.97 | −0.2 |
| 110.36 | 0.29 | 107.96 | 0.16 | 1.0222 | 0.003072 | 99.58 | 0.30 | −0.4 |
| 103.84 | 0.24 | 101.03 | 0.23 | 1.0279 | 0.003313 | 100.13 | 0.32 | 0.1 |
| 114.87 | 0.50 | 112.98 | 0.48 | 1.0168 | 0.006159 | 99.05 | 0.60 | −1.0 |
| 109.10 | 0.54 | 106.11 | 0.31 | 1.0283 | 0.005862 | 100.17 | 0.57 | 0.2 |
| 108.96 | 0.33 | 106.37 | 0.18 | 1.0243 | 0.003551 | 99.78 | 0.35 | −0.2 |
| 111.54 | 0.26 | 109.12 | 0.41 | 1.0222 | 0.004555 | 99.57 | 0.44 | −0.4 |
| 108.43 | 0.33 | 106.42 | 0.29 | 1.0189 | 0.004176 | 99.25 | 0.41 | −0.7 |
| 110.31 | 0.58 | 107.95 | 0.34 | 1.0219 | 0.006292 | 99.55 | 0.61 | −0.5 |
| 113.02 | 0.46 | 108.45 | 0.49 | 1.0422 | 0.006346 | 101.52 | 0.62 | 1.5 |
| 110.20 | 0.25 | 107.31 | 0.27 | 1.0269 | 0.003445 | 100.03 | 0.34 | 0.0 |
| 112.27 | 0.69 | 110.04 | 0.60 | 1.0203 | 0.008361 | 99.39 | 0.81 | −0.6 |
| 113.71 | 0.22 | 103.47 | 0.34 | 1.0990 | 0.004243 | 107.06 | 0.41 | 7.1 |
| 111.15 | 0.23 | 108.68 | 0.24 | 1.0227 | 0.003089 | 99.63 | 0.30 | −0.4 |
| 111.12 | 0.20 | 108.19 | 0.16 | 1.0270 | 0.002364 | 100.05 | 0.23 | 0.0 |
| 112.07 | 0.28 | 108.75 | 0.17 | 1.0305 | 0.003069 | 100.39 | 0.30 | 0.4 |
| 117.56 | 0.47 | 114.73 | 0.68 | 1.0247 | 0.007318 | 99.82 | 0.71 | −0.2 |
| 114.49 | 0.39 | 111.83 | 0.24 | 1.0238 | 0.004107 | 99.74 | 0.40 | −0.3 |
| 110.91 | 0.31 | 108.26 | 0.18 | 1.0245 | 0.003293 | 99.80 | 0.32 | −0.2 |
| 109.34 | 0.32 | 106.69 | 0.19 | 1.0249 | 0.003488 | 99.84 | 0.34 | −0.2 |
| 108.10 | 0.24 | 105.87 | 0.26 | 1.0210 | 0.003421 | 99.46 | 0.33 | −0.5 |
| 110.17 | 0.61 | 108.38 | 0.72 | 1.0165 | 0.008772 | 99.02 | 0.85 | −1.0 |
| 110.95 | 0.29 | 107.84 | 0.12 | 1.0289 | 0.002873 | 100.23 | 0.28 | 0.2 |
| 110.04 | 1.21 | 107.53 | 0.74 | 1.0233 | 0.013269 | 99.69 | 1.29 | −0.3 |
| 110.94 | 1.42 | 107.40 | 0.71 | 1.0329 | 0.014882 | 100.62 | 1.45 | 0.6 |
| 111.97 | 0.79 | 109.46 | 0.42 | 1.0229 | 0.008172 | 99.65 | 0.80 | −0.4 |
| 111.91 | 0.93 | 109.34 | 0.41 | 1.0235 | 0.009328 | 99.70 | 0.91 | −0.3 |
| 111.58 | 0.17 | 107.56 | 0.18 | 1.0374 | 0.002374 | 101.05 | 0.23 | 1.1 |

FIG. 8 (Continued)

| | | |
|---|---|---|
| SEQ ID: 29 | DTLMISR | HC(248-254) |
| SEQ ID: 30 | TPEVTCVVVDVSHEDPEVK | HC(255-273) |
| SEQ ID: 31 | FNWYVDGVEVHNAK | HC(274-287) |
| SEQ ID: 32 | TKPREEQYN(G0F)STYR | HC(G0F-288-300) |
| SEQ ID: 33 | VVSVLTVLHQDWLNGKEYK | HC(301-319) |
| SEQ ID: 34 | CKVSNK | HC(320-325) |
| SEQ ID: 35 | ALPAPIEK | HC(326-333) |
| SEQ ID: 36 | TISK | HC(334-337) |
| SEQ ID: 37 | AKGQPR | HC(338-343) |
| SEQ ID: 38 | EPQVYTLPPSRDELTK | HC(344-359) |
| SEQ ID: 39 | NQVSLTCLVK | HC(360-369) |
| SEQ ID: 40 | GFYPSDIAVEWESNGQPENNYK | HC(370-391) |
| SEQ ID: 41 | TTPPVLDSDGSFFLYSK | HC(392-408) |
| SEQ ID: 42 | LTVDK | HC(409-413) |
| SEQ ID: 43 | SRWQQGNVFSCSVMHEALHNHYTQK | HC(414-438) |
| SEQ ID: 44 | WQQGNVFSCSVMHEALHNHYTQK | HC(416-438) |
| SEQ ID: 45 | TTPPVLDSDGSFFLYSKLTVDKSRWQQGNVFSCSVMHEALHNHYTQKSLSLSPG | HC(392-445) |
| SEQ ID: 46 | QVQLQESGPGLVKPSQTLSLTCTVSGYSISSDFAWNWIR | HC(Q1-39) |
| SEQ ID: 47 | YQPSLKSRITISR | HC(60-72) |
| SEQ ID: 48 | oxidized DTL(Mox)ISR | HC(ox248-254) |
| SEQ ID: 49 | deamidated GFYPSDIAVEWESNGQPENNYK | HC(d370-391) |
| SEQ ID: 50 | oxidized WQQGNVFSCSV(Mox)HEALHNHYTQK | HC(ox416-438) |
| SEQ ID: 51 | SLSLSPGK | HC(439-446) |
| SEQ ID: 52 | TKPREEQYN(G0F)STYR | G0F |
| SEQ ID: 53 | TKPREEQYN(G0)STYR | G0 |
| SEQ ID: 54 | TKPREEQYN(G0F-GlcNAc)STYR | G0F-GlcNAc |
| SEQ ID: 55 | TKPREEQYN(G1F)STYR | G1F |
| SEQ ID: 56 | TKPREEQYN(G2F)STYR | G2F |
| SEQ ID: 57 | TKPREEQYN(M5)STYR | M5 |
| SEQ ID: 58 | TKPREEQYN(M6)STYR | M6 |
| SEQ ID: 59 | TKPREEQYNSTYR | no oligo |

FIG. 8 (Continued)

| | | | | | | | | |
|---|---|---|---|---|---|---|---|---|
| 112.17 | 1.22 | 109.25 | 0.65 | 1.0267 | 0.012727 | 100.01 | 1.24 | 0.0 |
| 107.54 | 0.33 | 104.98 | 0.16 | 1.0244 | 0.003504 | 99.79 | 0.34 | -0.2 |
| 108.87 | 0.36 | 105.39 | 0.21 | 1.0330 | 0.003987 | 100.63 | 0.39 | 0.6 |
| 55.64 | 0.32 | 80.07 | 0.40 | 0.6949 | 0.005340 | 67.69 | 0.52 | -32.3 |
| 108.76 | 0.25 | 105.30 | 0.35 | 1.0329 | 0.004158 | 100.61 | 0.41 | 0.6 |
| 111.10 | 0.82 | 107.13 | 0.72 | 1.0371 | 0.010331 | 101.02 | 1.01 | 1.0 |
| 110.99 | 0.21 | 107.36 | 0.15 | 1.0338 | 0.002474 | 100.70 | 0.24 | 0.7 |
| 109.99 | 0.37 | 107.68 | 0.25 | 1.0214 | 0.004143 | 99.50 | 0.40 | -0.5 |
| 116.80 | 1.38 | 113.95 | 0.68 | 1.0250 | 0.013576 | 99.85 | 1.32 | -0.1 |
| 113.97 | 0.29 | 111.37 | 0.30 | 1.0234 | 0.003849 | 99.69 | 0.37 | -0.3 |
| 110.38 | 0.33 | 107.26 | 0.22 | 1.0290 | 0.003728 | 100.24 | 0.36 | 0.2 |
| 106.36 | 0.21 | 102.68 | 0.28 | 1.0358 | 0.003471 | 100.90 | 0.34 | 0.9 |
| 107.38 | 0.37 | 104.99 | 0.48 | 1.0228 | 0.005848 | 99.63 | 0.57 | -0.4 |
| 110.26 | 0.25 | 107.83 | 0.20 | 1.0225 | 0.002972 | 99.60 | 0.29 | -0.4 |
| 108.12 | 1.13 | 105.05 | 0.87 | 1.0292 | 0.013752 | 100.26 | 1.34 | 0.3 |
| 106.04 | 0.41 | 103.01 | 0.28 | 1.0294 | 0.004852 | 100.27 | 0.47 | 0.3 |
| 107.74 | 2.21 | 100.12 | 1.71 | 1.0762 | 0.028777 | 104.83 | 2.80 | 4.8 |
| 31.03 | 0.44 | 116.35 | 2.66 | 0.2667 | 0.007188 | 25.98 | 0.70 | -74.0 |
| 92.48 | 2.85 | 112.05 | 20.91 | 0.8254 | 0.156129 | 80.40 | 15.21 | -19.6 |
| 82.06 | 5.82 | 91.10 | 1.59 | 0.9008 | 0.065831 | 87.75 | 6.41 | -12.2 |
| 100.76 | 2.35 | 102.64 | 2.63 | 0.9816 | 0.033994 | 95.62 | 3.31 | -4.4 |
| 76.16 | 4.81 | 72.03 | 1.58 | 1.0574 | 0.070731 | 103.00 | 6.89 | 3.0 |
| 70.64 | 1.33 | 649.15 | 13.48 | 0.1088 | 0.003051 | 10.60 | 0.30 | -89.4 |
| 55.64 | 0.32 | 80.07 | 0.40 | 0.69 | 0.01 | 67.69 | 0.52 | -32.3 |
| 90.85 | 11.62 | 150.07 | 2.65 | 0.6054 | 0.078136 | 58.97 | 7.61 | -41.0 |
| 63.98 | 1.13 | 76.06 | 0.53 | 0.8413 | 0.015959 | 81.95 | 1.55 | -18.1 |
| 667.28 | 11.17 | 438.64 | 3.57 | 1.5213 | 0.028326 | 148.19 | 2.76 | 48.2 |
| 3781.59 | 200.48 | 865.83 | 109.82 | 4.3676 | 0.600399 | 425.46 | 58.49 | 325.5 |
| 35.20 | 0.64 | 87.14 | 1.56 | 0.4040 | 0.010277 | 39.35 | 1.00 | -60.6 |
| 64.41 | 6.96 | 194.41 | 54.21 | 0.3313 | 0.099067 | 32.27 | 9.65 | -67.7 |
| 157.90 | 10.56 | 217.71 | 5.63 | 0.7253 | 0.052005 | 70.65 | 5.07 | -29.3 | c value 1.0266

FIG. 8 (Continued)

| Measured Characteristic | SITRS | Conventional Method | |
|---|---|---|---|
| (G0F)$_{HEK}$ / (G0F)$_{CHO}$ * 100% | 67.69±0.52 | 68.25±2.24 | 2-AB labeling |
| (G1F)$_{HEK}$ / (G1F)$_{CHO}$ * 100% | 148.19±2.76 | 157.91±1.52 | 2-AB labeling |
| (M5)$_{HEK}$ / (M5)$_{CHO}$ * 100% | 39.35±1.00 | 56.80±8.51 | 2-AB labeling |
| (N-term Q)$_{HEK}$ / (N-term Q)$_{CHO}$ * 100% | 25.97±0.70 | 23.61±2.80 | Label-free MS |
| (N-term pE)$_{HEK}$ / (N-term pE)$_{CHO}$ * 100% | 107.06±0.41 | 111.87±0.60 | Label-free MS |
| (C-term K)$_{HEK}$ / (C-term K)$_{CHO}$ * 100% | 10.60±0.30 | 8.74±1.22 | Label-free MS |

FIG. 15

20% Mutant

| Unlabeled Peptides | | Labeled Peptides | | Unlabeled / Labeled |
|---|---|---|---|---|
| m/z | Abundance | m/z | Abundance | |
| 1070.5072 | 119000 | 1073.5171 | 120000 | |
| 1071.0085 | 136000 | 1074.0185 | 127000 | |
| 1071.5093 | 90300 | 1074.5191 | 81200 | |
| 1072.0098 | 44100 | 1075.0199 | 38800 | |
| 1072.5109 | 18400 | 1075.5203 | 15900 | |
| Sum of Unlabeled | 408000 | Sum of Labeled | 383000 | 1.07 |

0% Mutant

| Unlabeled Peptides | | Labeled Peptides | | Unlabeled / Labeled |
|---|---|---|---|---|
| m/z | Abundance | m/z | Abundance | |
| 1070.5085 | 113000 | 1073.5184 | 114000 | |
| 1071.0097 | 129000 | 1074.0197 | 120000 | |
| 1071.5108 | 85700 | 1074.5208 | 76300 | |
| 1072.0112 | 42700 | 1075.0214 | 36400 | |
| 1072.512 | 17600 | 1075.5218 | 14900 | |
| Sum of Unlabeled | 388000 | Sum of Labeled | 362000 | 1.07 |

FIG. 19

20% Mutant

| Unlabeled Peptides | | Labeled Peptides | | Unlabeled / Labeled |
|---|---|---|---|---|
| m/z | Abundance | m/z | Abundance | |
| 835.1521 | 58000 | 839.667 | 83200 | |
| 835.4024 | 109000 | 839.9174 | 135000 | |
| 835.6528 | 115000 | 840.1677 | 130000 | |
| 835.903 | 88600 | 840.418 | 92600 | |
| 836.1534 | 54600 | 840.6681 | 54600 | |
| 836.4038 | 29000 | 840.9176 | 29100 | |
| 836.6539 | 14200 | 841.1666 | 15000 | |
| 836.9044 | 6610 | 841.4146 | 8040 | |
| Sum of Unlabeled | 475000 | Sum of Labeled | 547000 | 0.87 |

0% Mutant

| Unlabeled Peptides | | Labeled Peptides | | Unlabeled / Labeled |
|---|---|---|---|---|
| m/z | Abundance | m/z | Abundance | |
| 835.1544 | 64200 | 839.6692 | 71800 | |
| 835.4047 | 120000 | 839.9197 | 116000 | |
| 835.6551 | 128000 | 840.1699 | 111000 | |
| 835.9054 | 97700 | 840.4203 | 79700 | |
| 836.1556 | 60800 | 840.6702 | 47000 | |
| 836.4059 | 32200 | 840.9197 | 25400 | |
| 836.6559 | 15800 | 841.1678 | 13500 | |
| 836.9062 | 7550 | 841.415 | 7470 | |
| Sum of Unlabeled | 526000 | Sum of Labeled | 472000 | 1.11 |

FIG. 21

SEQUENCE LISTING

```
<160> NUMBER OF SEQ ID NOS: 59

<210> SEQ ID NO 1
<211> LENGTH: 18
<212> TYPE: PRT
<213> ORGANISM: Homo sapiens

<400> SEQUENCE: 1

Asp Ile Gln Met Thr Gln Ser Pro Ser Ser Met Ser Val Ser Val Gly
1               5                   10                  15

Asp Arg

<210> SEQ ID NO 2
<211> LENGTH: 42
<212> TYPE: PRT
<213> ORGANISM: Homo sapiens

<400> SEQUENCE: 2

Asp Ile Gln Met Thr Gln Ser Pro Ser Ser Met Ser Val Ser Val Gly
1               5                   10                  15

Asp Arg Val Thr Ile Thr Cys His Ser Ser Gln Asp Ile Asn Ser Asn
            20                  25                  30

Ile Gly Trp Leu Gln Gln Lys Pro Gly Lys
        35                  40

<210> SEQ ID NO 3
<211> LENGTH: 16
<212> TYPE: PRT
<213> ORGANISM: Homo sapiens

<400> SEQUENCE: 3

Gly Leu Ile Tyr His Gly Thr Asn Leu Asp Asp Gly Val Pro Ser Arg
1               5                   10                  15

<210> SEQ ID NO 4
<211> LENGTH: 42
<212> TYPE: PRT
<213> ORGANISM: Homo sapiens
```

-continued

```
<400> SEQUENCE: 4

Phe Ser Gly Ser Gly Ser Gly Thr Asp Tyr Thr Leu Thr Ile Ser Ser
1               5                   10                  15

Leu Gln Pro Glu Asp Phe Ala Thr Tyr Tyr Cys Val Gln Tyr Ala Gln
            20                  25                  30

Phe Pro Trp Thr Phe Gly Gly Gly Thr Lys
            35                  40

<210> SEQ ID NO 5
<211> LENGTH: 5
<212> TYPE: PRT
<213> ORGANISM: Homo sapiens

<400> SEQUENCE: 5

Leu Glu Ile Lys Arg
1               5

<210> SEQ ID NO 6
<211> LENGTH: 18
<212> TYPE: PRT
<213> ORGANISM: Homo sapiens

<400> SEQUENCE: 6

Thr Val Ala Ala Pro Ser Val Phe Ile Phe Pro Pro Ser Asp Glu Gln
1               5                   10                  15

Leu Lys

<210> SEQ ID NO 7
<211> LENGTH: 16
<212> TYPE: PRT
<213> ORGANISM: Homo sapiens

<400> SEQUENCE: 7

Ser Gly Thr Ala Ser Val Val Cys Leu Leu Asn Asn Phe Tyr Pro Arg
1               5                   10                  15

<210> SEQ ID NO 8
<211> LENGTH: 4
<212> TYPE: PRT
<213> ORGANISM: Homo sapiens

<400> SEQUENCE: 8

Val Gln Trp Lys
1

<210> SEQ ID NO 9
<211> LENGTH: 20
<212> TYPE: PRT
<213> ORGANISM: Homo sapiens

<400> SEQUENCE: 9

Val Asp Asn Ala Leu Gln Ser Gly Asn Ser Gln Glu Ser Val Thr Glu
1               5                   10                  15

Gln Asp Ser Lys
            20

<210> SEQ ID NO 10
<211> LENGTH: 14
<212> TYPE: PRT
<213> ORGANISM: Homo sapiens
```

```
<400> SEQUENCE: 10

Asp Ser Thr Tyr Ser Leu Ser Ser Thr Leu Thr Leu Ser Lys
1               5                   10

<210> SEQ ID NO 11
<211> LENGTH: 5
<212> TYPE: PRT
<213> ORGANISM: Homo sapiens

<400> SEQUENCE: 11

Ala Asp Tyr Glu Lys
1               5

<210> SEQ ID NO 12
<211> LENGTH: 19
<212> TYPE: PRT
<213> ORGANISM: Homo sapiens

<400> SEQUENCE: 12

His Lys Val Tyr Ala Cys Glu Val Thr His Gln Gly Leu Ser Ser Pro
1               5                   10                  15

Val Thr Lys

<210> SEQ ID NO 13
<211> LENGTH: 7
<212> TYPE: PRT
<213> ORGANISM: Homo sapiens

<400> SEQUENCE: 13

Ser Phe Asn Arg Gly Glu Cys
1               5

<210> SEQ ID NO 14
<211> LENGTH: 39
<212> TYPE: PRT
<213> ORGANISM: Homo sapiens

<400> SEQUENCE: 14

Glu Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Ser Ser Asp
            20                  25                  30

Phe Ala Trp Asn Trp Ile Arg
        35

<210> SEQ ID NO 15
<211> LENGTH: 5
<212> TYPE: PRT
<213> ORGANISM: Homo sapiens

<400> SEQUENCE: 15

Gln Pro Pro Gly Lys
1               5

<210> SEQ ID NO 16
<211> LENGTH: 15
<212> TYPE: PRT
<213> ORGANISM: Homo sapiens

<400> SEQUENCE: 16

Gly Leu Glu Trp Met Gly Tyr Ile Ser Tyr Ser Gly Asn Thr Arg
1               5                   10                  15
```

```
<210> SEQ ID NO 17
<211> LENGTH: 6
<212> TYPE: PRT
<213> ORGANISM: Homo sapiens

<400> SEQUENCE: 17

Tyr Gln Pro Ser Leu Lys
1               5

<210> SEQ ID NO 18
<211> LENGTH: 7
<212> TYPE: PRT
<213> ORGANISM: Homo sapiens

<400> SEQUENCE: 18

Ser Arg Ile Thr Ile Ser Arg
1               5

<210> SEQ ID NO 19
<211> LENGTH: 5
<212> TYPE: PRT
<213> ORGANISM: Homo sapiens

<400> SEQUENCE: 19

Ile Thr Ile Ser Arg
1               5

<210> SEQ ID NO 20
<211> LENGTH: 10
<212> TYPE: PRT
<213> ORGANISM: Homo sapiens

<400> SEQUENCE: 20

Asp Thr Ser Lys Asn Gln Phe Phe Leu Lys
1               5                   10

<210> SEQ ID NO 21
<211> LENGTH: 19
<212> TYPE: PRT
<213> ORGANISM: Homo sapiens

<400> SEQUENCE: 21

Leu Asn Ser Val Thr Ala Ala Asp Thr Ala Thr Tyr Tyr Cys Val Thr
1               5                   10                  15

Ala Gly Arg

<210> SEQ ID NO 22
<211> LENGTH: 19
<212> TYPE: PRT
<213> ORGANISM: Homo sapiens

<400> SEQUENCE: 22

Gly Phe Pro Tyr Trp Gly Gln Gly Thr Leu Val Thr Val Ser Ser Ala
1               5                   10                  15

Ser Thr Lys

<210> SEQ ID NO 23
<211> LENGTH: 12
<212> TYPE: PRT
<213> ORGANISM: Homo sapiens

<400> SEQUENCE: 23

Gly Pro Ser Val Phe Pro Leu Ala Pro Ser Ser Lys
1               5                   10
```

```
<210> SEQ ID NO 24
<211> LENGTH: 14
<212> TYPE: PRT
<213> ORGANISM: Homo sapiens

<400> SEQUENCE: 24

Ser Thr Ser Gly Gly Thr Ala Ala Leu Gly Cys Leu Val Lys
1               5                   10

<210> SEQ ID NO 25
<211> LENGTH: 62
<212> TYPE: PRT
<213> ORGANISM: Homo sapiens

<400> SEQUENCE: 25

Asp Tyr Phe Pro Glu Pro Val Thr Val Ser Trp Asn Ser Gly Ala Leu
1               5                   10                  15

Thr Ser Gly Val His Thr Phe Pro Ala Val Leu Gln Ser Ser Gly Leu
            20                  25                  30

Tyr Ser Leu Ser Ser Val Val Thr Val Pro Ser Ser Leu Gly Thr Gln
        35                  40                  45

Thr Tyr Ile Cys Asn Val Asn His Lys Pro Ser Asn Thr Lys
    50                  55                  60

<210> SEQ ID NO 26
<211> LENGTH: 5
<212> TYPE: PRT
<213> ORGANISM: Homo sapiens

<400> SEQUENCE: 26

Lys Val Glu Pro Lys
1               5

<210> SEQ ID NO 27
<211> LENGTH: 4
<212> TYPE: PRT
<213> ORGANISM: Homo sapiens

<400> SEQUENCE: 27

Val Glu Pro Lys
1

<210> SEQ ID NO 28
<211> LENGTH: 30
<212> TYPE: PRT
<213> ORGANISM: Homo sapiens

<400> SEQUENCE: 28

Ser Cys Asp Lys Thr His Thr Cys Pro Pro Cys Pro Ala Pro Glu Leu
1               5                   10                  15

Leu Gly Gly Pro Ser Val Phe Leu Phe Pro Pro Lys Pro Lys
            20                  25                  30

<210> SEQ ID NO 29
<211> LENGTH: 7
<212> TYPE: PRT
<213> ORGANISM: Homo sapiens

<400> SEQUENCE: 29

Asp Thr Leu Met Ile Ser Arg
1               5
```

```
<210> SEQ ID NO 30
<211> LENGTH: 19
<212> TYPE: PRT
<213> ORGANISM: Homo sapiens

<400> SEQUENCE: 30

Thr Pro Glu Val Thr Cys Val Val Val Asp Val Ser His Glu Asp Pro
1               5                   10                  15

Glu Val Lys

<210> SEQ ID NO 31
<211> LENGTH: 14
<212> TYPE: PRT
<213> ORGANISM: Homo sapiens

<400> SEQUENCE: 31

Phe Asn Trp Tyr Val Asp Gly Val Glu Val His Asn Ala Lys
1               5                   10

<210> SEQ ID NO 32
<211> LENGTH: 13
<212> TYPE: PRT
<213> ORGANISM: Homo sapiens
<220> FEATURE:
<221> NAME/KEY: MISC_FEATURE
<222> LOCATION: (9)..(9)
<223> OTHER INFORMATION: G0F sugar modification

<400> SEQUENCE: 32

Thr Lys Pro Arg Glu Glu Gln Tyr Asn Ser Thr Tyr Arg
1               5                   10

<210> SEQ ID NO 33
<211> LENGTH: 19
<212> TYPE: PRT
<213> ORGANISM: Homo sapiens

<400> SEQUENCE: 33

Val Val Ser Val Leu Thr Val Leu His Gln Asp Trp Leu Asn Gly Lys
1               5                   10                  15

Glu Tyr Lys

<210> SEQ ID NO 34
<211> LENGTH: 6
<212> TYPE: PRT
<213> ORGANISM: Homo sapiens

<400> SEQUENCE: 34

Cys Lys Val Ser Asn Lys
1               5

<210> SEQ ID NO 35
<211> LENGTH: 8
<212> TYPE: PRT
<213> ORGANISM: Homo sapiens

<400> SEQUENCE: 35

Ala Leu Pro Ala Pro Ile Glu Lys
1               5

<210> SEQ ID NO 36
<211> LENGTH: 4
<212> TYPE: PRT
<213> ORGANISM: Homo sapiens
```

```
<400> SEQUENCE: 36

Thr Ile Ser Lys
1

<210> SEQ ID NO 37
<211> LENGTH: 6
<212> TYPE: PRT
<213> ORGANISM: Homo sapiens

<400> SEQUENCE: 37

Ala Lys Gly Gln Pro Arg
1               5

<210> SEQ ID NO 38
<211> LENGTH: 16
<212> TYPE: PRT
<213> ORGANISM: Homo sapiens

<400> SEQUENCE: 38

Glu Pro Gln Val Tyr Thr Leu Pro Pro Ser Arg Asp Glu Leu Thr Lys
1               5                   10                  15

<210> SEQ ID NO 39
<211> LENGTH: 10
<212> TYPE: PRT
<213> ORGANISM: Homo sapiens

<400> SEQUENCE: 39

Asn Gln Val Ser Leu Thr Cys Leu Val Lys
1               5                   10

<210> SEQ ID NO 40
<211> LENGTH: 22
<212> TYPE: PRT
<213> ORGANISM: Homo sapiens

<400> SEQUENCE: 40

Gly Phe Tyr Pro Ser Asp Ile Ala Val Glu Trp Glu Ser Asn Gly Gln
1               5                   10                  15

Pro Glu Asn Asn Tyr Lys
            20

<210> SEQ ID NO 41
<211> LENGTH: 17
<212> TYPE: PRT
<213> ORGANISM: Homo sapiens

<400> SEQUENCE: 41

Thr Thr Pro Pro Val Leu Asp Ser Asp Gly Ser Phe Phe Leu Tyr Ser
1               5                   10                  15

Lys

<210> SEQ ID NO 42
<211> LENGTH: 5
<212> TYPE: PRT
<213> ORGANISM: Homo sapiens

<400> SEQUENCE: 42

Leu Thr Val Asp Lys
1               5
```

```
<210> SEQ ID NO 43
<211> LENGTH: 25
<212> TYPE: PRT
<213> ORGANISM: Homo sapiens

<400> SEQUENCE: 43

Ser Arg Trp Gln Gln Gly Asn Val Phe Ser Cys Ser Val Met His Glu
1               5                   10                  15

Ala Leu His Asn His Tyr Thr Gln Lys
            20                  25

<210> SEQ ID NO 44
<211> LENGTH: 23
<212> TYPE: PRT
<213> ORGANISM: Homo sapiens

<400> SEQUENCE: 44

Trp Gln Gln Gly Asn Val Phe Ser Cys Ser Val Met His Glu Ala Leu
1               5                   10                  15

His Asn His Tyr Thr Gln Lys
            20

<210> SEQ ID NO 45
<211> LENGTH: 54
<212> TYPE: PRT
<213> ORGANISM: Homo sapiens

<400> SEQUENCE: 45

Thr Thr Pro Pro Val Leu Asp Ser Asp Gly Ser Phe Phe Leu Tyr Ser
1               5                   10                  15

Lys Leu Thr Val Asp Lys Ser Arg Trp Gln Gln Gly Asn Val Phe Ser
            20                  25                  30

Cys Ser Val Met His Glu Ala Leu His Asn His Tyr Thr Gln Lys Ser
        35                  40                  45

Leu Ser Leu Ser Pro Gly
    50

<210> SEQ ID NO 46
<211> LENGTH: 39
<212> TYPE: PRT
<213> ORGANISM: Homo sapiens

<400> SEQUENCE: 46

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Ser Ser Asp
            20                  25                  30

Phe Ala Trp Asn Trp Ile Arg
        35

<210> SEQ ID NO 47
<211> LENGTH: 13
<212> TYPE: PRT
<213> ORGANISM: Homo sapiens

<400> SEQUENCE: 47

Tyr Gln Pro Ser Leu Lys Ser Arg Ile Thr Ile Ser Arg
1               5                   10
```

```
<210> SEQ ID NO 48
<211> LENGTH: 7
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: M is oxidized

<400> SEQUENCE: 48

Asp Thr Leu Met Ile Ser Arg
1               5

<210> SEQ ID NO 49
<211> LENGTH: 22
<212> TYPE: PRT
<213> ORGANISM: Homo sapiens

<400> SEQUENCE: 49

Gly Phe Tyr Pro Ser Asp Ile Ala Val Glu Trp Glu Ser Asn Gly Gln
1               5                   10                  15

Pro Glu Asn Asn Tyr Lys
            20

<210> SEQ ID NO 50
<211> LENGTH: 23
<212> TYPE: PRT
<213> ORGANISM: Homo sapiens
<220> FEATURE:
<221> NAME/KEY: MISC_FEATURE
<222> LOCATION: (12)..(12)
<223> OTHER INFORMATION: M is oxidized

<400> SEQUENCE: 50

Trp Gln Gln Gly Asn Val Phe Ser Cys Ser Val Met His Glu Ala Leu
1               5                   10                  15

His Asn His Tyr Thr Gln Lys
            20

<210> SEQ ID NO 51
<211> LENGTH: 8
<212> TYPE: PRT
<213> ORGANISM: Homo sapiens

<400> SEQUENCE: 51

Ser Leu Ser Leu Ser Pro Gly Lys
1               5

<210> SEQ ID NO 52
<211> LENGTH: 13
<212> TYPE: PRT
<213> ORGANISM: Homo sapiens
<220> FEATURE:
<221> NAME/KEY: MISC_FEATURE
<222> LOCATION: (9)..(9)
<223> OTHER INFORMATION: G0F sugar modification

<400> SEQUENCE: 52

Thr Lys Pro Arg Glu Glu Gln Tyr Asn Ser Thr Tyr Arg
1               5                   10

<210> SEQ ID NO 53
<211> LENGTH: 13
<212> TYPE: PRT
<213> ORGANISM: Homo sapiens
```

```
<220> FEATURE:
<221> NAME/KEY: MISC_FEATURE
<222> LOCATION: (9)..(9)
<223> OTHER INFORMATION: G0 sugar modification

<400> SEQUENCE: 53

Thr Lys Pro Arg Glu Glu Gln Tyr Asn Ser Thr Tyr Arg
1               5                   10

<210> SEQ ID NO 54
<211> LENGTH: 13
<212> TYPE: PRT
<213> ORGANISM: Homo sapiens
<220> FEATURE:
<221> NAME/KEY: MISC_FEATURE
<222> LOCATION: (9)..(9)
<223> OTHER INFORMATION: G0F-GlcNAc sugar modification

<400> SEQUENCE: 54

Thr Lys Pro Arg Glu Glu Gln Tyr Asn Ser Thr Tyr Arg
1               5                   10

<210> SEQ ID NO 55
<211> LENGTH: 13
<212> TYPE: PRT
<213> ORGANISM: Homo sapiens
<220> FEATURE:
<221> NAME/KEY: MISC_FEATURE
<222> LOCATION: (9)..(9)
<223> OTHER INFORMATION: G1F sugar modification

<400> SEQUENCE: 55

Thr Lys Pro Arg Glu Glu Gln Tyr Asn Ser Thr Tyr Arg
1               5                   10

<210> SEQ ID NO 56
<211> LENGTH: 13
<212> TYPE: PRT
<213> ORGANISM: Homo sapiens
<220> FEATURE:
<221> NAME/KEY: MISC_FEATURE
<222> LOCATION: (9)..(9)
<223> OTHER INFORMATION: G2F sugar modification

<400> SEQUENCE: 56

Thr Lys Pro Arg Glu Glu Gln Tyr Asn Ser Thr Tyr Arg
1               5                   10

<210> SEQ ID NO 57
<211> LENGTH: 13
<212> TYPE: PRT
<213> ORGANISM: Homo sapiens
<220> FEATURE:
<221> NAME/KEY: MISC_FEATURE
<222> LOCATION: (9)..(9)
<223> OTHER INFORMATION: M5 sugar modification

<400> SEQUENCE: 57

Thr Lys Pro Arg Glu Glu Gln Tyr Asn Ser Thr Tyr Arg
1               5                   10

<210> SEQ ID NO 58
<211> LENGTH: 13
<212> TYPE: PRT
<213> ORGANISM: Homo sapiens
<220> FEATURE:
<221> NAME/KEY: MISC_FEATURE
<222> LOCATION: (9)..(9)
<223> OTHER INFORMATION: M6 sugar modification
```

```
<400> SEQUENCE: 58

Thr Lys Pro Arg Glu Glu Gln Tyr Asn Ser Thr Tyr Arg
1               5                   10

<210> SEQ ID NO 59
<211> LENGTH: 13
<212> TYPE: PRT
<213> ORGANISM: Homo sapiens

<400> SEQUENCE: 59

Thr Lys Pro Arg Glu Glu Gln Tyr Asn Ser Thr Tyr Arg
1               5                   10
```

METHODS AND SYSTEMS FOR THE ANALYSIS OF PROTEIN SAMPLES

RELATED APPLICATIONS

This application is a continuation-in-part of U.S. patent application Ser. No. 13/161,907, filed Jun. 16, 2011, which claims the benefit of priority of U.S. Provisional Application Ser. No. 61/355,269, filed Jun. 16, 2010, which are both incorporated herein by reference in their entirety. This application also claims the benefit of U.S. Provisional Application Ser. No. 61/466,912, filed Mar. 23, 2011, which is also incorporated herein by reference in its entirety.

1. INTRODUCTION

The present invention relates to methods for analyzing protein samples, e.g., monoclonal antibody ("MAb") samples, via bottom-up Liquid Chromatography-Mass Spectroscopy ("LC-MS") with a Stable Isotope-Tagged Reference Standard, a process referred to hereinafter as the "SITRS" technique, as well as methods and systems that facilitate the processing of data generated by the SITRS technique.

2. BACKGROUND OF THE INVENTION

Peptide mapping with mass spectroscopy ("MS") detection enjoys widespread use in protein analytics, particularly for confirmation of the primary sequences of many types of proteins, including MAbs. However, one limitation of existing MS analytical methods is that they are primarily focused on qualitatively confirming the presence of expected peptides.

A recent development that allows for the extension of MS detection to quantitative analysis of protein samples is the availability of isotopically-labeled amino acids. For example, proteins comprising isotopically-labeled amino acids can be utilized in the Stable Isotope Labeling with amino acids in Cell culture ("SILAC") method to detect differences in protein abundance between two or more samples.

The SILAC method involves first establishing two independent cell cultures. The first culture is supplemented with isotopically-labeled amino acids and the second is supplemented with standard amino acids. After sufficient time has elapsed to allow for uniform incorporation of the isotopically-labeled amino acids into the proteome of the first culture (e.g., 5 cell doublings), the proteomes of the two cultures (or sub-proteomes thereof) are isolated, digested, and subjected to MS analysis. If a protein of interest is expressed in both the isotopically-labeled culture and the standard culture, the digestion step will result in peptide fragment pairs where one member is isotopically labeled and one that is not. Because MS analysis results in an intensity peak for each peptide fragment of a digested protein, each peptide fragment pair will appear as two distinct MS intensity peaks, which are separated by the mass of the isotopic label(s) incorporated into the labeled member of the pair. The two MS intensity peaks for any one peptide fragment pair can be compared and the ratio of the peak intensities reflects not only the presence of the protein in each of the two cultures, but also allows for the calculation of an abundance ratio for the proteins made by the two cultures. Thus, the SILAC method can be used to qualitatively confirm the presence of particular proteins in a cell population and to quantitatively determine protein abundances in different cell populations.

Although the SILAC method allows for certain types of qualitative and quantitative analysis, there remains a need in the art for protein analytics capable of qualitatively and/or quantitatively detecting the presence of (1) mutations, e.g., insertions, deletions, or substitutions; (2) modifications, e.g., the presence of glycosylation or methylation; or (3) polypeptide impurities, e.g., polypeptides present in a sample that have one or more identical sequence fragments when compared to a protein of interest, including, but not limited to a degradation product of the protein of interest. The instant invention addresses this need.

3. SUMMARY OF THE INVENTION

In certain embodiments, the present invention relates to methods for detecting the presence of a mutation, modification, or polypeptide impurity in a sample of a protein of interest comprising the steps of: (1) mixing a sample of a protein of interest with a SITRS protein standard, e.g., a reference sample of the protein of interest having a known sequence and comprising an isotopically-labeled amino acid; (2) subjecting the mixture to protein digestion to generate two or more peptide fragments; (3) subjecting that digest to bottom-up liquid chromatography-mass spectrometry; and (4) comparing the m/z values corresponding to the mass spectra of one or more of the peptide fragments.

In certain embodiments, the m/z values will correspond to the mass spectra of peptides that cover more than 50% of the protein sequence of the protein of interest. In certain embodiments, the m/z values will correspond to the mass spectra of peptides that cover more than 60% of the protein sequence. In certain embodiments, the m/z values will correspond to the mass spectra of peptides that cover more than 70% of the protein sequence. In certain embodiments, the m/z values will correspond to the mass spectra of peptides that cover more than 80% of the protein sequence. In certain embodiments, the m/z values will correspond to the mass spectra of peptides that cover more than 90% of the protein sequence. In certain embodiments, the m/z values will correspond to the mass spectra of peptides that cover more than 95% of the protein sequence. In certain embodiments, the m/z values will correspond to the mass spectra of peptides that cover the entire protein sequence.

In certain embodiments, the comparison of peptide fragment m/z values comprises the following steps: (1) identifying those m/z values that correspond to peptide fragments comprising an isotopically-labeled amino acid, i.e., those fragments that are derived from the SITRS protein standard; (2) identifying the presence of a doublet indicating the presence of a peptide fragment with an isotopically labeled amino acid and a corresponding peptide fragment without an isotopically labeled amino acid; (3) comparing the relative intensities of the m/z values in the doublet to determine the relative amount of the peptide fragment in the sample of the protein of interest and the sample of the SITRS protein standard, where a difference in the relative amount of the peptide fragments indicates the presence of a mutation, modification, or polypeptide impurity in the sample of the protein of interest.

In certain embodiments of the above-described SITRS technique, a decrease in the relative intensity of the m/z value corresponding the protein of interest relative to the reference protein is indicative of a mutation, modification, or polypeptide impurity in the sample of the protein of interest. In certain embodiments, the sample of the protein of interest is subsequently subjected to tandem mass spectrometry to ascertain the identity of the mutation, modification, or polypeptide impurity present in the sample.

In certain embodiments, the present invention relates to methods for comparing two protein samples of interest to determine the presence of a mutation, modification, or polypeptide impurity in either sample. In certain embodiments, the methods comprise the steps of: (1) mixing a first sample of a protein of interest with a sample of a corresponding SITRS protein standard; (2) subjecting the mixture to protein digestion to form a digest of two or more peptides; (3) subjecting that digest to bottom-up liquid chromatography-mass spectrometry; and (4) comparing the m/z values corresponding to the mass spectra of one or more of the peptides (wherein such comparison comprises: identifying those m/z values that correspond to fragments of the SITRS protein standard; identifying the presence of a doublet indicating the presence of a peptide with an isotopically labeled amino acid and a corresponding peptide without an isotopically labeled amino acid; and comparing the relative intensities of the m/z values in the doublet to determine the relative amount of the peptide in the sample of the first protein of interest and of corresponding peptide in the SITRS protein standard—thereby preparing a first intensity ratio). In certain embodiments, the foregoing steps are preceded, followed, or are completed concurrently with the following steps: (1) mixing a second sample of a protein of interest with a corresponding SITRS protein standard; (2) subjecting the mixture to protein digestion to form a digest of two or more peptides; (3) subjecting that digest to bottom-up liquid chromatography-mass spectrometry; and (4) comparing the m/z values corresponding to the mass spectra of one or more of the peptides (wherein such comparison comprises; identifying those m/z values that correspond to peptides comprising an isotopically labeled amino acid; identifying the presence of a doublet indicating the presence of a peptide with an isotopically labeled amino acid and a corresponding peptide without an isotopically labeled amino acid; and comparing the relative intensities of the m/z values in the doublet to determine the relative amount of the peptide in the sample of the protein of interest and the sample of the SITRS protein standard, thereby preparing a second intensity ratio); followed by comparing the first and second intensity ratios to thereby detect the presence of a mutation, modification, or polypeptide impurity in the samples of the proteins of interest.

In certain embodiments of the above-described SITRS technique, a decrease of the first intensity ratio as compared to the second intensity ratio is indicative of a mutation, modification, or polypeptide impurity in the first sample of the protein of interest. In certain embodiments of the above-described SITRS technique, a decrease of the second intensity ratio as compared to the first intensity ratio is indicative of a mutation, modification, or impurity in the second sample of the protein of interest.

In certain embodiments of the above-described SITRS techniques, the step of identifying those m/z values that correspond to peptides comprising an isotopically labeled amino acid comprises: (1) input of the m/z values into a software application; (2) input of the retention time, e.g., estimated retention times determined by sequence analysis, corresponding to the peptides into the software application; (3) using the software application to correlate the m/z values with the retention times; and (4) thereby identifying those m/z values that correspond to peptides comprising an isotopically labeled amino acid.

In certain embodiments of the above-described SITRS techniques, the step of identifying the presence of a doublet indicating the presence of a peptide with an isotopically labeled amino acid and a corresponding peptide without an isotopically labeled amino acid comprises: (1) input of the identity of those m/z values that correspond to peptides comprising an isotopically labeled amino acid into the software application; (2) comparison by the software application of the identity of those m/z values that correspond to peptides comprising an isotopically labeled amino acid to the m/z values input into the application as described above; and (3) thereby identifying the presence of a doublet indicating the presence of a peptide with an isotopically labeled amino acid and a corresponding peptide without an isotopically labeled amino acid.

In certain embodiments of the above-described SITRS techniques, the step of comparing the relative intensities of the m/z values in the doublet to determine the relative amount of the peptide in the sample of the protein of interest and the sample of the SITRS protein reference comprises: (1) input of m/z values identified as a doublet indicating the presence of a peptide with an isotopically labeled amino acid and a corresponding peptide without an isotopically labeled amino acid into the software application; (2) comparison by the software application of the relative intensities of the m/z values in the doublet; and (3) thereby determining the relative amount of the peptide in the sample of the protein of interest and the sample of the SITRS protein standard.

In certain embodiments of the above-described STIRS techniques, the steps of comparing the relative intensities of the m/z values in a doublet to determine the relative amount of the peptide in the sample of the first protein of interest and the sample of the SITRS protein standard, which is then used to prepare a first intensity ratio, and comparing the relative intensities of the m/z values in a doublet to determine the relative amount of the peptide in the second sample of the protein of interest and the sample of the SITRS protein standard, which is then used to prepare a second intensity ratio, comprises: (1) separately identifying those m/z values that correspond to peptides comprising an isotopically labeled amino acid for the mixture of the first sample of protein of interest and the SITRS protein standard and for the second sample of protein of interest and the SITRS protein standard according to the method described above; (2) separately identifying the presence of a doublet indicating the presence of a peptide with an isotopically labeled amino acid and a corresponding peptide without an isotopically labeled amino acid for the mixture of the first sample of protein of interest and the SITRS protein standard and for the second sample of protein of interest and the SITRS protein standard according to the method described above; (3) separately comparing the relative intensities of the m/z values in the doublet to determine the relative amount of the peptide in the first sample of the protein of interest as compared to the sample of the SITRS protein standard and for the relative amount of the peptide in the second sample of protein of interest as compared to the STIRS protein standard according to the method described above; and thereby preparing the first intensity ratio and the second intensity ratio.

In certain embodiments of the above-described STIRS techniques, the step of comparing the first and second intensity ratios to thereby detect the presence of a mutation, modification, or polypeptide impurity in the samples of the protein of interest comprises: (1) input into the software application of the first and second intensity ratios prepared as described above; (2) comparison of the first and second intensity ratios by the software application; and (3) thereby detecting the presence of a mutation, modification, or polypeptide impurity in the samples of the protein of interest.

In certain embodiments, the present invention relates to a system comprising: a controller that controls various components of the system and allows for user-input of data; a spectrum data processor capable of: identifying individual m/z values; and comparing the relative intensities of the individual m/z values; and an output unit that outputs the result of the processing performed by the spectrum data processor.

In certain embodiments, the spectrum data processor uses user defined m/z monoisotopic peaks and user defined peptide charge states for calculating intensity ratios. In certain embodiments, the spectrum data processor automatically calculates which m/z monoisotopic peaks and peptide charge states should be used for calculating intensity ratios.

In certain embodiments, the above-described system further comprising a mass spectrometer in functional communication with the system.

In certain embodiments, the above-described system further comprises a liquid chromatography apparatus in functional communication with the system.

In certain embodiments, the above-described system is configured such that the functions performed by the controller, the spectrum data processor, and the output unit are accomplished by executing one or more software applications installed on a general purpose computer in functional communication with the system.

In certain embodiments, the present invention relates to a software application comprising instructions capable of being executed on a processor so as to perform a method for the comparison of mass spectrometry data. In certain embodiments, the method performed by the software applications comprises: providing a system, wherein the system comprises distinct software modules (wherein the distinct software modules comprise: a receiving mass spectrometer data module; a user-input module, and a data processing module); obtaining a first plurality of mass measurements produced by a mass spectrometer corresponding to peptides obtained from a digested mixture of a sample of a protein of interest and a sample of an isotopically labeled SITRS protein standard using the receiving mass spectrometer data module; using the user-input module to obtain one or more of the following: a list of m/z values corresponding to the monoisotopic peak or peaks included in the plurality of mass measurements; a list of retention time values corresponding to the plurality of mass measurements; a error tolerance/deviation for m/z and retention time values described above; a minimum and/or maximum intensity that is allowed for the m/z values; one or more m/z values with corresponding retention times for normalization of the retention times listed above; and the names that are to be associated with the mass measurements and the results output files; and using the data processing module to compare the m/z values corresponding to the mass measurements (wherein such data processing comprises: identifying those m/z values that correspond to peptides comprising an isotopically labeled amino acid; identifying the presence of a doublet indicating the presence of a peptide with an isotopically labeled amino acid and a corresponding peptide without an isotopically labeled amino acid; and comparing the relative intensities of the m/z values in the doublet to determine the relative amount of the peptide in the sample of the protein of interest and the sample of the SITRS protein standard to thereby detect the presence of a mutation, modification, or polypeptide impurity in the sample of the protein of interest.

In certain embodiments, the present invention relates to software application comprising instructions capable of being executed on a processor so as to perform a method for the comparison of mass spectrometry data. In certain embodiments the method comprises: providing a system, wherein the system comprises distinct software modules, and wherein the distinct software modules comprise: a receiving mass spectrometer data module; a user-input module, and a data processing module; obtaining a first plurality of mass measurements produced by a mass spectrometer corresponding to peptides obtained from a digested mixture of a sample of a first protein of interest and a sample of an isotopically labeled SITRS protein standard using the receiving mass spectrometer data module; using the user-input module to obtain one or more of the following: a list of m/z values corresponding to the monoisotopic peak or peaks included in the plurality of mass measurements; a list of retention time values corresponding to the plurality of mass measurements; a error tolerance/deviation for m/z and retention time values described above; a minimum and/or maximum intensity that is allowed for the m/z values; one or more m/z values with corresponding retention times for normalization of the retention times described above; and the names that are to be associated with the mass measurements and the results output files; using the data processing module to compare the m/z values corresponding to the mass measurements (wherein such data processing comprises; identifying those m/z values that correspond to peptides comprising an isotopically labeled amino acid; identifying the presence of a doublet indicating the presence of a peptide with an isotopically labeled amino acid and a corresponding peptide without an isotopically labeled amino acid; and comparing the relative intensities of the m/z values in the doublet to determine the relative amount of the peptide in the sample of the protein of interest and the sample of the reference protein to prepare a first intensity ratio. In certain embodiments, the method further comprises obtaining a second plurality of mass measurements produced by a mass spectrometer corresponding to peptides obtained from a digested mixture of a second sample of a protein of interest and a sample of the SITRS protein standard using the receiving mass spectrometer data module; using the user-input module to obtain one or more of the following; a list of m/z values corresponding to the monoisotopic peak or peaks included in the plurality of mass measurements; a list of retention time values corresponding to the plurality of mass measurements; a error tolerance/deviation for m/z and retention time values as described above; a minimum and/or maximum intensity that is allowed for the m/z values; one or more m/z values with corresponding retention times for normalization of the retention times described above; and the names that are to be associated with the mass measurements and the results output files; using the data processing module to compare the m/z values corresponding to the mass measurements (wherein such data processing comprises; identifying those m/z values that correspond to peptides comprising an isotopically labeled amino acid; identifying the presence of a doublet indicating the presence of a peptide with an isotopically labeled amino acid and a corresponding peptide without an isotopically labeled amino acid; comparing the relative intensities of the m/z values in the doublet to determine the relative amount of the peptide in the sample of the protein of interest and the sample of the reference protein to prepare a second intensity ratio; and comparing the first and second intensity ratios to thereby detect the presence of a mutation, modification, or polypeptide impurity in the samples of the protein of interest.

In certain embodiments, the present invention relates to a software application product, comprising a tangible computer-readable storage medium whose contents comprise a software application as described above.

4. BRIEF DESCRIPTION OF THE FIGURES

FIG. 1 is a schematic diagram of a SITRS experiment in accordance with the present analysis.

FIG. 2A-B (A) is a schematic of an exemplary LC-MS analysis with SITRS (no mutation or modification) in accordance with the present analysis; (B) is a schematic of an exemplary LC-MS analysis with SITRS that shows a peptide with a possible mutation or modification in accordance with the present analysis FIG. 3 is a spectra demonstrating antibody desalting utilizing the size exclusion chromatography—high performance liquid chromatography in accordance with the present analysis.

FIG. 4 is a representative mass spectrum of MAb-1 peptide generated by tryptic digest in the presence of its SITRS counterpart in accordance with the present analysis.

FIG. 5 is a comparison of mass spectra of a peptide from (A) pure unlabeled MAb-1 and (B) MAb-1 contaminated with 10% MAb-2. SITRS was mixed with each in a 1:1 ratio prior to tryptic digest and analysis in accordance with the present analysis FIG. 6 is a graph depicting SITRS values for 6 peptides studied in the quantitation of a MAb-1 sample contaminated with 10% MAb-2 in accordance with the present analysis.

FIG. 8 depicts a particular output of a software of the present analysis. The data in this table relates specifically to the expression of ANTIBODY A in HEK cells as compared to the expression of ANTIBODY A in CHO cells (82009BF).

Figure 9:
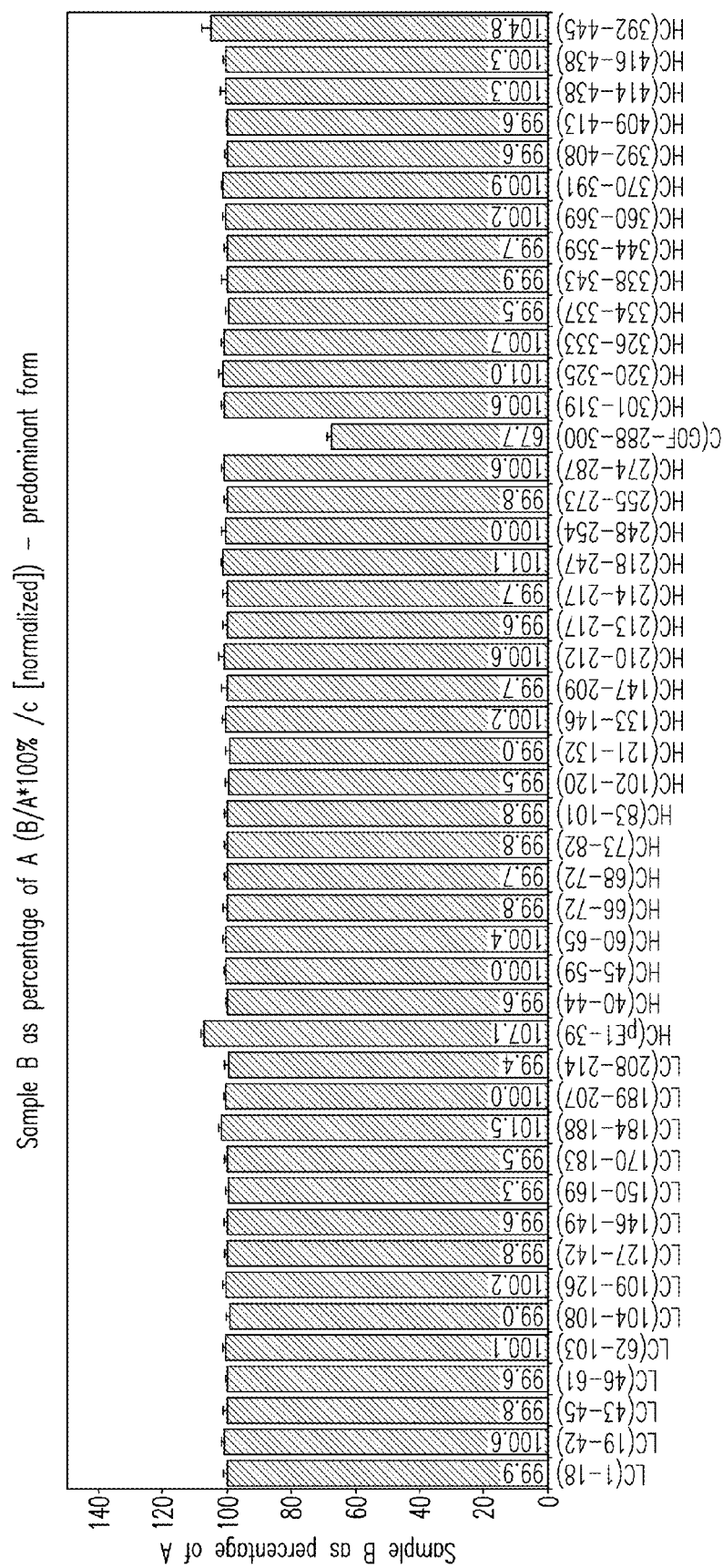
Figure 9:
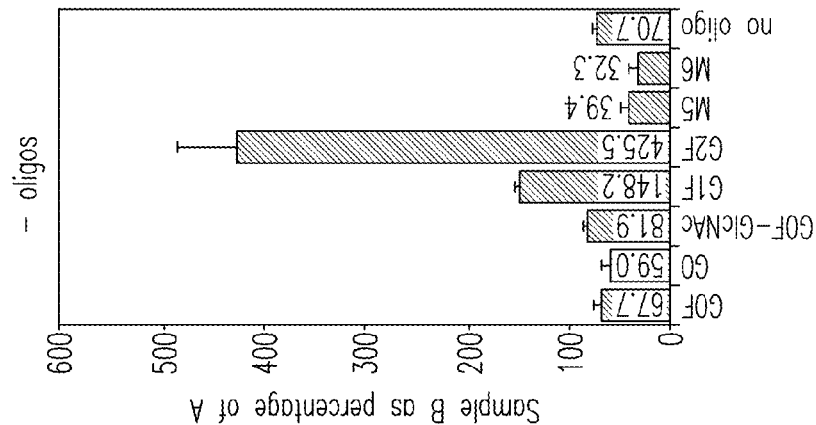
Figure 9:
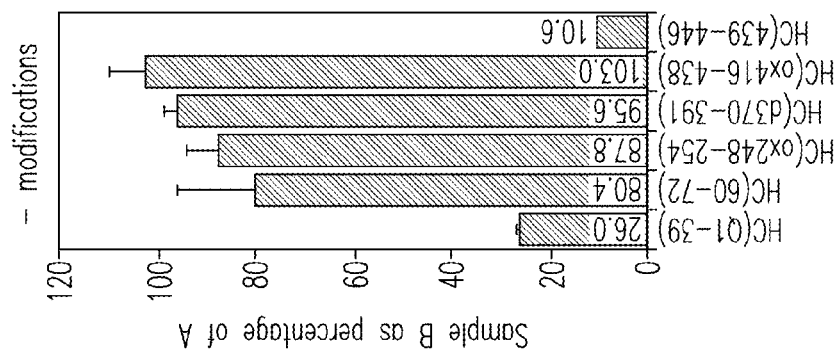
Figure 9:
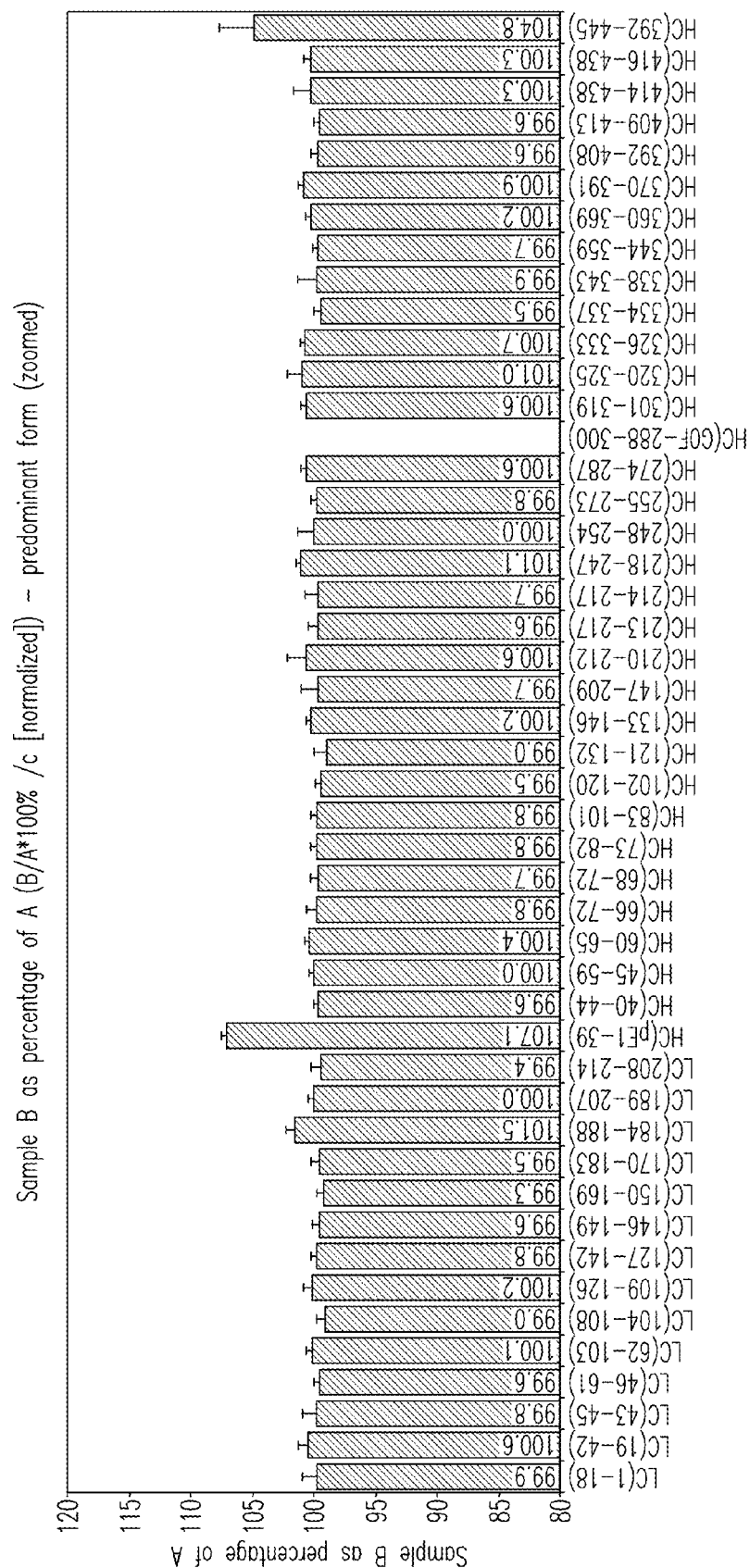

FIG. 9 depicts two examples of a second output of a software of the present analysis. The data in these tables relates to: (A) the presence of amino acid mutations in ANTIBODY A expressed in HEK cells as compared to the expression of ANTIBODY A in CHO cells (82009BF); and (B) the presence of particular carbohydrates on ANTIBODY A expressed in HEK cells as compared to ANTIBODY A expressed in CHO cells (82009BF).

Figure 10:
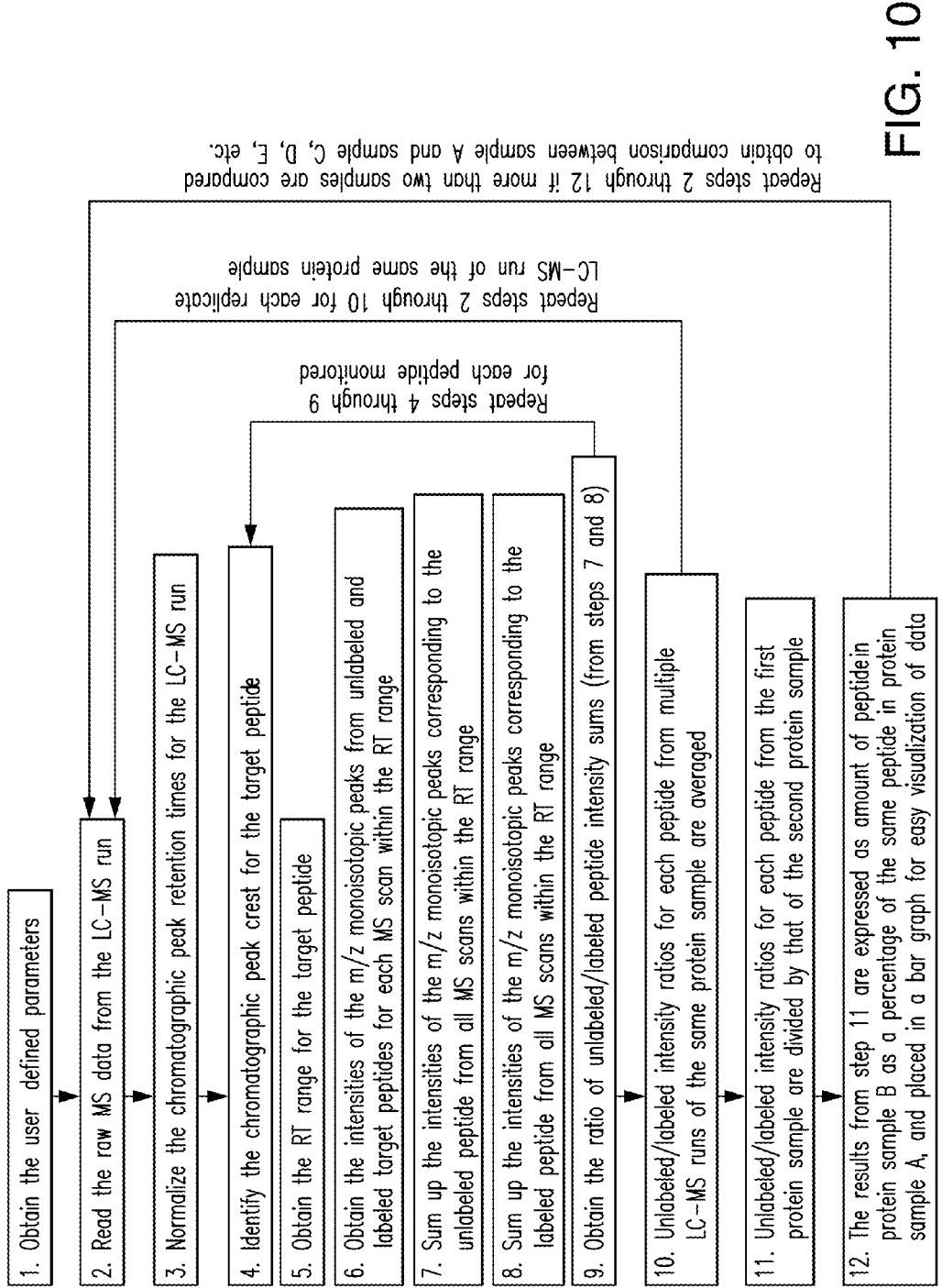

FIG. 10 is scheme for the analysis performed by the SITRS software.

Figure 11:
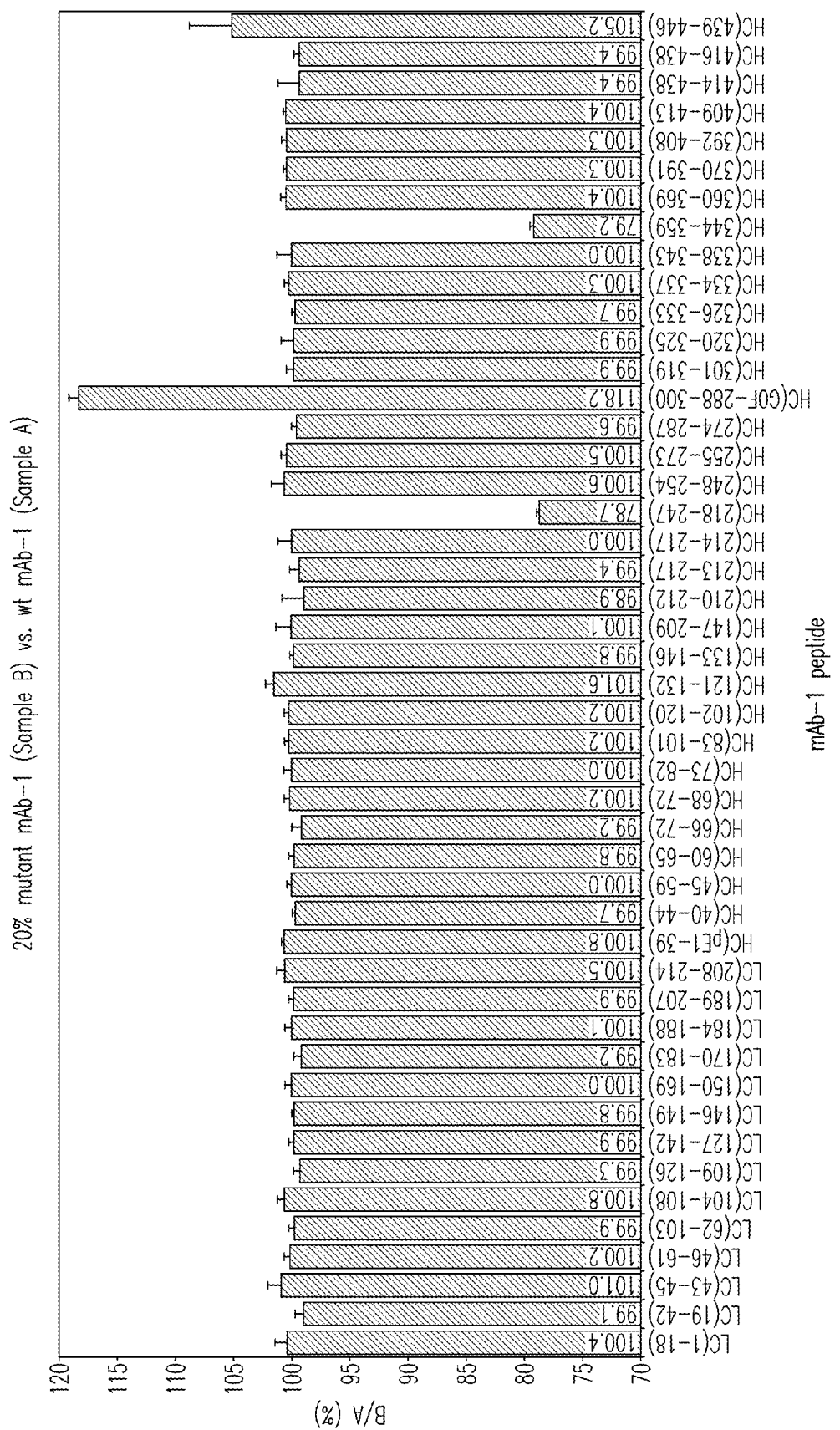

FIG. 11 is a SITRS bar graph for the SITRS experiment in which wt mAb-1 was compared to mAb-1 that was spiked with mutant to 20% in accordance with the present analysis.

Figure 12:
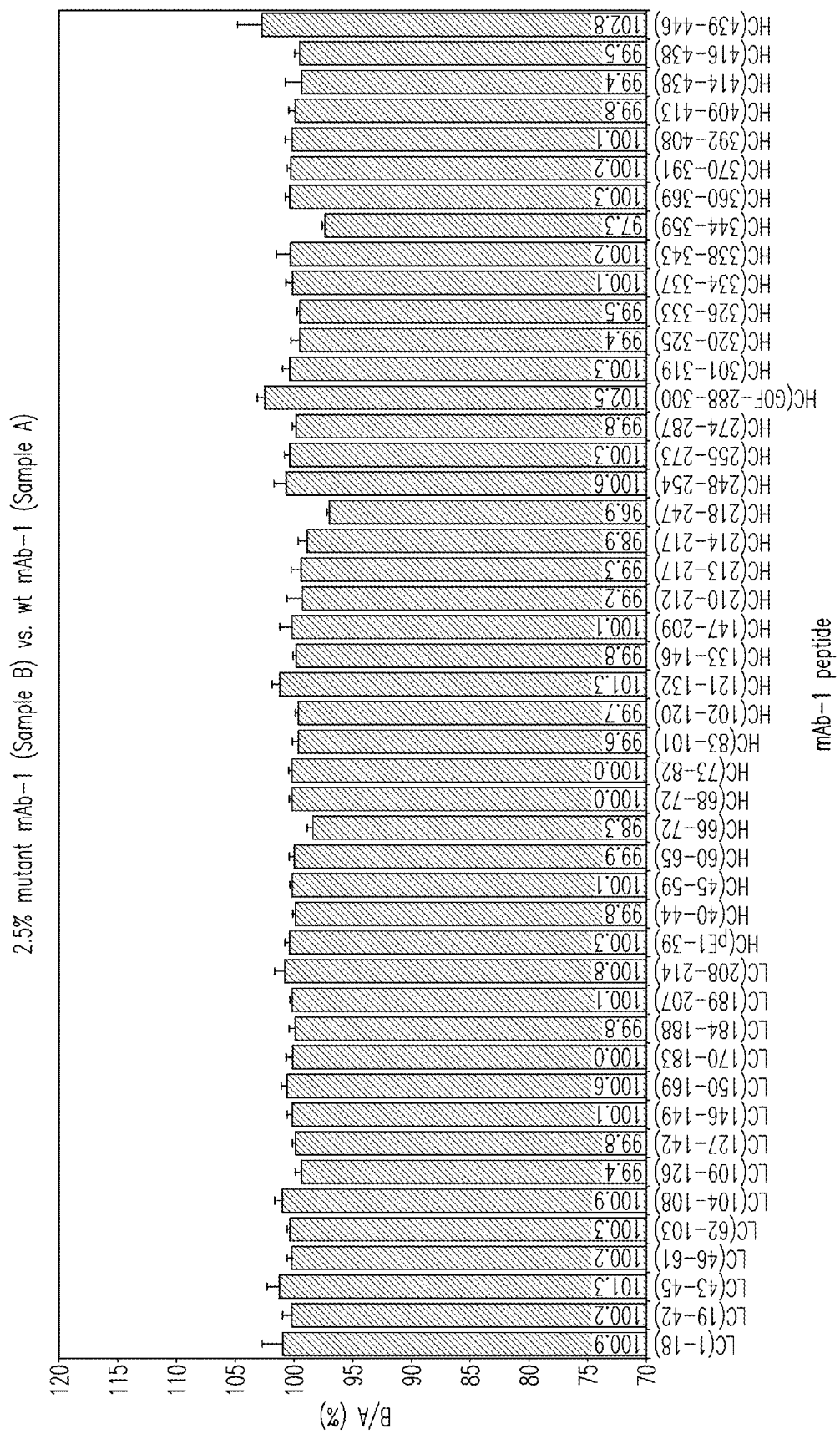

FIG. 12 is a SITRS bar graph for the SITRS experiment in which wt mAb-1 was compared to mAb-1 that was spiked with mutant to 2.5% in accordance with the present analysis.

Figure 13:
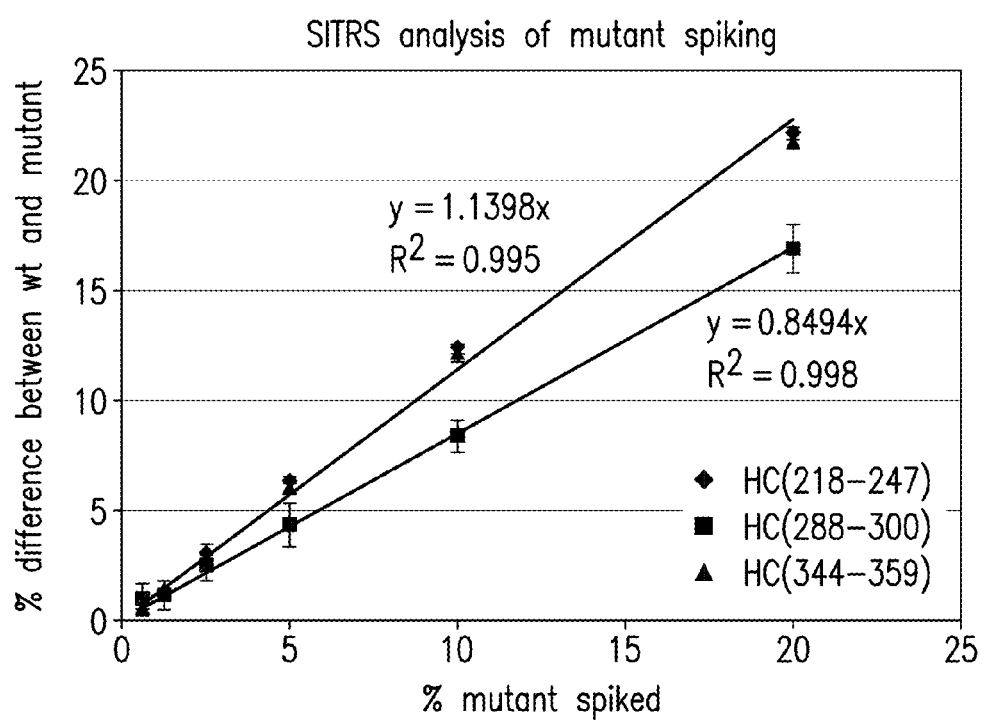

FIG. 13 is a plot of the amounts of peptides HC(218-247), HC(344-359) and HC(288-300) in the mutant-spiked antibody relative to that of the wild-type antibody as measured by the SITRS analysis of various mutant-spiked mAb-1 samples in accordance with the present analysis.

FIG. 14 is a SITRS bar graph for the comparison of batches of MAb-1 samples produced by two different cell lines using two different processes (CHO-produced (FIG. 14A) and HEK-produced (FIG. 14B)) in accordance with the present analysis.

Figure 14A:
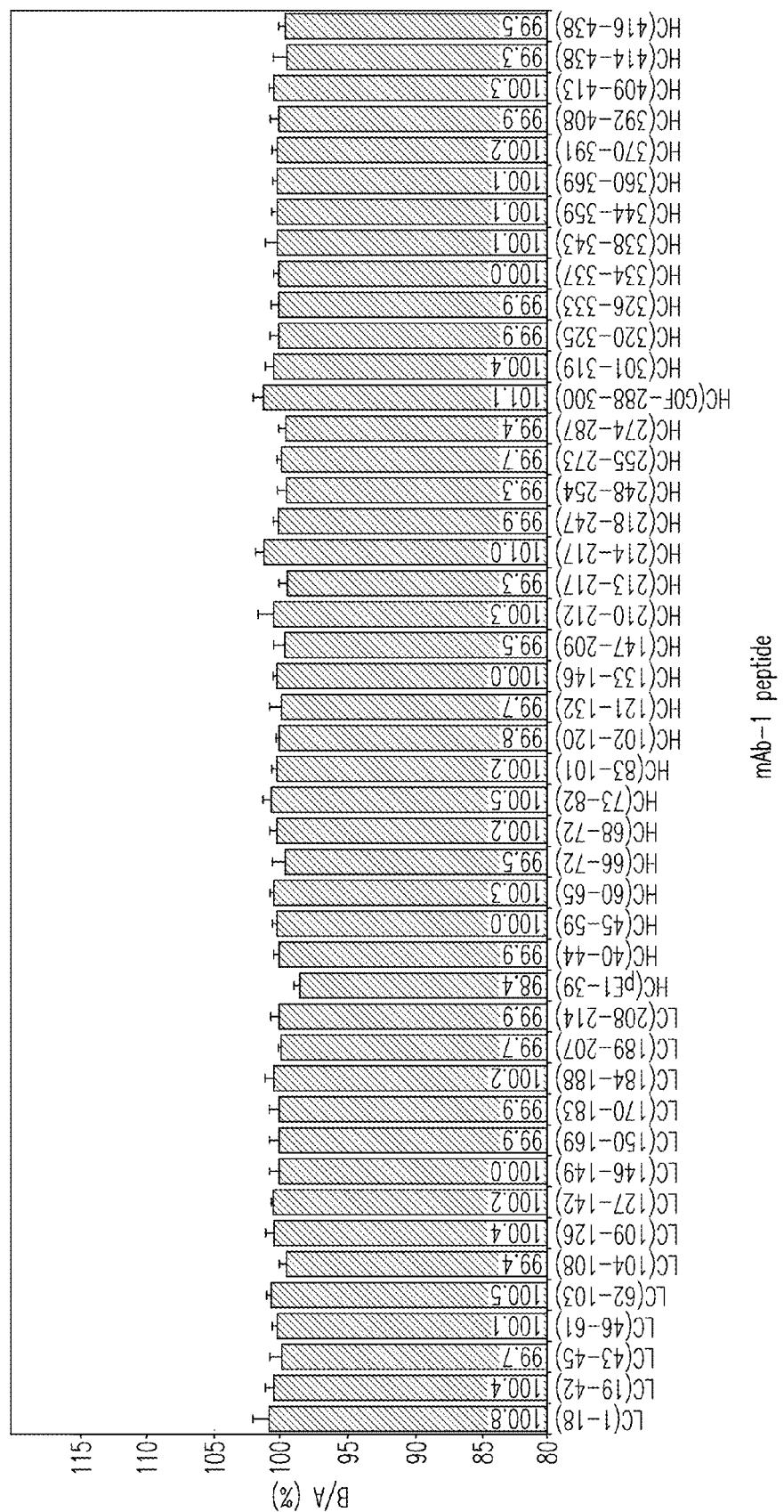
Figure 14A:
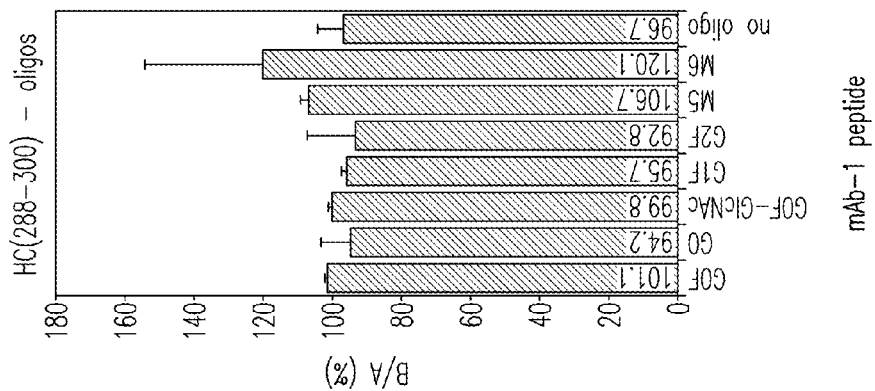
Figure 14A:
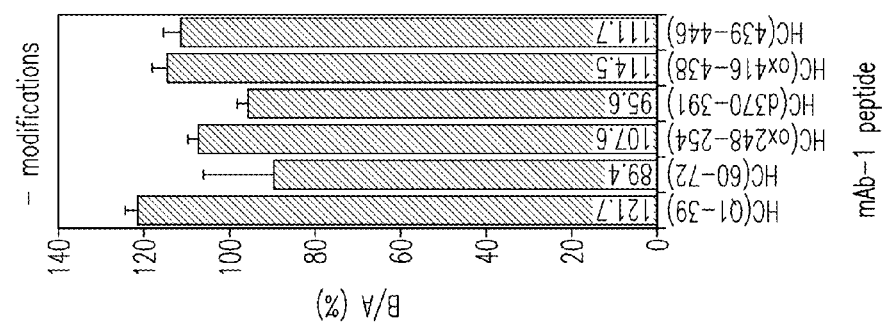
Figure 14B:
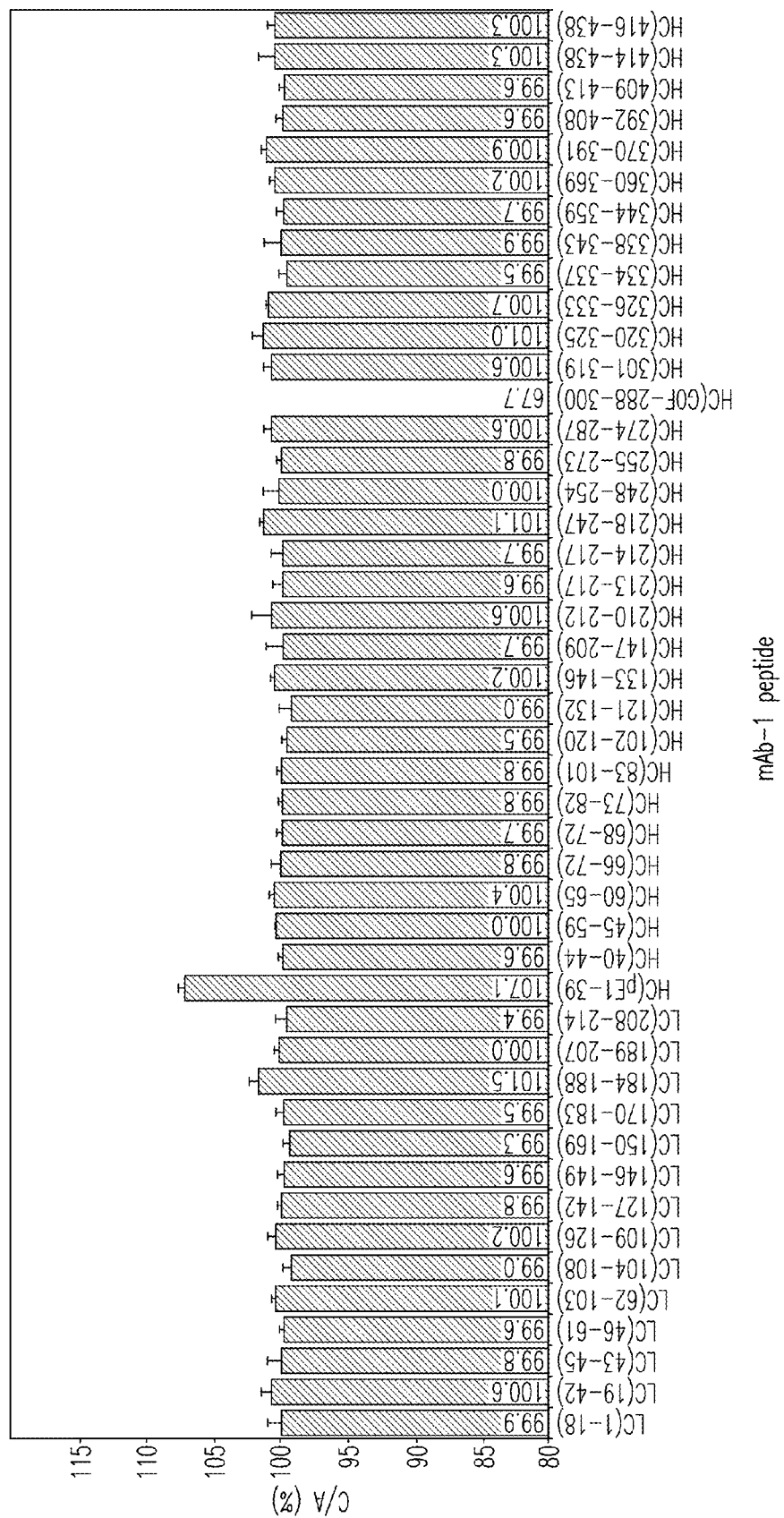
Figure 14B:
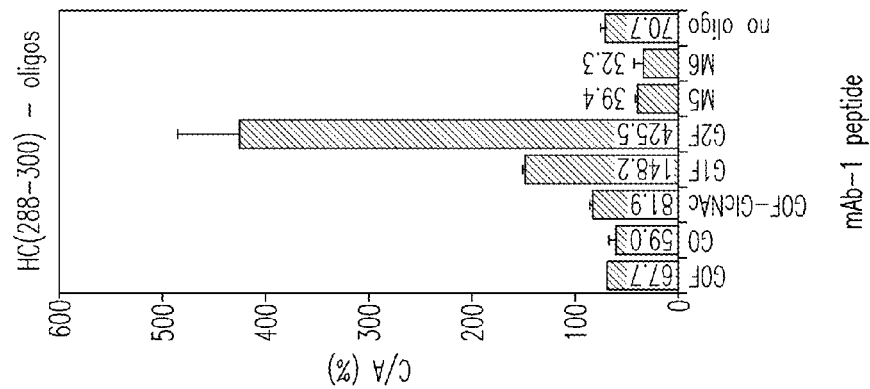
Figure 14B:
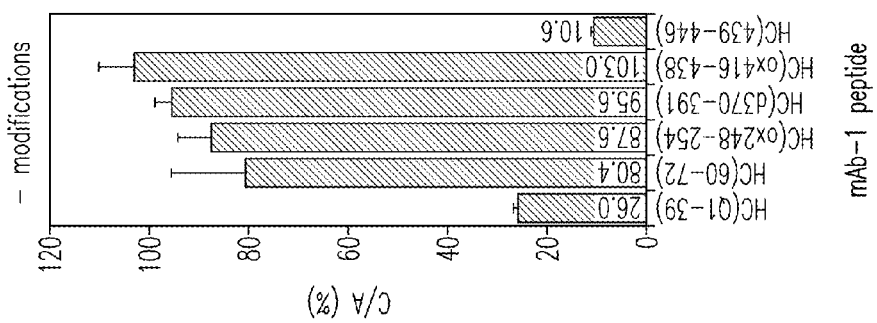

FIG. 15 is table of stable isotope-tagged reference standard (SITRS) results presented in FIG. 14B with conventional analyses in accordance with the present analysis. Selected results of the SITRS analysis (n=6) of mAb-1 from batch 2 (CHO-produced) and batch 3 (HEK-produced) are compared to the results obtained by conventional methods (n=3).

Figure 16:
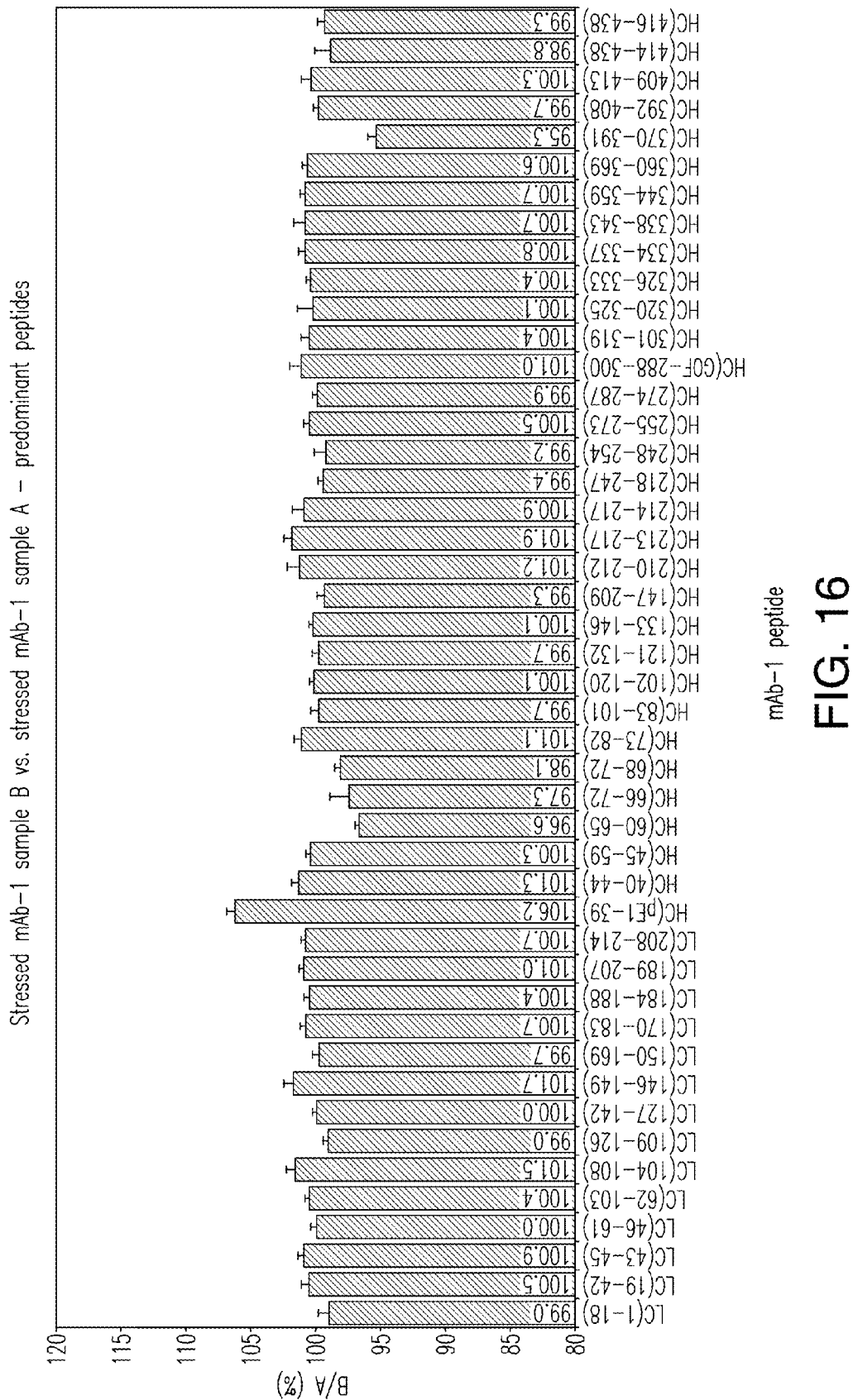
Figure 16:
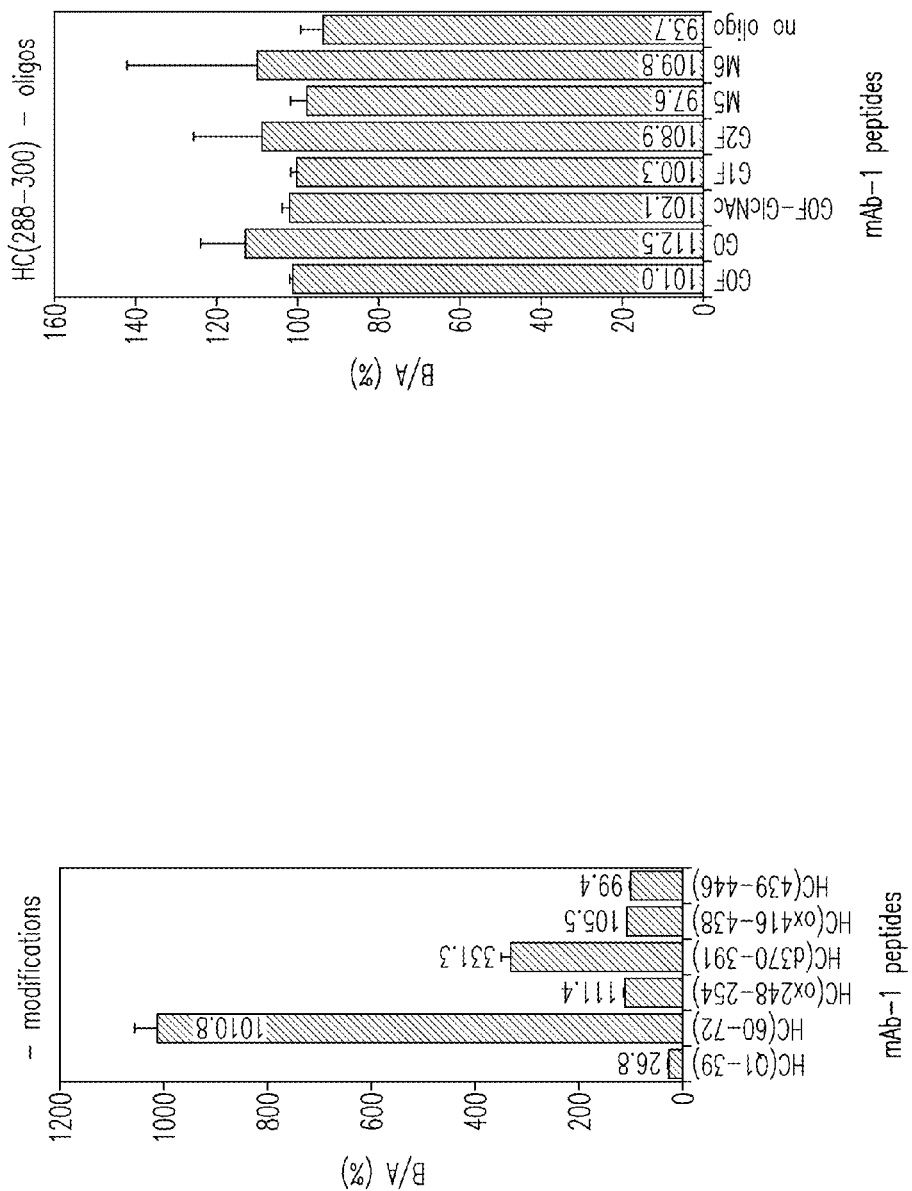

FIG. 16 is a SITRS bar graph for the comparison of mAb-1 samples mildly stressed in two different formulation buffers in accordance with the present analysis.

Figure 17:
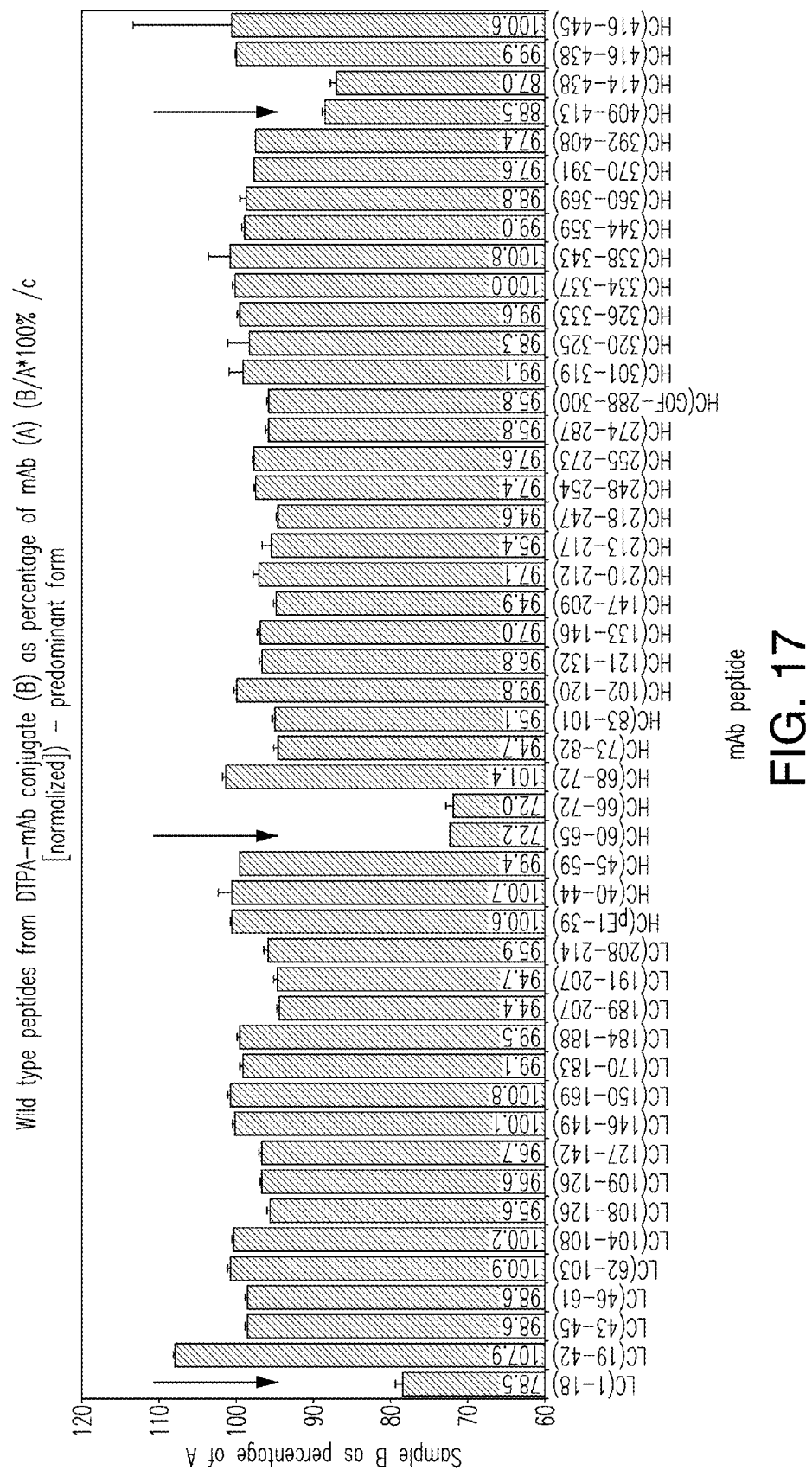
Figure 17:
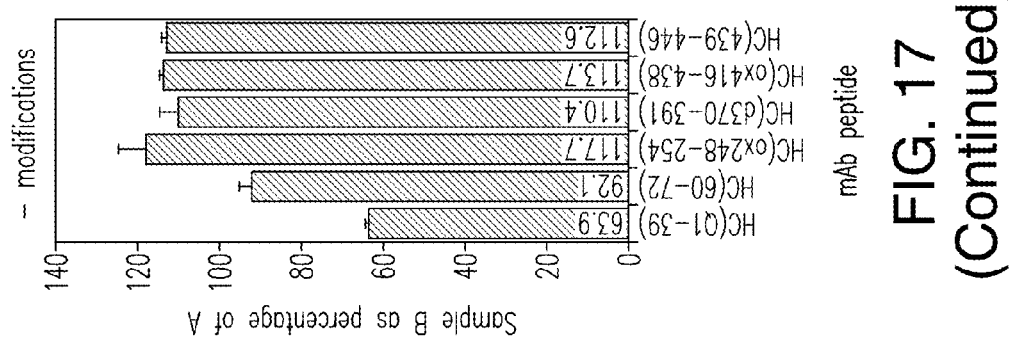

FIG. 17 is a SITRS bar graph for the comparison of DTPA-MAb-1 conjugate to unmodified MAb-1 in accordance with the present analysis.

Figure 18:
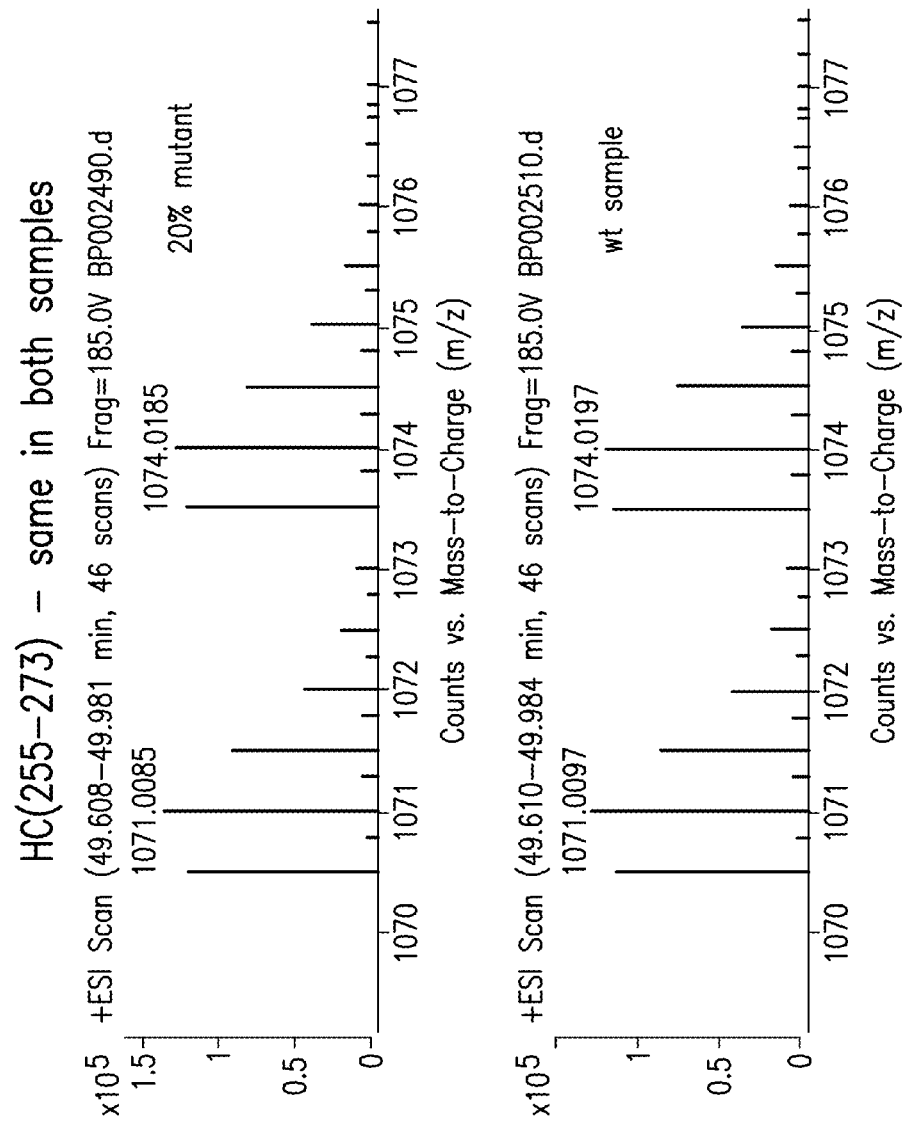

FIG. 18 is an extracted ion mass spectra for a SITRS experiment in which wt mAb-1 was compared to mAb-1 that was spiked with mutant to 20% (the wt HC(255-273) peptide that is present in both wt and mutant mAb is shown) in accordance with the present analysis.

Figure 3:
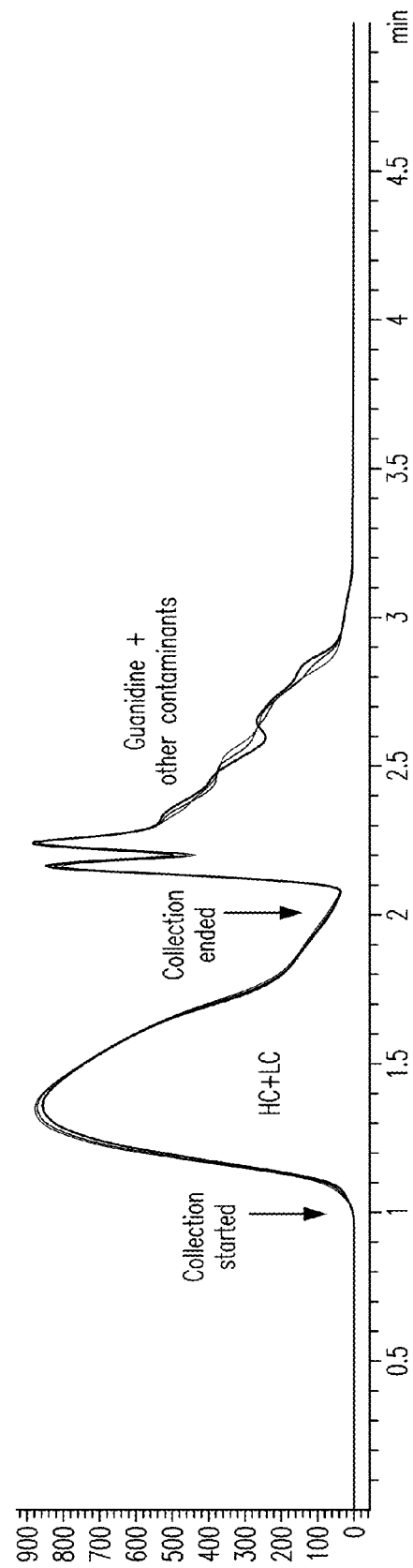

FIG. 19 is a table of monoisotopic peak intensities for HC(255-273) from FIG. 3 in accordance with the present analysis.

Figure 20:
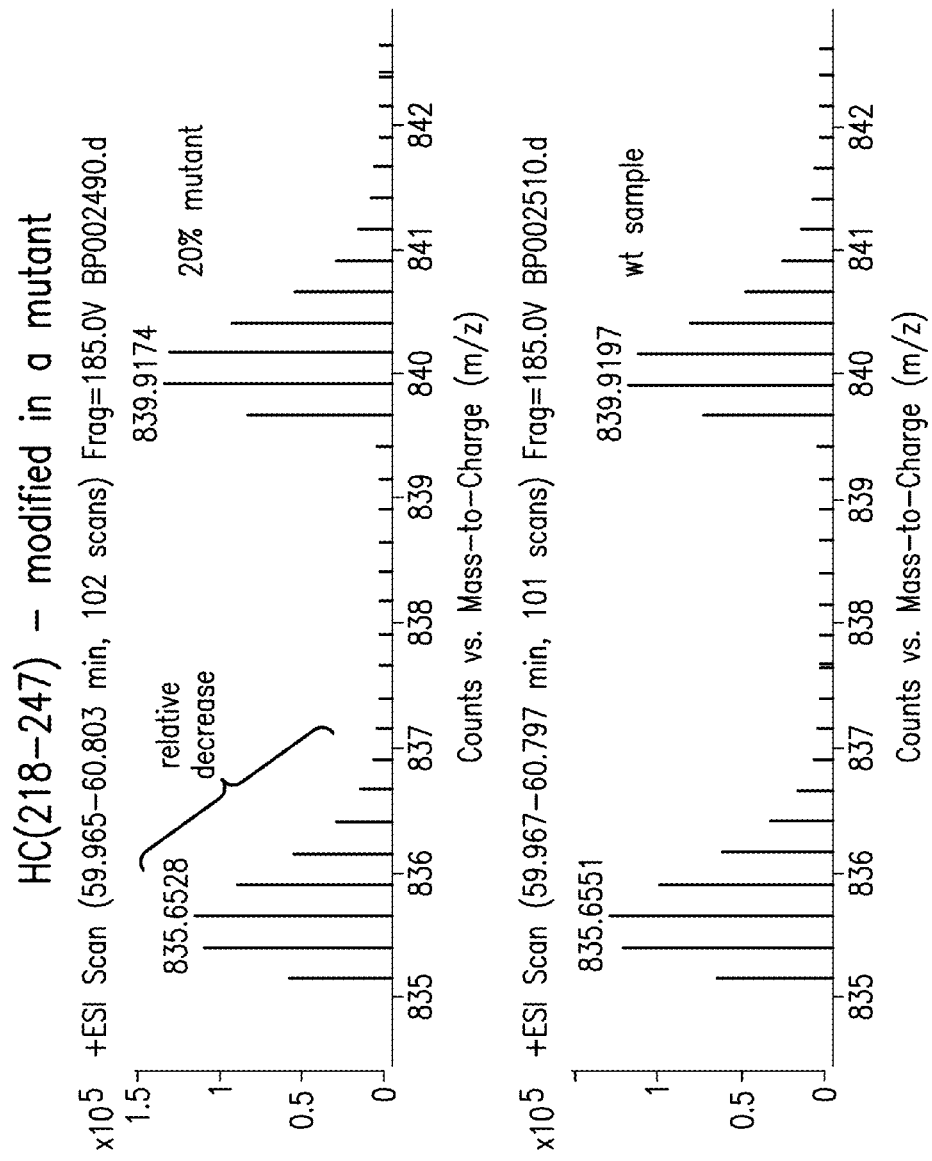

FIG. 20 is an extracted ion mass spectra for the SITRS experiment in which wt mAb-1 was compared to mAb-1 that was spiked with mutant to 20% (the wt HC(218-247) peptide that is modified in the mutant mAb is shown) in accordance with the present analysis.

FIG. 21 is a table of monoisotopic peak intensities for HC(218-247) from FIG. 20 in accordance with the present analysis.

Figure 22:
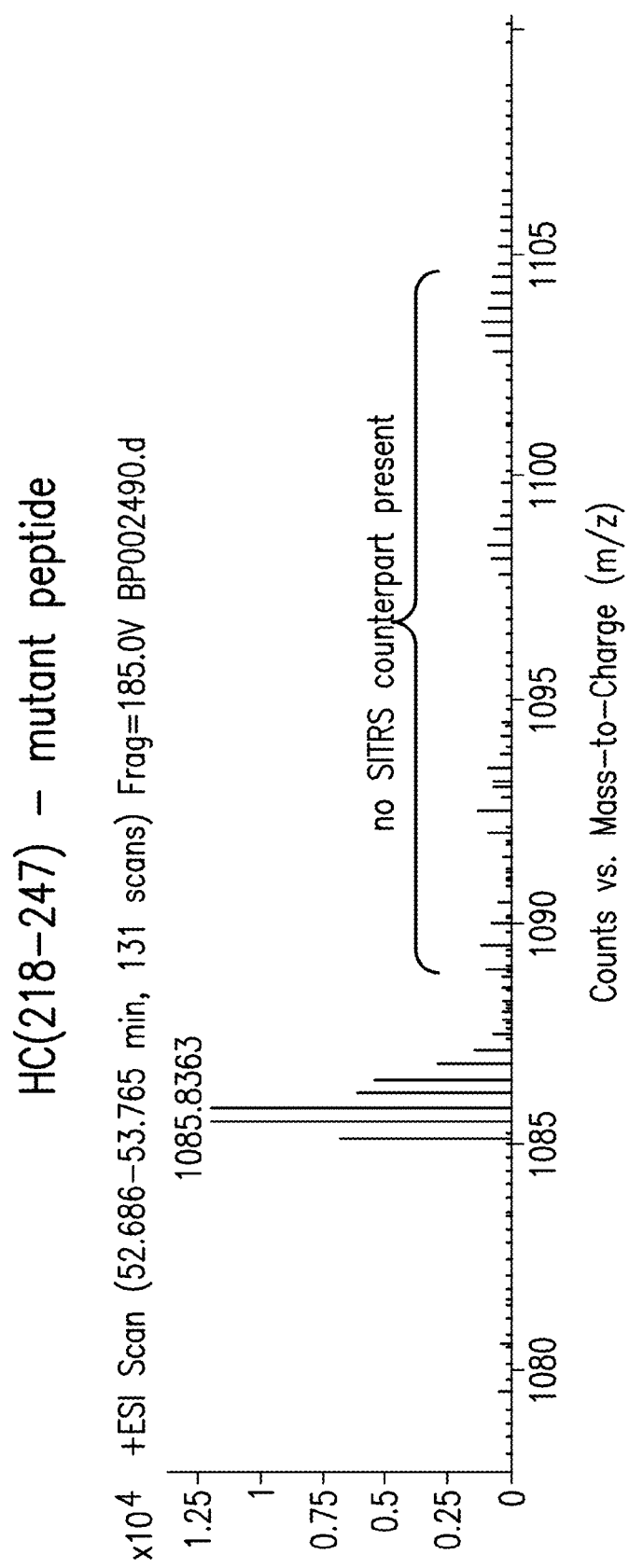

FIG. 22 is an extracted ion mass spectra for the SITRS experiment in which wt mAb-1 was compared to mAb-1 that was spiked with mutant to 20% (the mutated HC(218-247) peptide that is only present in the mutant mAb, and absent from the SITRS sample is shown) in accordance with the present analysis.

SEQUENCE LISTING

The specification further incorporates by reference the Sequence Listing submitted herewith via EFS on Jun. 6, 2012. Pursuant to 37 C.F.R. §1.52(e)(5), the Sequence Listing text file, identified as 0031681368SeqList.txt is 13,638 bytes and was created on Jun. 6, 2012. The Sequence Listing, electronically filed herewith, does not extend beyond the scope of the specification and thus not contain new matter.

5. DETAILED DESCRIPTION OF THE INVENTION

The present invention relates to methods for analyzing protein samples, e.g., monoclonal antibodies, via the SITRS technique, as well as methods and systems that facilitate the processing of data generated by the SITRS technique.

5.1. Definitions

As used in the specification and the appended claims, the singular forms "a," "an" and "the" include plural referents unless the context clearly dictates otherwise. Thus, for example, reference to "a compound" can include mixtures of compounds.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, or up to 10%, or up to 5%, or up to 1% of a given value. Alternatively, particularly with respect to biological systems or processes, the term can mean within an order of magnitude, or within 5-fold, or within 2-fold, of a value.

As used herein, the term "SITRS protein standard" or "SITRS standard" means a protein, having a known sequence, labeled with a stable isotopically labeled variant of at least one amino acid present in the protein. The SITRS protein standard can be identical in sequence to that of the protein of interest or it can be a variant of the protein of interest, e.g., a polypeptide that has a mutation, such as a deletion, insertion, and/or substitution of one or more amino acids, or it can be a unrelated protein sharing at least sequence of two or more amino acids in common with the protein of interest. The SITRS standard can be prepared using methods known in the art in which heavy amino acids are used in place of standard amino acids. For example, but not by way of limitation, when preparing a protein that includes arginine and lysine residues, the growth media may include arginine and lysine residues composed of six $^{13}$C atoms instead of the naturally abundant $^{12}$C atoms (Arginine-6 and Lysine-6).

The term "antibody" includes an immunoglobulin molecule comprised of four polypeptide chains, two heavy (H) chains and two light (L) chains inter-connected by disulfide bonds. Each heavy chain is comprised of a heavy chain variable region (abbreviated herein as HCVR or VH) and a heavy chain constant region (CH). The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDRs), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4.

In certain embodiments, an antibody can be a human, a chimeric, or a humanized antibody. Chimeric or humanized antibodies of the present disclosure can be prepared based on the sequence of a non-human monoclonal antibody prepared as described above. DNA encoding the heavy and light chain immunoglobulins can be obtained from the non-human hybridoma of interest and engineered to contain non-murine (e.g., human) immunoglobulin sequences using standard molecular biology techniques. For example, to create a chimeric antibody, murine variable regions can be linked to human constant regions using methods known in the art (see e.g., U.S. Pat. No. 4,816,567 to Cabilly et al.). To create a humanized antibody, murine CDR regions can be inserted into a human framework using methods known in the art (see e.g., U.S. Pat. No. 5,225,539 to Winter, and U.S. Pat. Nos. 5,530,101; 5,585,089; 5,693,762 and 6,180,370 to Queen et al.

The term "antigen-binding portion" of an antibody (or "antibody portion") includes fragments of an antibody that retain the ability to specifically bind to an antigen. It has been shown that the antigen-binding function of an antibody can be performed by fragments of a full-length antibody. Examples of binding fragments encompassed within the term "antigen-binding portion" of an antibody include (i) a Fab fragment, a monovalent fragment comprising the VL, VH, CL and CH1 domains; (ii) a F(ab')2 fragment, a bivalent fragment comprising two Fab fragments linked by a disulfide bridge at the hinge region; (iii) a Fd fragment comprising the VH and CH1 domains; (iv) a Fv fragment comprising the VL and VH domains of a single arm of an antibody, (v) a dAb fragment (Ward et al., (1989) Nature 341:544-546, the entire teaching of which is incorporated herein by reference), which comprises a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see, e.g., Bird et al. (1988) Science 242:423-426; and Huston et al. (1988) Proc. Natl. Acad. Sci. USA 85:5879-5883, the entire teachings of which are incorporated herein by reference). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see, e.g., Holliger, P., et al. (1993) Proc. Natl. Acad. Sci. USA 90:6444-6448; Poljak, R. J., et al. (1994) Structure 2:1121-1123, the entire teachings of which are incorporated herein by reference). Still further, an antibody or antigen-binding portion thereof may be part of a larger immunoadhesion molecule, formed by covalent or non-covalent association of the antibody or antibody portion with one or more other proteins or peptides. Examples of such immunoadhesion molecules include use of the streptavidin core region to make a tetrameric scFv molecule (Kipriyanov, S. M., et al. (1995) Human Antibodies and Hybridomas 6:93-101, the entire teaching of which is incorporated herein by reference) and use of a cysteine residue, a marker peptide and a C-terminal polyhistidine tag to make bivalent and biotinylated scFv molecules (Kipriyanov, S. M., et al. (1994) Mol. Immunol. 31:1047-1058, the entire teaching of which is incorporated herein by reference). Antibody portions, such as Fab and F(ab')2 fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein. In one aspect, the antigen binding portions are complete domains or pairs of complete domains.

The term "human antibody" includes antibodies having variable and constant regions corresponding to human germline immunoglobulin sequences as described by Kabat et al. (See Kabat, et al. (1991) Sequences of proteins of Immunological Interest, Fifth Edition, U.S. Department of Health and Human Services, NIH Publication No. 91-3242). The human antibodies of the invention may include amino acid residues not encoded by human germline immunoglobulin sequences (e.g., mutations introduced by random or site-specific mutagenesis in vitro or by somatic mutation in vivo), e.g., in the CDRs and in particular CDR3. The mutations can be introduced using a selective mutagenesis approach. The human antibody can have at least one position replaced with an amino acid residue, e.g., an activity enhancing amino acid residue which is not encoded by the human germline immunoglobulin sequence. The human antibody can have up to twenty positions replaced with amino acid residues which are not part of the human germline immunoglobulin sequence. In other embodiments, up to ten, up to five, up to three or up to two positions are replaced. In one embodiment, these replacements are within the CDR regions. However, the term "human antibody", as used herein, is not intended to include antibodies in which CDR sequences derived from the germline of another mammalian species, such as a mouse, have been grafted onto human framework sequences.

The phrase "recombinant human antibody" includes human antibodies that are prepared, expressed, created or isolated by recombinant means, such as antibodies expressed using a recombinant expression vector transfected into a host cell, antibodies isolated from a recombinant, combinatorial human antibody library, antibodies isolated from an animal (e.g., a mouse) that is transgenic for human immunoglobulin genes (see, e.g., Taylor, L. D., et al. (1992) Nucl. Acids Res. 20:6287-6295, the entire teaching of which is incorporated herein by reference) or antibodies prepared, expressed, created or isolated by any other means that involves splicing of human immunoglobulin gene sequences to other DNA sequences. Such recombinant human antibodies have variable and constant regions derived from human germline immunoglobulin sequences (see, Kabat, E. A., et al. (1991) Sequences of Proteins of Immunological Interest, Fifth Edition, U.S. Department of Health and Human Services, NIH Publication No. 91-3242). In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo. In certain embodiments, however, such recombinant antibodies are the result of selective mutagenesis approach or back-mutation or both.

Recombinant human antibodies of the invention can be isolated by screening of a recombinant combinatorial antibody library, e.g., a scFv phage display library, prepared using human VL and VH cDNAs prepared from mRNA derived from human lymphocytes. Methodologies for preparing and screening such libraries are known in the art. In addition to commercially available kits for generating phage display libraries (e.g., the Pharmacia Recombinant Phage Antibody System, catalog no. 27-9400-01; and the Stratagene SurfZAP™ phage display kit, catalog no. 240612, the entire teachings of which are incorporated herein), examples of methods and reagents particularly amenable for use in generating and screening antibody display libraries can be found in, e.g., Ladner et al. U.S. Pat. No. 5,223,409; Kang et al. PCT Publication No. WO 92/18619; Dower et al. PCT Publication No. WO 91/17271; Winter et al. PCT Publication No. WO 92/20791; Markland et al. PCT Publication No. WO 92/15679; Breitling et al. PCT Publication No. WO 93/01288; McCafferty et al. PCT Publication No. WO 92/01047; Garrard et al. PCT Publication No. WO 92/09690; Fuchs et al. (1991) Bio/Technology 9:1370-1372; Hay et al. (1992) Hum Antibod Hybridomas 3:81-85; Huse et al. (1989) Science 246:1275-1281; McCafferty et al., Nature (1990) 348:552-554; Griffiths et al. (1993) EMBO J 12:725-734; Hawkins et al. (1992) J Mol Biol 226:889-896; Clarkson et al. (1991) Nature 352:624-628; Gram et al. (1992) PNAS 89:3576-3580; Garrard et al. (1991) Bio/Technology 9:1373-1377; Hoogenboom et al. (1991) Nuc Acid Res 19:4133-4137; and Barbas et al. (1991) PNAS 88:7978-7982; the entire teachings of which are incorporated herein.

Human monoclonal antibodies of this disclosure can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

An "isolated antibody" includes an antibody that is substantially free of other antibodies having different antigenic specificities (e.g., an isolated antibody that specifically binds a particular target is substantially free of antibodies that specifically bind antigens other than the specified target). An isolated antibody that specifically binds a particular human target may bind the same target from other species. Moreover, an isolated antibody may be substantially free of other cellular material and/or chemical.

The phrase "recombinant host cell" (or simply "host cell") includes a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

"Purified" when referring to a target molecule of interest in a mixture indicates that its relative concentration (weight of target divided by the weight of all components or fractions in the mixture) is increased by at least 20%. In one series of embodiments, the relative concentration is increased by at least about 40%, about 50%, about 60%, about 75%, about 100%, about 150%, or about 200%. A target molecule of interest can also be said to be purified when the relative concentration of components from which it is purified (weight of component or fraction from which it is purified divided by the weight of all components or fractions in the mixture) is decreased by at least about 20%, about 40%, about 50%, about 60%, about 75%, about 85%, about 95%, about 98% or about 100%. In still another series of embodiments, the target molecule of interest is purified to a relative concentration of at least about 50%, about 65%, about 75%, about 85%, about 90%, about 97%, about 98%, or about 99%. When a target molecule of interest in one embodiment is "separated" from other components or fractions, it will be understood that in other embodiments the component or fraction is "purified" at levels provided herein.

"Chromatography", as used herein, refers to analytical techniques used for the separation of target molecules of interest from a mixture of molecules, and relies upon selective attraction among components of the mixture to a solid phase. Examples include affinity chromatography, ion exchange chromatography, size exclusion chromatography, and hydrophobic interaction chromatography.

5.2. The SITRS Technique

The SITRS technique involves, in certain embodiments, the following four steps: (1) protein sample production; (2) protein sample purification; (3) comparison of protein samples using LC-MS; and (4) analysis of resulting MS spectra data. Non-limiting examples of methods and compositions for accomplishing the above-described steps are outlined in detail in the following sections.

5.2.1. Protein Production

In certain embodiments, the present invention relates to the use of the SITRS technique to compare samples of a protein of interest and analysis of data generated by such comparisons. In certain embodiments, the protein of interest is an antibody or a portion thereof. In certain embodiments, the protein of interest is produced using recombinant DNA technology.

Although specifically directed to the production of antibodies, the following description outlines general techniques that can be adapted for the recombinant production of other proteins. To express a recombinant antibody, DNAs encoding partial or full-length light and heavy chains are inserted into one or more expression vector such that the genes are operatively linked to transcriptional and translational control sequences. (See, e.g., U.S. Pat. No. 6,914,128, the entire teaching of which is incorporated herein by reference.) In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into a separate vector or, more typically, both genes are inserted into the same expression vector. The antibody genes are inserted into an expression vector by standard methods (e.g., ligation of complementary restriction sites on the antibody gene fragment and vector, or blunt end ligation if no restriction sites are present). Prior to insertion of the antibody or antibody-related light or heavy chain sequences, the expression vector may already carry antibody constant region sequences. For example, one approach to converting particular VH and VL sequences to full-length antibody genes is to insert them into expression vectors already encoding heavy chain constant and light chain constant regions, respectively, such that the VH segment is operatively linked to the CH segment(s) within the vector and the VL segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, a recombinant expression vector of the invention can carry one or more regulatory sequence that controls the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, e.g., in Goeddel; Gene Expression Technology: Methods in Enzymology 185, Academic Press, San Diego, Calif. (1990), the entire teaching of which is incorporated herein by reference. It will be appreciated by those skilled in the art that the design of the expression vector, including the selection of regulatory sequences may depend on such factors as the choice of the host cell to be transformed, the level of expression of protein desired, etc. Suitable regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. For further description of viral regulatory elements, and sequences thereof, see, e.g., U.S. Pat. No. 5,168,062 by Stinski, U.S. Pat. No. 4,510,245 by Bell et al. and U.S. Pat. No. 4,968,615 by Schaffner et al., the entire teachings of which are incorporated herein by reference.

In addition to the antibody chain genes and regulatory sequences, a recombinant expression vector of the invention may carry one or more additional sequences, such as a sequence that regulates replication of the vector in host cells (e.g., origins of replication) and/or a selectable marker gene. The selectable marker gene facilitates selection of host cells into which the vector has been introduced (see e.g., U.S. Pat. Nos. 4,399,216, 4,634,665 and 5,179,017, all by Axel et al., the entire teachings of which are incorporated herein by reference). For example, typically the selectable marker gene confers resistance to drugs, such as G418, hygromycin or methotrexate, on a host cell into which the vector has been introduced. Suitable selectable marker genes include the dihydrofolate reductase (DHFR) gene (for use in dhfr-host cells with methotrexate selection/amplification) and the neo gene (for G418 selection).

An antibody, or antibody portion, of the invention can be prepared by recombinant expression of immunoglobulin light and heavy chain genes in a host cell. To express an antibody recombinantly, a host cell is transfected with one or more recombinant expression vectors carrying DNA fragments encoding the immunoglobulin light and heavy chains of the antibody such that the light and heavy chains are expressed in the host cell and secreted into the medium in which the host cells are cultured, from which medium the antibodies can be recovered. Standard recombinant DNA methodologies are used to obtain antibody heavy and light chain genes, incorporate these genes into recombinant expression vectors and introduce the vectors into host cells, such as those described in Sambrook, Fritsch and Maniatis (eds), Molecular Cloning; A Laboratory Manual, Second Edition, Cold Spring Harbor, N.Y., (1989), Ausubel et al. (eds.) Current Protocols in Molecular Biology, Greene Publishing Associates, (1989) and in U.S. Pat. Nos. 4,816,397 & 6,914,128, the entire teachings of which are incorporated herein.

For expression of the light and heavy chains, the expression vector(s) encoding the heavy and light chains is (are) transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, such as mammalian host cells, is suitable because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss and Wood (1985) Immunology Today 6:12-13, the entire teaching of which is incorporated herein by reference).

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, e.g., Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as Bacilli such as *B. subtilis* and *B. licheniformis* (e.g., *B. licheniformis* 41P disclosed in DD 266,710 published Apr. 12, 1989), *Pseudomonas* such as *P. aeruginosa*, and *Streptomyces*. One suitable *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for polypeptide encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e.g., *K. lactis*, *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K.*

*marxianus; yarrowia* (EP 402,226); *Pichia pastoris* (EP 183,070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium,* and *Aspergillus* hosts such as *A. nidulans* and *A. niger.*

Suitable host cells for the expression of glycosylated antibodies are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, petunia, tomato, and tobacco can also be utilized as hosts.

Suitable mammalian host cells for expressing the recombinant antibodies of the invention include Chinese Hamster Ovary (CHO cells) (including dhfr-CHO cells, described in Urlaub and Chasin, (1980) PNAS USA 77:4216-4220, used with a DHFR selectable marker, e.g., as described in Kaufman and Sharp (1982) Mol. Biol. 159:601-621, the entire teachings of which are incorporated herein by reference), NS0 myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or secretion of the antibody into the culture medium in which the host cells are grown. Other examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Viral. 36:59 (1977)); baby hamster kidney cells (BHK, ATCC CCL 10); Chinese hamster ovary cells/–DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., Annals N.Y. Acad. Sci. 383:44-68 (1982)); MRC 5 cells; FS4 cells; and a human hepatoma line (Hep G2), the entire teachings of which are incorporated herein by reference.

Host cells are transformed with the above-described expression or cloning vectors for antibody production and cultured in conventional nutrient media modified as appropriate for inducing promoters, selecting transformants, or amplifying the genes encoding the desired sequences.

The host cells used to produce an antibody may be cultured in a variety of media. Commercially available media such as HAM'S F10™ (Sigma), MINIMAL ESSENTIAL MEDIUM™ ((MEM), (Sigma), RPMI-1640 (Sigma), and DULBECCO'S MODIFIED EAGLE'S MEDIUM™ ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. No. Re. 30,985 may be used as culture media for the host cells, the entire teachings of which are incorporated herein by reference. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as gentamycin drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Host cells can also be used to produce portions of intact antibodies, such as Fab fragments or scFv molecules. It is understood that variations on the above procedure are within the scope of the present invention. For example, in certain embodiments it may be desirable to transfect a host cell with DNA encoding either the light chain or the heavy chain (but not both) of an antibody of this invention. Recombinant DNA technology may also be used to remove some or all of the DNA encoding either or both of the light and heavy chains that is not necessary for antigen binding. The molecules expressed from such truncated DNA molecules are also encompassed by the antibodies of the invention. In addition, bifunctional antibodies may be produced in which one heavy and one light chain are an antibody of the invention and the other heavy and light chain are specific for an antigen other than the original antigen by crosslinking an antibody of the invention to a second antibody by standard chemical crosslinking methods.

In a suitable system for recombinant expression of an antibody, or antigen-binding portion thereof, of the invention, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium.

When using recombinant techniques, the antibody can be produced intracellularly, in the periplasmic space, or directly secreted into the medium. In one aspect, if the antibody is produced intracellularly, as a first step, the particulate debris, either host cells or lysed cells (e.g., resulting from homogenization), can be removed, e.g., by centrifugation or ultrafiltration. Where the antibody is secreted into the medium, supernatants from such expression systems can be first concentrated using a commercially available protein concentration filter, e.g., an AMICON™ or Millipore PELLICON™ ultrafiltration unit.

Prior to the process of the invention, procedures for purification of antibodies from cell debris initially depend on the site of expression of the antibody. Some antibodies can be secreted directly from the cell into the surrounding growth media; others are made intracellularly. For the latter antibodies, the first step of a purification process typically involves: lysis of the cell, which can be done by a variety of methods, including mechanical shear, osmotic shock, or enzymatic treatments. Such disruption releases the entire contents of the cell into the homogenate, and in addition produces subcellular fragments that are difficult to remove due to their small size. These are generally removed by differential centrifugation or by filtration. Where the antibody is secreted, supernatants from such expression systems are generally first concentrated using a commercially available protein concentration filter, e.g., an AMICON™ or Millipore PELLICON™ ultrafiltration unit. Where the antibody is secreted into the medium, the recombinant host cells can also be separated from the cell culture medium, e.g., by tangential flow filtration. Antibodies can be further recovered from the culture medium using the antibody purification methods of the invention.

In certain embodiments SITRS standard proteins, such as SITRS standard antibodies, are produced such that they include heavy-isotope amino acid variants. Heavy-isotope labeled amino acids variants known in the art are contemplated as useful in accordance with certain embodiments of the present invention and techniques for their incorporation into recombinantly produced proteins are well known Those having skill in the art will recognize that the selection of particular heavy-isotope labeled variants will depend on the protein being formed and the digestion that will be conducted on the protein in preparation for LC-MS detection. For example, when the protein being produced includes arginine and/or lysine and will be subjected to trypsin digest, a heavy arginine and/or lysine can be desirable. Similarly, when the protein being produced includes aspartic acid and will be subjected to endoproteinase AspN digestion, a heavy aspartic acid can be desirable. When the protein being produced includes a glutamic acid and will be subjected to endoproteinase GluC digestion, a heavy glutamic acid can be desirable. When the protein being produced includes a chain of aspartic acid-aspartic acid-aspartic acid-aspartic acid-lysine and will be subjected to enterokinase, light chain digestion, a heavy aspartic acid and/or heavy lysine can be desirable. When the protein being produced includes a chain of isoleucine glutamic acid or aspartic acid-glycine arginine and will be subjected to Factor Xa digestion, a heavy isoleucine, glutamic acid, aspartic acid, glycine, and/or arginine can be desirable. When the protein being produced includes a chain of arginine-X-X arginine and will be subjected to furin digestion, a heavy arginine can be desirable. When the protein being produced includes a histidine tyrosine linkage and will be subjected to genease I digestion, a heavy histidine and/or heavy tyrosine can be desirable. When the protein being produced includes an amino acid having an aromatic and will be subjected to chymotrypsin digestion, a heavy amino acid having an aromatic side chain can be desirable. When the protein being produced includes a lysine and will be subjected to Lys-C or Lys-N digestion, a heavy lysine can be desirable. When the protein being produced includes a methionine and will be subjected to CNBr digestion, a heavy methionine can be desirable. When the protein being produced includes an arginine and will be subjected to endoproteinase ArgC digestion, a heavy arginine can be desirable. The invention is not intended to be limited to particular isotopically labeled variants or particular methods of protein digestion and the isotopically labeled variants and methods can be varied depending on the protein.

5.2.2. Protein Purification

The invention provides a method for producing a purified (or "HCP-reduced") protein preparation from a mixture comprising a protein of interest and at least one HCP. The purification process of the invention begins at the separation step when the protein of interest has been produced using methods described above and conventional methods in the art. Table 1 summarizes one embodiment of a purification scheme. Variations of this scheme can be employed based on the characteristics of the protein of interest, including, but not limited to, adding and/or deleting particular purification steps.

TABLE 1

Purification steps with their associated purpose

| Purification step | Purpose |
| --- | --- |
| Primary recovery | clarification of sample matrix |
| Affinity chromatography | protein capture, host cell protein and associated impurity reduction |
| Low pH incubation | viral reduction/inactivation |
| Anion exchange chromatography | protein capture, host cell protein and associated impurity reduction |
| Hydrophobic interaction chromatography | reduction of protein aggregates and host cell proteins |
| Viral filtration | removal of large viruses, if present |
| ultrafiltration/diafiltration | concentration and buffer exchange |
| Final filtration | concentration of protein |

Once a clarified solution or mixture comprising the protein of interest has been obtained, separation of the protein from the other proteins produced by the cell, such as HCPs, is performed using a combination of different purification techniques, including affinity separation steps(s), ion exchange separation step(s), and hydrophobic interaction separation step(s). The separation steps separate mixtures of proteins on the basis of their binding characteristics, charge, degree of hydrophobicity, or size. In one aspect of the invention, separation is performed using chromatography, including affinity, cationic, anionic, and hydrophobic interaction. Several different chromatography resins are available for each of these techniques, allowing accurate tailoring of the purification scheme to the particular protein involved. The essence of each of the separation methods is that proteins can be caused either to traverse at different rates down a column, achieving a physical separation that increases as they pass further down the column, or to adhere selectively to the separation medium, being then differentially eluted by different solvents. In some cases, the antibody is separated from impurities when the impurities specifically adhere to the column and the protein of interest does not, i.e., the protein of interest is present in the flow through.

As noted above, accurate tailoring of a purification scheme relies on consideration of the protein to be purified. In certain embodiments, the separation steps of the instant invention are employed to separate an antibody from one or more HCPs. While the present invention is directed to protein purification generally, it can be specifically adapted to the purification of antibodies. For example, antibodies that can be successfully purified using the methods described herein include, but are not limited to, human $IgA_1$, $IgA_2$, IgD, IgE, $IgG_1$, $IgG_2$, $IgG_3$, $IgG_4$, and IgM antibodies. In certain embodiments, the purification strategies of the instant invention exclude the use of Protein A affinity chromatography, for example in the context of the purification of $IgG_3$ antibodies, as $IgG_3$ antibodies bind to Protein A inefficiently. Other factors that allow for specific tailoring of a purification scheme include, but are not limited to: the presence or absence of an Fc region (e.g., in the context of full length antibody as compared to an Fab fragment thereof) because Protein A binds to the Fc region; the particular germline sequences employed in generating to antibody of interest; and the amino acid composition of the antibody (e.g., the primary sequence of the antibody as well as the overall charge/hydrophobicity of the molecule). Antibodies sharing one or more characteristic can be purified using purification strategies tailored to take advantage of that characteristic.

5.2.3. Comparison of Protein Samples Using SITRS

In certain embodiments, the present invention relates to methods for qualitatively and/or quantitatively detecting the presence of mutations, modifications, or polypeptide impurities in one or more protein samples.

In one exemplary qualitative method, a SITRS standard protein corresponding to the protein of interest is prepared such that it includes at least one amino acid that has been replaced with an isotopically-labeled variant. The SITRS standard protein is mixed with a sample of unlabeled protein of interest and the mixture is subjected to digestion and subsequent analysis by bottom-up LC-MS. The resulting MS spectra of the various peptides produced from the digested mixture are analyzed to determine whether one or more doublets indicative of the presence of both the labeled and unlabeled peptide(s) are present. If a doublet peak is not observed, then a single peak may be the result of one of the following possibilities: (1) the peptide fragment derived from the SITRS protein standard does not contain a labeled amino acid; (2) the peptide contains a modification; (3) the peptide contains a mutation; or (4) the peptide corresponds to a polypeptide impurity. Single peaks can then be re-analyzed by tandem mass spectroscopy (MS/MS) to reveal the sequence of the particular peptide and thereby qualitatively determining which of the four possibilities occurred.

In certain embodiments, the present invention relates to methods for comparing two samples of protein and analyzing the data resulting from such comparisons to qualitatively and/or quantitatively identify differences, such as the presence of mutations, modifications, or polypeptide impurities, in the samples. In certain embodiments, the comparison be conducted by utilizing a SITRS protein standard sample mixed with an unlabeled protein prior to protein digestion and LC-MS.

In some embodiments, it may be desirable to denature the mixed sample prior to protein digestion. The denaturation step may be conducted by methods known in the art. Additionally, the denaturants may be removed with the use of Size Exclusion Chromatography High Performance liquid Chromatography (SEC-HPLC). In certain embodiments that employ the SEC HPLC method, flow-rate may be controlled, the ultra-violet (UV) signal may be monitored, and the fraction collection may be timed to collect only the purified antibody and not any residual buffer or other contaminants from the growth process or sample treatment. Additional aspects of sample purification are outlined below.

In certain embodiments, RP-HPLC is employed as the LC step prior to MS analysis. In certain embodiments standard LC conditions are employed, such as, but not limited to, standard RP-HPLC conditions. Examples of standard LC conditions, including, but not limited to, standard RP-HPLC conditions, are well known in the art including, for example, but not by way of limitation, the conditions described in Snyder et al., Introduction to Modern Liquid Chromatography, 3rd Edition, Wiley, (2010). Under standard RP-HPLC conditions, labeled and unlabeled peptides have nearly identical retention times and, therefore, migrate together. While potentially not resolvable by chromatography, the labeled and unlabeled peptides are distinguishable by MS detection, yielding differences in Daltons (Da) equivalent to the number of labeled residues in the particular peptide. Accordingly, when the SITRS protein standard is mixed with an unlabeled protein of interest, doublets indicating a difference in Da will appear in the mass spectra, indicating incorporation of the labeled amino acids into the SITRS protein standard, and the presence of the peptide with the same amino acid sequence in both the SITRS and the unlabeled protein of interest. A SITRS protein reference in which the only difference from its unlabeled counterpart (in a 1:1 mix) is the presence of the labeled amino acids will produce doublets in which each peak has an identical intensity.

In certain embodiments, the measurements achieved by the present invention take into account not only the masses of peptides generated during proteolytic digest, but also the abundance of each resulting peptide. Measuring of the abundance of peptides by MS is enabled by utilizing a SITRS protein reference that is mixed with an unlabeled protein of interest, for example, but not limited to, an antibody, prior to protein digest. By measuring the abundance of peptides, quantitative analysis of the peptides produced in the course to the SITRS technique can be accomplished. Additional unlabeled samples of the protein of interest can be quantitatively compared by first comparing to the same SITRS protein standard as described above, and then comparing the results of those comparisons between the two or more unlabeled protein samples.

In certain embodiments, introduction of a SITRS protein standard as an internal reference standard mitigates variation and artifacts from sample handling and MS detection that may affect quantitation. Examples of potential variations mitigated in accordance with the present invention include extent of protein digestion, formation of artifacts due to sample handling and/or variations in the ionization efficiency during MS detection. By utilizing the present method, such parameters may be normalized with respect to the SITRS protein standard.

In certain embodiments, the comparison of protein samples is used to determine whether an experimental growth media or cell line/clone is acceptable for expressing the protein of interest. In such embodiments, the unlabeled protein is expressed in an experimental growth media or by an experimental cell line/clone. After such expression and, in certain embodiments, subsequent purification, the resulting unlabeled protein sample is mixed with a SITRS protein standard, and the mixed sample is subsequently subjected to protein digestion and bottom-up LC-MS. Analysis of the MS spectra data allows for the identification of qualitative and/or quantitative differences attributable to the experimental growth media or cell line.

In certain embodiments, the comparison of protein samples is used to qualitatively determine mutations, modifications, or polypeptide impurities in the unlabeled protein sample. This qualitative analysis can be used, for example, and not by way of limitation, to determine inefficiencies in a growth media or inefficiencies in a purification process.

Figure 1:
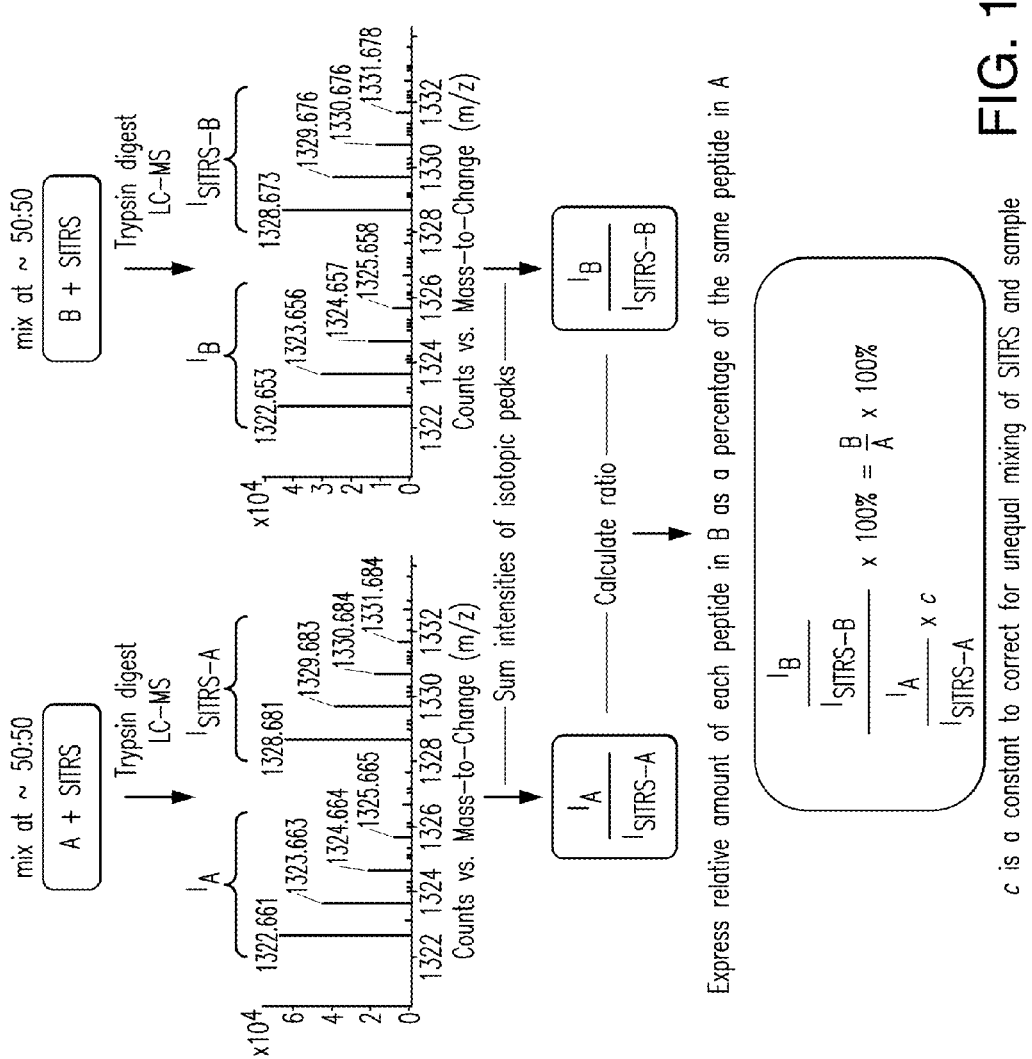
Figure 2A:
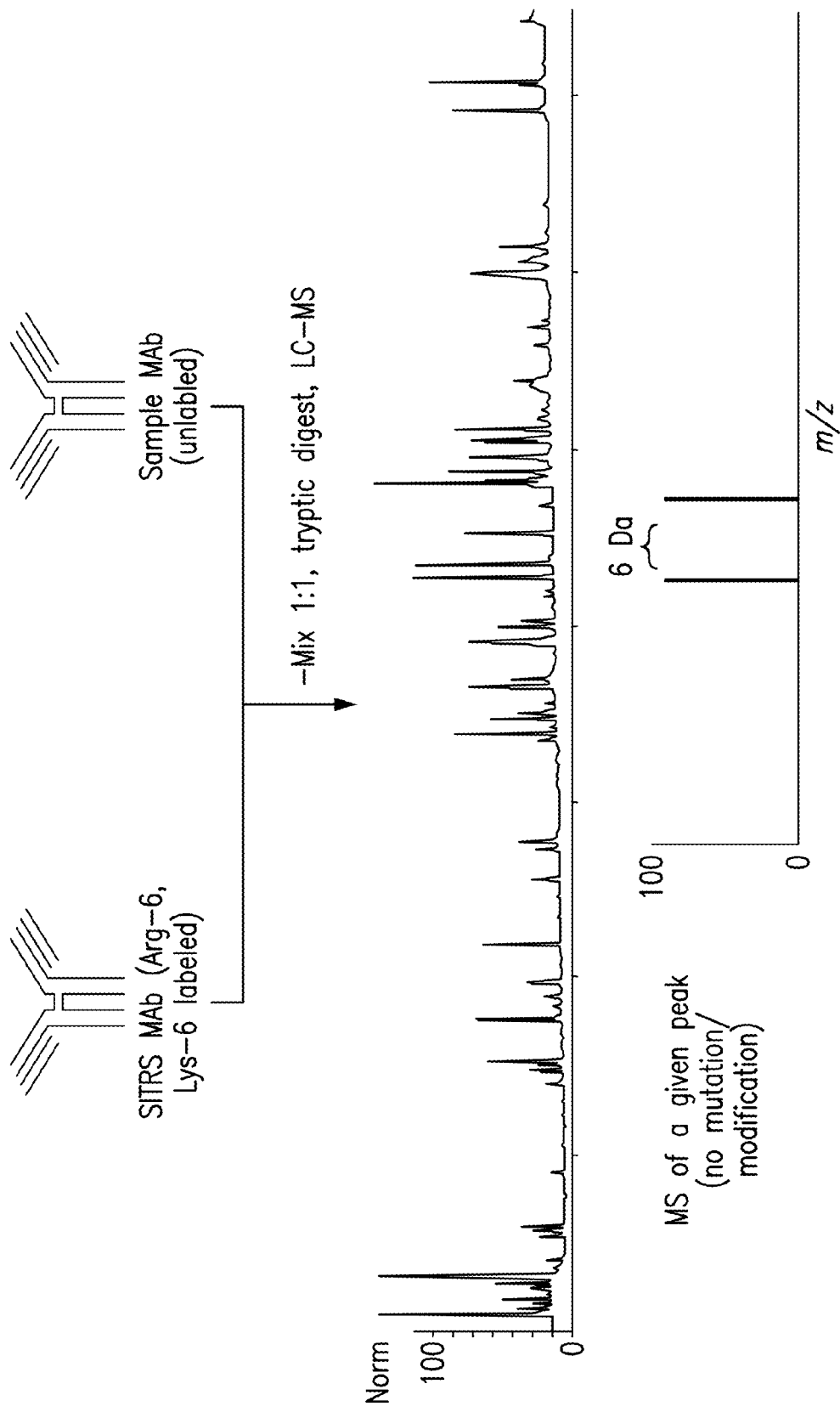

FIG. 1 is a schematic diagram of a SITRS experiment in accordance with the present analysis. FIG. 2A provides a schematic LC-MS analysis of a mixed sample, including an unlabeled MAb and its corresponding SITRS protein standard, which in this non-limiting example contains no modification or mutation. As illustrated in the FIG. 2A, a SITRS protein standard and an unlabeled MAb were mixed in a 1:1 ratio, subjected to protein (tryptic) digest, and then subjected to bottom-up LC-MS. The resulting mass spectra of peptides common to both the unlabeled sample and the SITRS protein standard are unique in that the mass to charge (m/z) peaks appear as doublets, due to the presence of labeled amino acids in the SITRS protein standard. Thus, a peptide that is identical in chemical composition, other than the presence of the unlabeled antibody, to its SITRS protein standard counterpart and is present in the same amount as its SITRS protein standard counterpart will have an intensity that is equal to that of the standard (in a 1:1 mix).

Figure 2B:
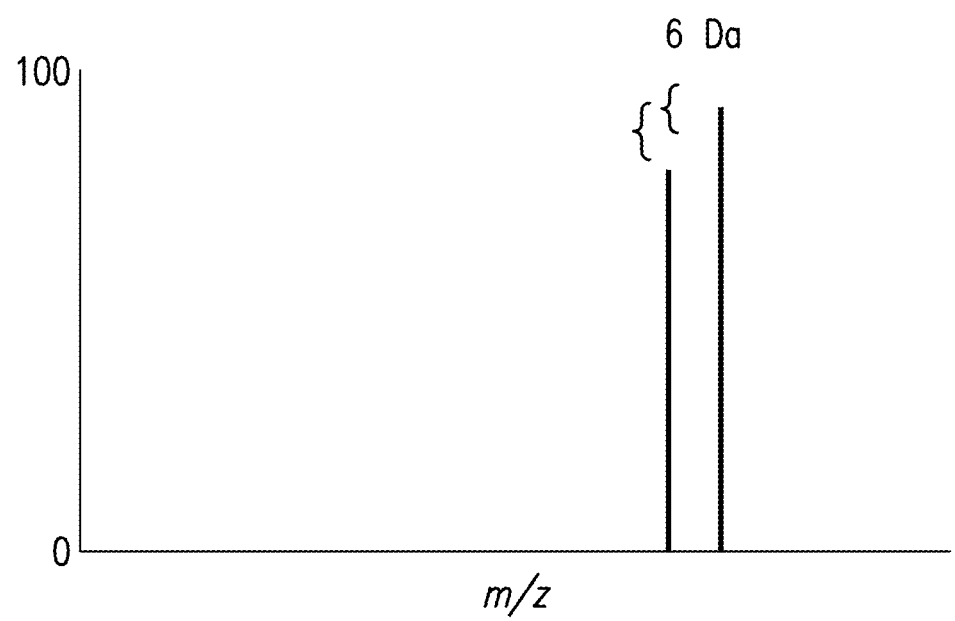

Peptides whose population is partially composed of point mutants or site-specifically modified molecules, such as, for example, deamidation, N-terminal pyroglutamate, or differential glycosylation, will have a mass spectra where the intensity of the peak from the unlabeled sample is reduced compared to a SITRS protein standard (in which the sequence is known) by an amount that reflects the abundance of the chemically distinct peptide. A non-limiting example of this is depicted in FIG. 2B. Accordingly, by mixing a SITRS protein standard with an unlabeled MAb and subjecting the mixed sample to protein digestion and bottom-up LC-MS, the presence of mutations, modifications and/or site-specifically modified molecules in the unlabeled MAb may be qualitatively identified as well as quantitated.

When comparing two unlabeled samples of MAb to each other, for example unlabeled MAb sample A to unlabeled MAb sample B, certain embodiments will incorporate steps to further minimize variations, such as, but not limited to, pipetting errors and MS detection variations. For example, but not by way of limitation, in order to minimize such variations, the ratios of the unlabeled MAb sample A to the SITRS protein standard may be compared with those of the unlabeled MAb sample B to the SITRS protein standard to arrive at a value is termed the SITRS Value (SV), as shown in Equation 1:

$$SV = \frac{I_A}{I_{SITRS-A}} \Big/ \frac{I_B}{I_{SITRS-B}} \times c = \frac{I_A}{I_B} * \frac{I_{SITRS-B}}{I_{SITRS-A}} \times c$$

In Equation 1, $I_A$ is the peak intensity of the unlabeled MAb sample A, $I_{SITRS-A}$ is the peak intensity of the SITRS protein standard mixed with the unlabeled MAb sample A, $I_B$ is the peak intensity of the unlabeled MAb sample B, and $I_{SITRS-B}$ is the peak intensity of the SITRS protein standard mixed with the unlabeled MAb sample B. The peak intensity ratio of the unlabeled MAb sample A to the unlabeled MAb sample B is converted to a percentage of the expected signal by multiplying by c, a constant that is experimentally determined by obtaining the average of the most similar ratios of $[(I_A/I_{SITRS-A})/(I_B/I_{SITRS-B})]$ according to Equation 2:

$$c = 100\% / \bar{x}\{(I_A/I_{SITRS-A})/(I_B/I_{SITRS-B})\}_{most\ similar}$$

As noted above, common peptides between the two runs will have similar ratios while peptides bearing differences will have different ratios. Thus, in certain embodiments, a single quantitation experiment can involve running at least two protein digests, one containing unlabeled MAb sample A (for example, but not by way of limitation, a well characterized reference antibody) and the SITRS protein standard and the other containing unlabeled MAb sample B (for example, but not by way of limitation, an antibody sample expressed under experimental conditions) and the same SITRS protein standard.

In certain embodiments, the m/z values being compared between two samples, e.g., but not limited to, a first sample of protein of interest and a SITRS protein standard, will correspond to the mass spectra of peptides that cover more than 50% of the protein sequence of the protein of interest. In certain embodiments, the m/z values will correspond to the mass spectra of peptides that cover more than 60% of the protein sequence. In certain embodiments, the m/z values will correspond to the mass spectra of peptides that cover more than 70% of the protein sequence. In certain embodiments, the m/z values will correspond to the mass spectra of peptides that cover more than 80% of the protein sequence. In certain embodiments, the m/z values will correspond to the mass spectra of peptides that cover more than 90% of the protein sequence. In certain embodiments, the m/z values will correspond to the mass spectra of peptides that cover more than 95% of the protein sequence. In certain embodiments, the m/z values will correspond to the mass spectra of peptides that cover the entire protein sequence.

5.3. SITRS Data Analysis

In certain embodiments, the present invention relates to methods and systems for processing the data that is generated when multiple protein samples are analyzed using the SITRS technique and the complex calculations that must be performed to interpret that data. In certain embodiments, the analysis methods and systems disclosed herein generally comprise computer hardware and/or analysis software that facilitates the mathematical calculations necessary to perform such analysis. In certain embodiments, the analysis software is stored as machine readable code in a memory on a computer that is in communication with a mass spectrometry system. In alternative embodiments, the analysis system is applied to the output of a mass spectrometer separately from the mass spectrometry system. In either context, the analysis software can be stored on any suitable memory which is part of or in communication with a computational device. For example, but not by way of limitation, the analysis software, as well as the means for its execution, can be integrated with the mass spectrometry instrument, or housed separately on a computer or any type of suitable electronic storage device. Non-limiting examples of storage devices include hard disks or drives, CD-ROMs, DVDs, and removable storage devices such as USB drives and flash drives. As will be appreciated by those of skill in the art, essentially any hardware, firmware, software, operating system, database platform, networking technique or other conventional computer tool can be configured to operate in connection with the analysis systems, the analysis software, and the methods of the present invention.

In certain embodiments, the term "analysis software" refers to one or more SITRS software applications. In certain embodiments, such software applications can be written and/or implemented in a computer readable and executable language, for example, but not by way of limitation, those used or compatible with the MATLAB environment, which is known in the art. As described in detail below, a SITRS application is, in certain embodiments, written to extract and process the MS data resulting from SITRS analysis. Next, in certain embodiments, the scan times and corresponding m/z intensity values for each scan can be saved by the SITRS application itself, for example, but not by way of limitation, within a MATLAB variable file (*.mat). Then, in certain embodiments, the scans containing the peaks of interest can be analyzed and the intensities corresponding to m/z of monoisotopic peaks for unlabeled and labeled peptides can be separately summed up together by the application. In certain embodiments, only the intensities from scans where all monoisotopic peaks that are monitored are detected can be summed up together. Such criterion can narrow the peak width and removes any scans suffering from poor resolution and/or spikes that could affect the results. In certain embodiments, the output of the SITRS application can be given in the form of a file, such as, but not limited to, a Microsoft Excel file, containing the raw, the processed (e.g., normalized), or a combination of raw and processed data, including, in certain embodiments, bar graphs for visualization of differences, if any, between the samples at the peptide and/or amino acid level.

In certain embodiments, the present invention relates to a system for processing the data that is generated when multiple protein samples are analyzed using the SITRS technique and performing the calculations necessary to interpret that data. In certain embodiments, such systems comprise a controller, e.g., which can be implemented using a general purpose computer or other computing device, that controls various components of the system and allows for user-input of data; a spectrum data processor capable of identifying individual m/z values and comparing the relative intensities of the individual m/z values; and an output unit that outputs the result of the processing performed by the spectrum data processor. In certain embodiments, the above-described system will further comprise a mass spectrometer in functional communication with the system. In certain embodiments, the above-described system will further comprise a liquid chromatography apparatus in functional communication with the system. In certain embodiments, the above-described systems are configured such that the functions performed by the controller, the spectrum data processor, and the output unit are accomplished by executing one or more software applications installed on a general purpose computer that is in functional communication with the system. However, numerous other implementations within the spirit and scope of the invention, utilizing various different software and hardware embodiments, would be apparent to those of ordinary skill in the art.

5.3.1. Extraction of MS Instrument Data

In certain embodiments, the first step of SITRS data analysis involves the extraction of the MS instrument data containing the MS spectra to be analyzed. In certain embodiments, a SITRS application is employed to accomplish this data extraction. In alternative embodiments an independent application is employed to accomplish this data extraction and the extracted data is subsequently processed by the SITRS application. The MS instrument data can take a variety of forms, largely depending on the type of MS equipment employed. In certain embodiments, the instrument data is converted to a common file format, such as, but not limited to, an mzXML file format, i.e., a known XML (extensible markup language)-based common file formats for proteomic and mass spectrometric data. For example, but not by way of limitation, the SITRS application can facilitate the conversion of Agilent.d MS spectra files generated using Agilent MS equipment into mzXML format. In certain embodiments, the Agilent files are converted to the common mzXML MS data format using a third-party application "trapper" (v.4.3.1; built Sep. 9, 2009 12:29:13; available from Seattle Proteome Center (SPC) Alternative applications are available for such extraction and conversion, and, in certain embodiments, custom-written applications can be employed.

5.3.2. Compilation of User-Input Information

In certain embodiments, SITRS data analysis involves the input of user information. While certain embodiments of SITRS data analysis do not require the input of user information, other embodiments can employ one or more of the following types of user-input information:

a) a list of m/z values corresponding to the monoisotopic peak or peaks for each unlabeled and labeled peptide monitored in SITRS analysis.
 b) A list of retention time values corresponding to each peptide monitored in SITRS analysis.
 c) A error tolerance/deviation for m/z and retention time values described in a) and b).
 d) A minimum and/or maximum intensity that is allowed for the m/z to be used in the SITRS analysis.
 e) One or more m/z value(s) with corresponding retention time(s) for normalization of the retention times listed in b). A greater error tolerance/deviation for the retention time value can be allowed for the m/z of the peak or peaks used in normalization of the retention times.
 f) The m/z value of the monoisotopic peak, intensity of which would be used to define the crest of the eluted peptide peak (in certain embodiments, this is the m/z corresponding to the monoisotopic peak with the highest intensity for that particular peptide). If the peptide amino acid sequence is supplied, the intensity profile for each monoisotopic peak for a given peptide can be automatically calculated, and the m/z value of the most intense monoisotopic peak can be automatically chosen.
 g) The names that are to be associated with the MS data input and the results output files.

In embodiments where user-input is employed, the user-input information can be input directly into the SITRS application, e.g., via a keyboard and mouse interaction with graphical user interface ("GUI") elements displayed on a screen. In alternative embodiments, the user-input information is first input into a file format that is compatible with the SITRS application to facilitate use of the information. In certain of such embodiments, the user-input data is entered into a spreadsheet, such as, but not limited to, a Microsoft Excel spreadsheet. In circumstances where no user-input data is entered for one or more of a) through g), outlined above in section 3.5.2. ("Compilation of User Input Information"), the data is either automatically generated, e.g., the creation of complete list of m/z values as described below, or is already included in the system as stored default values, or the SITRS analysis proceeds without reference to that data, e.g., without eliminating m/z data based on minimum or maximum intensities.

5.3.3. Normalization of Peak Retention Times in LC-MS Runs

In certain embodiments, a normalization/adjustment of retention times referenced as b) in section 3.5.2. ("Compilation of User-Input Information"), above, is performed with the information supplied in e) of that paragraph. For example, but not by way of limitation, the SITRS application can incorporate a software script for normalization. In certain embodiments, such normalization software script will accomplish the normalization by performing calculations according to Equation 3:

$$\frac{B}{A} \times 100\% = \frac{\frac{I_B}{I_{SITRS-B}}}{\frac{I_A}{I_{SITRS-A}} \times c} \times 100\%$$

In this equation, A and B are the relative amounts of a peptide in sample A and the same peptide in sample B, respectively.

$I_A$, $I_B$, $I_{SITRS-A}$ and $I_{SITRS-B}$ are intensities of m/z ion peaks for the same peptide in samples A, B, SITRS standard mixed with sample A and SITRS standard mixed with sample B, respectively. Constant c is a normalization factor that accounts for possible unequal addition of SITRS standard to sample A versus sample B. Specifically, c is a trimmed mean of B/A values that exclude outliers outside of the 95% confidence interval of B/A values for a set of peptides that typically do not undergo post-translational modifications. Thus, multiplication of $I_A/I_{SITRS-A}$ by c produces a result equal to the ratio of $I_B/I_{SITRS-B}$ for the majority of the peptides quantitated. In certain embodiments, the normalization software script is written in the MATLAB environment (version 7.11.0.584 [R2010b]; win32; MathWorks).

5.3.4. Preparation of a Full List of m/z Values

In certain embodiments, such as those where a user has not supplied a complete list of m/z values, a complete list of m/z values can be automatically generated by the SITRS application, or other software, if user supplies the following information: peptide sequence (or m/z of C12 peak, or MW and the charge state), the identity of labeled amino acids (or the number of labeled amino acids present in sequence of the monitored peptide), the MW difference between the unlabeled and labeled amino acid (ex: difference between unlabeled Lys and [6×C13]Lys is ~6.0201 Da), and the corresponding numbers for the monoisotopic peaks that would be monitored (ex: C12, 1×C13, 2×C13, etc).

In certain embodiments, the spectrum data processor uses user-defined m/z monoisotopic peaks. In certain embodiments, the spectrum data processor automatically calculates the m/z values for the monoisotopic peaks that should be used for calculating intensity ratios.

5.3.5. Narrowing of Retention Time Range

In certain embodiments, the retention time range for each peptide can be further narrowed during SITRS data analysis. In certain embodiments, the result of such narrowing is that the SITRS application only uses the intensities of m/z values specified in a) of section 3.5.2. ("Compilation of User-Input Information"), above, if they are present in MS spectra collected within the narrowed range. To narrow the retention time range, the following steps can be performed. First, the spectra obtained during the retention times listed in b) of section 3.5.2 with the range defined by error tolerance/deviation in c) of section 3.5.2. are analyzed. Such analysis can be performed by the SITRS application itself, or by one or more alternative applications. The retention time at which the MS spectrum contains the highest intensity for the m/z corresponding to the monoisotopic peak defined in f) of section 3.5.2. would typically correspond to the crest of the peak. However, if any other intensities corresponding to the m/z values of the monoisotopic peaks derived from the given peptide are higher than the intensity of the monoisotopic peak used to define the crest of the peak, then that spectrum does not correspond to the crest of the peak. In certain embodiments, this algorithm for defining the crest of the peak alleviates the problem that may give a false peak crest if two peptides eluting too close to one another and have nearly identical m/z values for their monoisotopic peaks. For example, but not by way of limitation, two peptides, one of which is a deamidated version of the other, would appear in this fashion as the corresponding MW would differ by almost exactly 1 Da). Correction for such false peaks can be performed by the SITRS application or by one or more alternative applications.

An additional correction that can be performed by the SITRS application, or by one or more alternative applications, relates to peak "tailing." Although a typical elution time for a chromatographic peak is twice the elution time of the chromatographic time region where the peak intensity is at least half of the maximum intensity of the given peak, some peaks exhibit more tailing that would offset this approximation. Thus, in certain embodiments, narrowing is accomplished by calculating the elution time of the peak where its intensity is greater than its half maximum intensity and this value is then multiplied by a factor to obtain the elution time window relative to the retention time (crest) of the peak. Two factors are used to define the elution time range: the first is used to define the start of the peak elution relative to the crest of the peak, and the second is used to define the end of the peak elution relative to the crest of the peak. In certain embodiments, only the spectra obtained within the elution range for a given peak are used to calculate the distribution (ratio) of the intensities corresponding to the m/z resulting from MS of unlabeled and labeled peptides of the same amino acid sequence. The foregoing calculations can be facilitated, for example, but not by way of limitation, by implementing the appropriate calculations as part of the SITRS application or by one or more alternative applications.

5.3.6. Analysis of MS Spectra

In certain embodiments, the SITRS application analyzes spectra from a time range defined for each peptide in either b) of section 3.5.2. ("Compilation of User-Input Information"), or after normalization and/or after further narrowing to obtain the intensities for each m/z defined in a) of section 3.5.2.. For example, but not by way of limitation, if all of the specified m/z values (for both unlabeled and labeled peptides) defined in a) of section 3.5.2., with their corresponding intensities, satisfy the criteria for m/z error tolerance defined in c) of section 3.5.2. and intensity range in d) of section 3.5.2. within a single MS scan, then only in that case, the intensities of the specified monoisotopic peaks are used for the SITRS analysis. This further narrows the retention time range and removes any bad spectra from being used in intensity ratio calculations.

In certain embodiments, the SITRS analysis of the m/z data begins by identifying the appropriate m/z intensity values. For example, if more than one m/z peak with its corresponding intensity value is found within the tolerance range for that m/z defined in c) of section 3.5.2. ("Compilation of User-Input Information"), then the highest intensity value is used. Next, within each spectrum, the intensities of m/z peaks corresponding to the unlabeled peptide are summed to create the "light peptide intensity" per spectrum. The same analysis is performed for the labeled peptide to create the "heavy peptide intensity" per spectrum. The foregoing calculations can be facilitated, for example, but not by way of limitation, by implementing the appropriate calculations as part of the SITRS application or by one or more alternative applications.

In certain embodiments, the next step of the SITRS analysis involves identifying all "light peptide intensity" sums from each spectrum corresponding to the elution time window for that particular peak defined in either b) or after normalization and/or after further narrowing, and these intensities are summed to give "light peptide intensity" sum for the entire peak. The same analysis is performed for the labeled peptide to yield the "heavy peptide intensity" sum for the entire peak. The foregoing calculations can be facilitated, for example, but not by way of limitation, by implementing the appropriate calculations as part of the SITRS application or by one or more alternative applications.

Finally, the "light peptide intensity" sum for the entire peak is then divided by the "heavy peptide intensity" sum for the entire peak to give a ratio of the light to heavy peptide intensity. This procedure is performed for each peptide that is monitored using SITRS analysis. The foregoing calculations can be facilitated, for example, but not by way of limitation, by implementing the appropriate calculations as part of the SITRS application or by one or more alternative applications.

5.3.7. Averaging of Multiple LC-MS Runs

In certain embodiments, the SITRS analysis of the present invention will involve multiple rounds of data collection and comparison, for example, but not by way of limitation at least two, at least three, at least four, or at least five rounds of data collection and comparison can be employed. In certain embodiments, the results of such multiple rounds of data collection and comparison are averaged in the SITRS analysis. The foregoing calculations can be facilitated, for example, but not by way of limitation, by implementing the appropriate calculations as part of the SITRS application or by one or more alternative applications

5.3.8. Comparison of Protein Samples

In certain embodiments, it is advantageous to compare multiple protein samples to identify the presence of mutations, modifications, or polypeptide impurities. In certain embodiments such a comparison is accomplished using the SITRS application. For example, but not by way of limitation, a once all of the light/heavy peptide intensity ratios are obtained for each sample (e.g., samples A and B), the averaged light/heavy peptide intensity ratios obtained for sample A are then compared to those of sample B to yield a new ratio of A/B. The foregoing calculations can be facilitated, for example, but not by way of limitation, by implementing the appropriate calculations as part of the SITRS application or by one or more alternative applications In addition, in the context of comparing multiple samples via first comparing one sample (sample A) to a SITRS standard, followed by comparing a second sample (sample B) to the same SITRS standard, and then comparing the resulting ratios to each other, it is noted that the SITRS labeled standard does not have to perfectly match either or both of samples A and B. This is because once the proper comparison of A to the SITRS standard and B to SITRS standard is performed, the SITRS standard is effectively "canceled" when the results of those two comparisons are subsequently compared, i.e. any unknown modifications or intensity differences of peptides in the SITRS standard do not affect the results. An equation that can be employed to describe this type of comparison, including the resulting SITRS Value ("SV"), is Equation 1, above. The foregoing calculations can be facilitated, for example, but not by way of limitation, by implementing the appropriate calculations as part of the SITRS application or by one or more alternative applications In certain embodiments, SITRS analysis includes a data normalization step. For example, but not by way of limitation, normalization in the context of comparing multiple protein samples can be accomplished though the use of Equation 2, above. In certain embodiments, the c value is a common factor that can be used to multiply the new A/B ratio and yield 100 for the majority of the peptides monitored by the SITRS technique. The SITRS application, or one or more alternative applications, can calculate this value by removing the outliers and averaging A/B ratio for each peptide to yield the c value. The foregoing calculations can be facilitated, for example, but not by way of limitation, by implementing the appropriate calculations as part of the SITRS application or by one or more alternative applications In certain embodiments, the A/B ratios, either before or after normalization using the c value (if such normalization is employed), are plotted to visualize any differences between samples A and B. In certain embodiments, the output can be any compatible file type, such as, but not limited to an Excel file. In certain embodiments, the output will include raw, processed (normalized), or a combination of raw and processed (normalized) data. Such raw and processed (normalized) data can take the form of one or more tables and/or one or more graphs. The calculations employed in generating and outputting such data can be facilitated, for example, but not by way of limitation, by implementing the appropriate calculations as part of the SITRS application or by one or more alternative applications.

5.3.9. Qualitative SITRS Analysis for Singlet Identifications

In certain embodiments, it is advantageous to compare an unlabeled protein sample to SITRS standard directly in order to identify the presence of mutations, modifications, or polypeptide impurities. Compound extraction (molecular feature extraction) from LC-MS data is performed and the resulted compound list (containing MW and intensity/volume for each compound) is exported to an Excel file (this operation can be performed using third party software such as Agilent MassHunter or equivalent). The qualitative part of the SITRS software reads the list of exported compounds in order to identify the related compounds corresponding to the labeled and unlabeled versions of the same peptide [i.e. having molecular weights that are different from one another by the whole number multiple of the mass difference between the labeled and unlabeled amino acid(s) that were used in the SITRS experiment]. Related compounds having an intensity (volume) difference above a user-specified threshold and the compounds that completely lack a labeled counterpart are selected and recorded in a separate output file (Excel) that can be used for a targeted MS/MS analysis in the following LC-MS experiments. Identification of these peptides compliments the quantitative aspect of the SITRS analysis described above.

6. EXAMPLES

6.1 Comparison of MAb-1 and MAb-1 Spiked with MAb-2 Using SITRS

In the present example. MAbs were recombinantly expressed in GIA-1 media containing labeled-Arginine (L-Arginine) at 0.837 g/L (monohydrochloride salt; MW 210.66), or 3.97 mM; and labeled-Lysine (L-Lysine) at 1.086 g/L (monohydrochloride salt; MW 182.65), or 5.95 mM.

First, 100 mg/mL stocks of L-Arginine and L-Lysine were prepared. For labeled amino acids, 2.5 mL of HPLC-grade water was added to each vial of amino acid (250 mg). The compounds were dissolved and pooled. The mixture was then sterilized through a 0.2 µm syringe filter. Unlabeled amino acids were prepared in a similar manner. Because the difference in molecular weight between labeled and unlabeled amino acids is small, the same volumes of amino acid stock were employed when supplementing the GIA-1 Arg/Lys dropout media.

GIA-1 Arg/Lys dropout media (374 mL) was supplemented with 3.22 mL of 100 g/L arginine or L-Arginine and 5.00 mL of 100 g/L lysine or L-Lysine. After addition, the media was filter-sterilized once again and a labeled and unlabeled version of an antibody (MAb-1) were produced using standard methods known in the art, then stored at −80° C. The following batches were produced:

Labeled MAb-1—batch A, titer 1.19 g/L;
Unlabeled MAb-1—batch A, titer 1.25 g/L;
Labeled MAb-1—batch B, titer 1.28 g/L; and
Unlabeled MAb-1—batch B, titer 1.25 g/L.

rProtein A Sepharose Fast Flow was used to purify MAb-1 (labeled and unlabeled). The resin was resuspended by vigorous shaking. The Sepharose (1.65 mL, about 1.2 mL of resin) was transferred into a Bio-Rad Poly Prep column that contained 10 mL of 1×PBS (the bottom of the column was capped).

The resin was allowed to settle to the bottom. The cap was then opened and the buffer was allowed to flow through, but was stopped just before reaching the bed of the resin.

The resin was equilibrated by passing 20 mL of 1×PBS (about 2 column volumes) at a rate of ~3-5 mL/min. Sample (10 mL~10 mg) was applied onto the column at a rate of ~1 mL/min. 10 mg of labeled MAb-1, batch B, and 10 mg of unlabeled MAb-1, batch B, were processed.

The column was then rinsed with 4×10 mL (about 2 column volumes) of 1×PBS at a rate ~3-5 mL/min and the sample was eluted with 5 mL of 0.1 M acetic acid, 0.15M sodium chloride, pH 3.5 by gravity flow.

The $A_{280}$ of eluted MAb-1 was measured on a 10× dilution of the eluate. Specifically, 20 μL of protein was diluted to 200 μL by addition of 180 μL of 10 mM Tris, pH 8.0 buffer. The extinction coefficient of MAb-1 was 1.43 mL/mg*AU.

Eluted MAb-1 (5 mL) was neutralized with 0.5 mL of 1M Tris, pH 8.5, which brought the pH into 7-8 range and raised the final concentration of Tris in the sample to 100 mM.

The purified MAb-1 was further concentrated using a Microcon YM-30 centrifugal filter. Because the capacity of the filter was 0.5 mL, the concentration was performed in two stages. The samples were centrifuged for 10 to 15 minutes at 10,000 g to reduce the volume to about 0.25 mL (4× concentration). The final sample concentrations were 6.07 mg/mL for the unlabeled and 5.63 mg/mL for the labeled MAb-1. Samples were then frozen at −80° C.

A Tris buffer was prepared by adding 10 mL of 1M Tris, pH 7.5 buffer to 900 mL of Milli-Q HPLC grade water. The volume was then brought to 1 L using a graduated measuring cylinder. A 0.5 M solution of IAA was prepared by dissolving 0.0478 g of IAA in 0.514 mL of 1M Tris pH=8.0. HCl (5N, 200 μL) was diluted with 800 μL of Milli-Q HPLC-grade water to form 1M HCl. Then, the 1M HCl was diluted to 100 mM by addition of 900 μL of Milli-Q HPLC-grade water to 100 μL of 1M HCl: Next, 10 μL of 100 mM HCl was added to 990 μL of Milli-Q HPLC-grade water to make 1 mM HCl. HCl (1 mM, 100 μL) was added to a 100 μg vial of trypsin.

CHO- and HEK 293-derived MAb-1 samples were diluted with Milli-Q water to 4 mg/mL according to the following procedures:

Milli-Q water (489.8 μL) was added to 10.2 μL of MAb-1, (CHO) at 196.12 mg/mL;
MAb-1, (293 cell line, 87.0 μL at 4.6 mg/mL) was added to 13.04 μL of Milli-Q water; and
Milli-Q water (29.0 μL) was added to 71.0 μL of labeled MAb-1 (5.63 mg/mL, MS internal standard).

The following mixed-SITRS samples were prepared for peptide mapping:

MAb-1. (CHO, 45 μL of 4 mg/mL) was mixed with 45 μL of 4 mg/mL labeled MAb-1; and
MAb-1, (HEK, 45 μL of 4 mg/mL) was mixed with 45 vL of 4 mg/mL labeled MAb-1.

Pure wild-type and 10%-simulated mutant MAb-1 samples were prepared according to the following procedures. Labeled and unlabeled MAb-1 (prepared in GIA-1 media), and unlabeled MAb-2 were diluted with Milli-Q water to 4 mg/mL:

Milli-Q water (75.3 μL) was mixed with 184.7 μL of labeled MAb-1 at 5.63 mg/mL (260 μL total);
Milli-Q water (88.7 μL) was added to 171.3 μL of unlabeled MAb-1 at 6.07 mg/mL (260 μL total);
Milli-Q water (240.4 μL) was added to 19.6 μL of MAb-2 at 53.05 mg/mL (260 μL total); and
A "10%-simulated mutant" was made by mixing 63 μL of 4 mg/ml, of unlabeled MAb-1 and 7 μL of 4 mg/mL MAb-2.

SITRS-spiked samples for peptide mapping were prepared in the following manner:

Unlabeled MAb-1 (62.5 μL of 4 mg/mL) was mixed with 62.5 μL of 4 mg/mL labeled MAb-1; and
10% mutant MAb-1 (62.5 μL of 4 mg/mL unlabeled) was mixed with 62.5 μL of 4 mg/mL labeled MAb-1.

Three samples of 75 μL of 8M Guanidine-HCl, 0.1 M Tris, pH 8.0 were added to the SITRS-spiked sample (25 μL). The samples were incubated at room temperature for 15 minutes.

Reduction was carried out by adding 1 μL of 1M on to each sample, followed by incubation at 37° C. for 30 min.

The samples were alkylated by adding 5 μL of 0.5M 1M, and then incubating at 37° C. for 30 min under a foil cover. After the incubation, excess 1M was inactivated by adding 1.5 μL of 1M on to each sample.

The following conditions and materials were used for SEC-HPLC:

Column: Tosoh TSK-Gel Super SW3000 guard column, 4.6 mm 10×35 mm L, 4 μm particle; cat#18762, lot#K0196;
Mobile Phase A: 10 mM Tris, pH 7.5;
Gradient: isocratic;
Flow rate: 0.25 mL/min, constant;
Autosampler and FC cooler temp: 4° C.;
Column oven temp: ambient;
Wavelength: 280 nm;
Total run time: 4 minutes;
Injection vol: 100 μL; and
Fraction collection: based on time, collecting one fraction between 1 and 2 minutes at room temperature.

A column wash was performed between each run. The column wash method was the same as above, except the flow rate was at 0.4 mL/min for 4 min and no fractions were collected.

100 μL of each sample were injected, with washing steps in between, into the SEC-HPLC. The final volume of the eluted/recovered samples was 250 μL. Because the starting amount of the injected samples was about 100 μg, the final concentration of the recovered samples was about 0.4 mg/mL (assuming 100% sample recovery).

8 μL of 1 mg/mL trypsin (resuspended in 1 mM HCl) were added to 200 μL (80 μg) of SEC-HPLC purified sample (1:10 enzyme to sample ratio by weight). Then, the mixture was incubated for 30 minutes at 37° C. After incubation, the reaction was quenched by addition of 2 μL of 1M HCl. 10 μL (or about 4 μg) of sample were loaded onto HPLC for MS analysis.

The following conditions and materials were used for LC-MS:

Column: Higgins Analytical Proto 200 C18 RP column (5 μm, 200 A, 1×250 mm);
Mobile Phase A: 0.02% TFA, 0.08% formic acid in water;
Mobile Phase B: 0.02% TFA, 0.08% formic acid in ACN;
Gradient: binary;
Flow rate: 50 μL/min, constant;
Initial conditions: 2% B;
Autosampler cooler temp: 4° C.;
Column oven temp: 60° C.;
Total run time: 120 min;
Injection vol: 10 μL (4 μg of sample); and
Binary gradient program:

| Time (min) | % B |
|---|---|
| 0 | 2 |
| 10 | 2 |
| 90 | 55 |
| 100 | 98 |
| 110 | 98 |
| 112 | 2 |
| 120 | 2 |

The method diverted the eluent into waste for the first four minutes, and then directed it into the mass spectrometer. No MS information was collected during the run to improve quantitation of the results.

The following samples were analyzed in sequence:
50/50 mix of labeled MAb-1/unlabeled 10% mutant MAb-1;
50/50 mix of labeled MAb-1/unlabeled 10% mutant MAb-1;
50/50 mix of labeled MAb-1/unlabeled 10% mutant MAb-1;
50/50 mix of labeled MAb-1/unlabeled wt MAb-1;
50/50 mix of labeled MAb-1/unlabeled wt MAb-1; and
50/50 mix of labeled MAb-1/unlabeled wt MAb-1.

Additionally, the following samples were analyzed in sequence:
50/50 mix of labeled MAb-1/unlabeled MAb-1 from CHO;
50/50 mix of labeled MAb-1/unlabeled MAb-1 from HEK;
50/50 mix of labeled MAb-1/unlabeled MAb-1 from CHO;
50/50 mix of labeled MAb-1/unlabeled MAb-1 from HEK;
50/50 mix of labeled MAb-1/unlabeled MAb-1 from CHO; and
50/50 mix of labeled MAb-1/unlabeled MAb-1 from HEK.

As can be seen from the above examples, using SITRS enables mining of MS-generated data for both qualitative and quantitative comparison of protein samples.

The above examples utilized the previously-discussed gel filtration by SEC-HPLC denaturation procedure. As can be seen in FIG. 3, the eluent was monitored with an end result of a purified and less-dilute antibody sample than available in traditional desalting techniques. In addition, the nearly-complete elimination of guanidine salt from the sample permitted the significant shortening of the trypsin digestion time and, therefore, minimized sample-handling artifacts that could be introduced by prolonged incubation.

Figure 4:
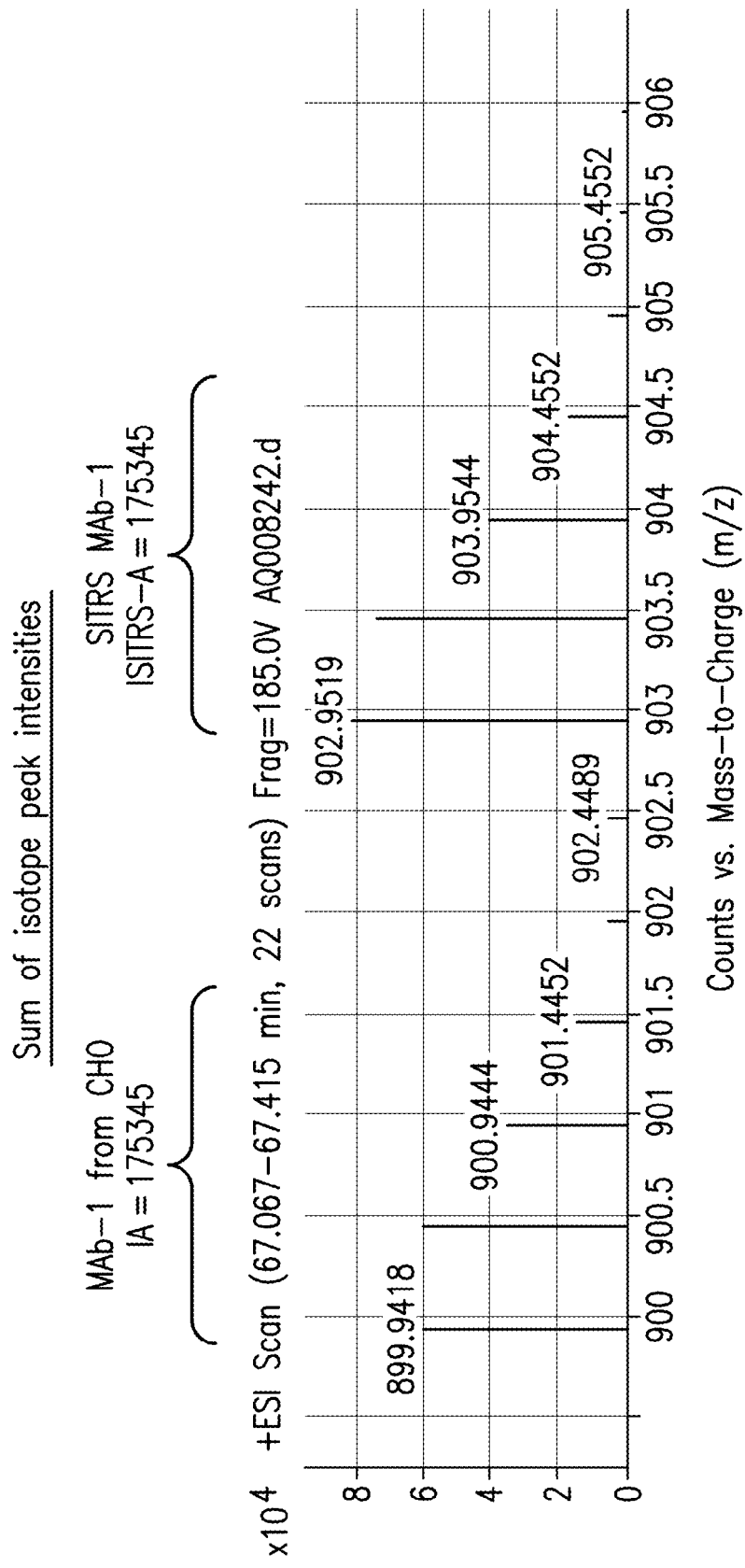

Digesting a MAb-1 sample after removal of the guanidine and other contaminants in the presence of an equimolar amount of the SITRS standard resulted in mass spectra of peptides characterized by the expected doublets of appropriate signal intensity. FIG. 4 shows a typical mass spectrum of a peak from a tryptic digest of MAb-1, mixed in an equimolar ratio with the SITRS standard. In addition to the expected m/z peak of 899.9418 ([M+2H]+2 peak corresponding to peptide 127-142 of LC), plus monoisotopic peaks from naturally-occurring $^{13}$C-containing peptides, for the unlabeled peptide, there is an additional set of peaks from the SITRS. The expected ratio of the peak intensities of MAb-1:SITRS is 1. The experimental ratio measurement, made by summing the peak heights of all relevant peaks, is 0.811. Calculation of the ratio for 11 peaks from the light chain in the chromatogram results in an average ratio of 0.823±0.014. This number was consistent across all 42 peptides examined, with a standard deviation of 2%. This result supports the assumption that ionization of the labeled and unlabeled peptides is identical. Without being bound by theory, it is believed the deviation from the expected ratio of 1 is due to a systematic factor such as pipetting errors in the initial protein concentration.

6.2. Comparison of MAb-1 from CHO and HEK Cells Using SITRS

Figure 5A:
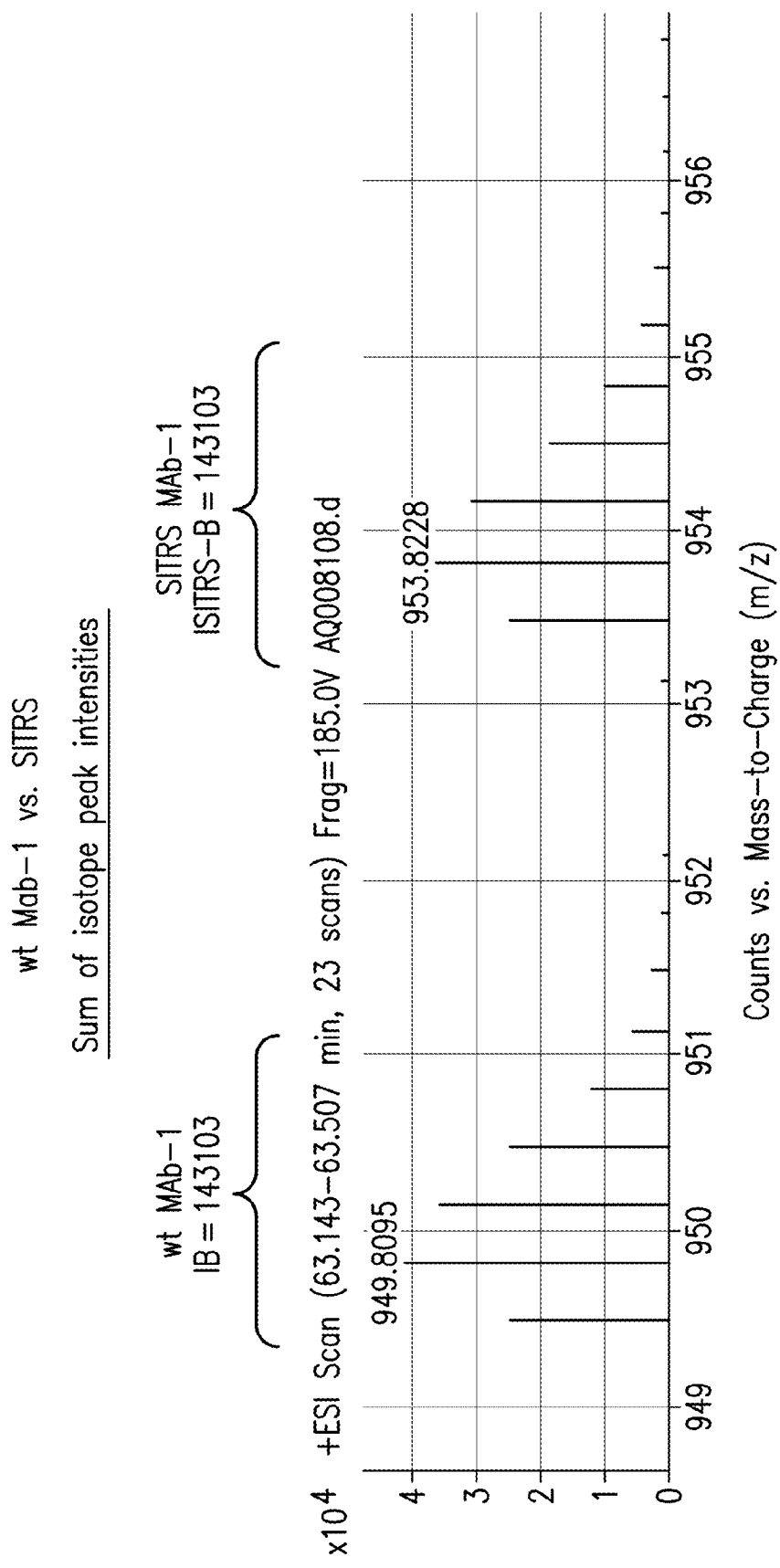
Figure 5B:
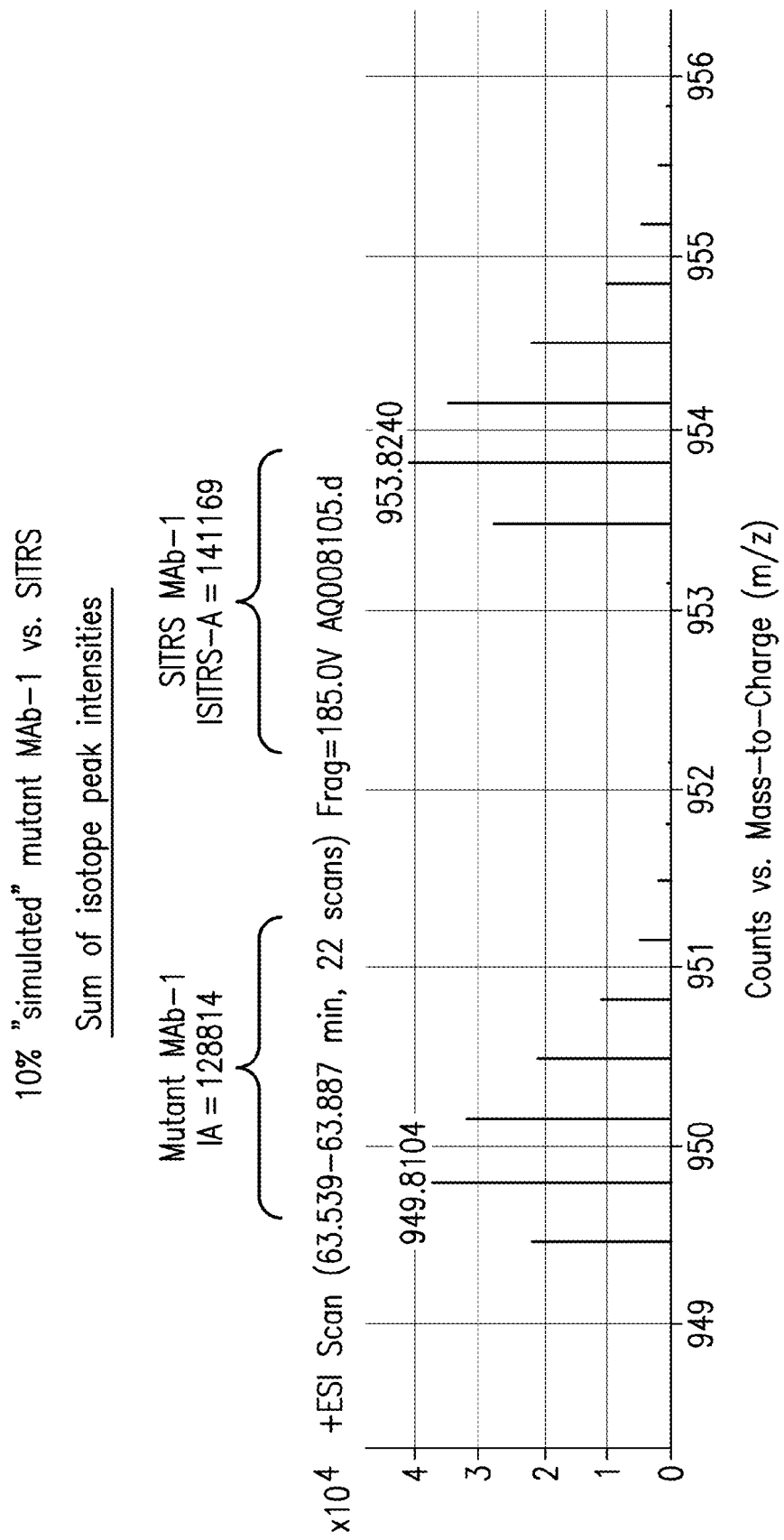
Figure 6:
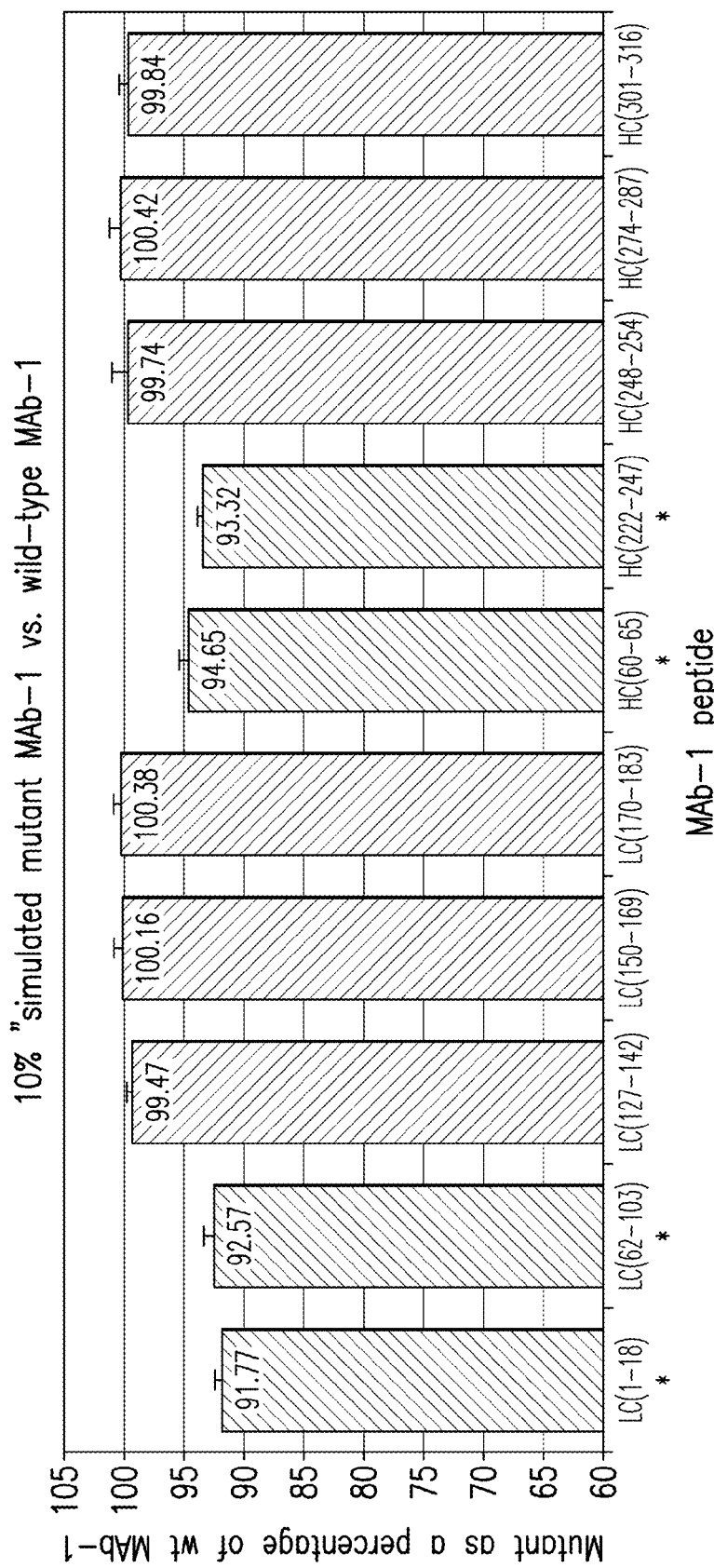

The presence of m/z peaks from the SITRS standard enables the quantitation of differences in abundance of a given peptide. This example details quantitation of the level of contamination of a sample of MAb-1 by an antibody other than MAb-1. Specifically, a sample of MAb-1 was spiked with MAb-2 to a final concentration of 10% (90% MAb-1+10% MAb-2). This experiment was intended to simulate a sample that contains 10% of an antibody that bears point mutations, a plausible scenario that may arise by accident or through natural biological processes during manufacturing. Being highly homologous, most peptides generated by tryptic digest are common between the two antibodies and were expected to yield a SITRS value (SV) of 100%. Six such peptides were selected for study. There are a few however, which differ by 1 or more amino acids and were expected to have an SV of 90%. FIG. 5 shows two mass spectra from one such "mutant" peptide. The first spectrum is from the unlabeled antibody standard (no contaminating MAb-2 was added) mixed with SITRS (FIG. 5A) and the second spectrum is from the unlabeled, contaminated sample containing 10% MAb-2 mixed with SITRS (FIG. 5B). The observed SV for this mutation-bearing peptide is approximately 93.3%. More broadly, peptides that are different between MAb-1 and MAb-2 have an average SV of 93%, while the common peptides had the expected value of approximately 100% (FIG. 6). The discrepancy was unaccounted for but, without being bound by theory, may be explained by errors in pipetting or concentration. Thus, the SITRS method was successfully used to identify point mutations in molecules at a level of 10% of total protein.

Figure 7:
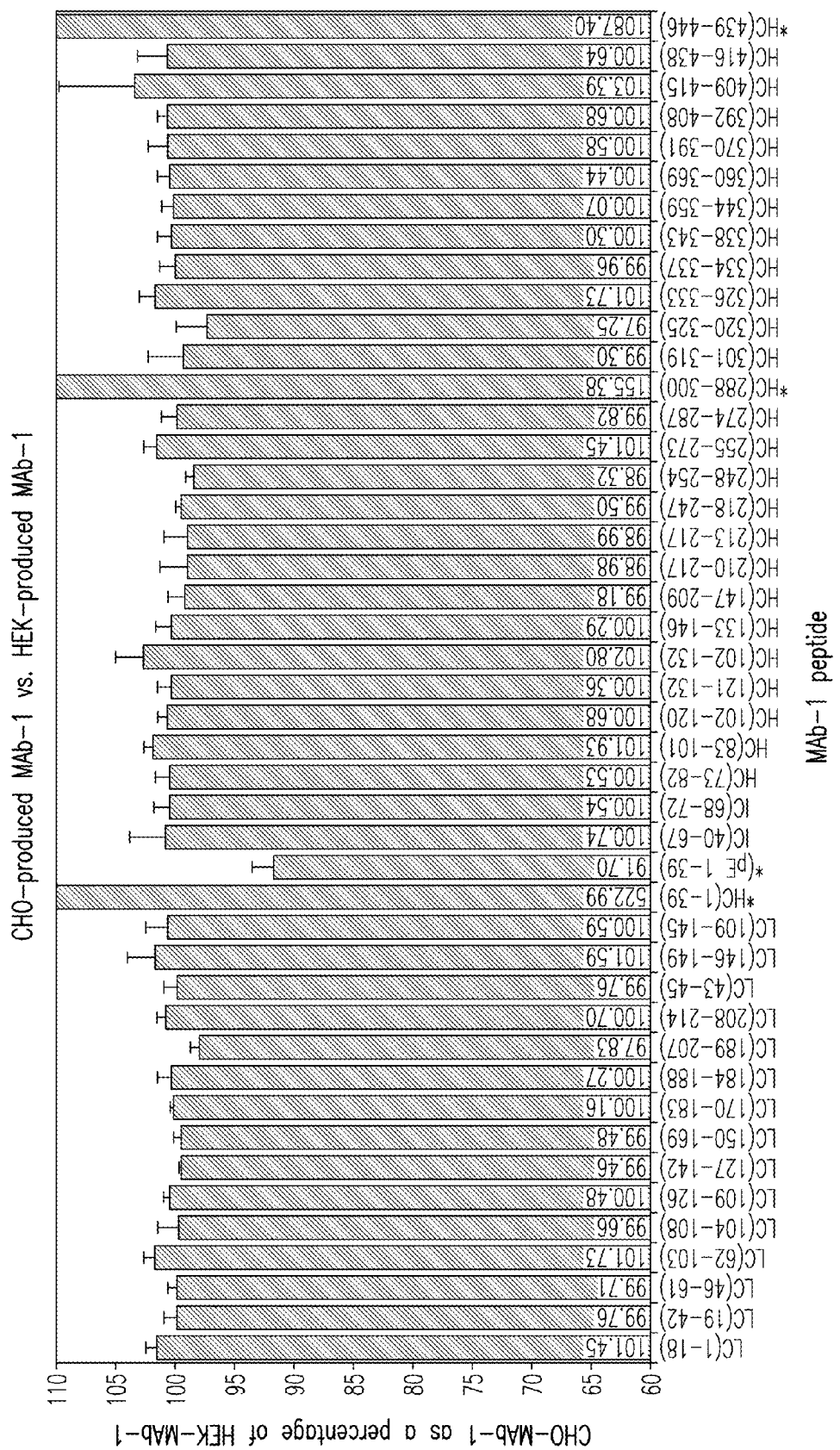
FIG. 7 is a comparison of SV from MAb-1 peptides derived from Human Embryonic Kidney 293 cells versus Chinese Hamster Ovary cells in accordance with the present analysis.

FIG. 7 and Table 1 show data from a SITRS experiment using material derived from CHO and from 293 cell lines. 293-derived material has 20% less agalactosylated glycoform (NGA2F) glycosylation in the heavy chain than MAb-1 from CHO. Furthermore, the two batches also differ in the amount of C-terminal lysine on the heavy chain, as well as the amount of N-terminal pyroglutamate formation. Peptides bearing these modifications were readily apparent in the SITRS experiment by their dramatic differences in SV (columns marked with an asterisk in FIG. 7). Furthermore, peptides that were predicted to show no difference in levels of abundance (that is, all the common peptides) were similar in their SITRS ratios, with an average standard deviation for unmodified peptides of 1.4% (ranging from 0.22 to 6.31%).

TABLE 1

A Comparison of Modifications Identified by SITRS versus Standard Methods

| Measured Characteristic | SITRS Method | Standard Method |
|---|---|---|
| (% NGA2F$_{CHO}$)/(% NGA2F$_{293}$) | 1.554 | 61.67/39.35 = 1.567 |
| (% pyroglutamate$_{CHO}$)/(% pyroglutamate$_{293}$) | 0.917 | 81.33/95.59 = 0.851 |
| (% C-terminal lysine)$_{CHO}$/(% C-terminal lysine)$_{293}$ | 10.9 | 13.86/1.54 = 9.00 |

As illustrated in Table 1, the SITRS technique can be used to quantitate differences among batches of a given protein. Uniform incorporation of lysine-6 and arginine-6 into MAb-1 was achieved by producing MAb-1 in a cell culture using lysine- and arginine-deficient chemically-defined media supplemented with the labeled amino acids. A comparison of unlabeled MAb-1 with its SITRS standard counterpart by mass spectrometry demonstrated that the data generated by this method is consistent, with a standard deviation of 2%. Application of the method to MAb-1 produced by a HEK 293 cell line correctly identified the peptides bearing differences in levels of modification, such as N-terminal pyroglutamate, C-terminal lysines, and NGA2F levels. Furthermore, the method was successfully used to identify the peptides bearing a single amino acid difference between MAb-2 and MAb-1 at a level of approximately 10%.

6.3. Comparison of MAb-1 and MAb-1 Spiked with Mutant MAb-1 Using SITRS

In another experiment, a sample of MAb-1 was spiked with mutant MAb-1 containing 2 point mutations (MAb-2). Specifically, one mutation resides in peptide HC (218-247) and the other in HC (344-349). The mutant was added to a final concentration ranging from 20% (90% MAb-1+20% mutant MAb-1, FIG. 11) to 2.5% (97.5% MAb-1, 2.5% mutant MAb-1, FIG. 12). FIGS. 11 and 12 show that peptides which are common to both wild type and mutant MAb-1 have the expected value of approximately 100%. The two mutant peptides have the expected value of approximately 80% (FIG. 11) or 97.5% (FIG. 12). Glycopeptide HC (G0F-288-300) and HC (439-446) are also different between the two samples. This was expected as it was known that the glycopeptides and the C-terminal peptide in the two samples differed in their oligosaccharide composition and C-terminal lysine content, respectively. FIG. 13 shows the percent difference in levels of wild type peptides HC(218-247), HC(344-349) and HC(G0F-288-300) for various amounts of mutant MAb-1 spiked into wild-type MAb as measured by SITRS. The method responds linearly to the amount of mutant present and has a method detection limit of 2.4%.

6.4. Comparison of Manufacturing Processes Using SITRS

To further test the ability of the SITRS method to discriminate between samples, a change in manufacturing process was simulated by producing the mAb-1 in a HEK cell line. The SITRS analysis of the CHO- and HEK-derived mAb is shown in FIG. 14A and FIG. 14B, respectively. Three peptides immediately stand out from the analysis. First, HC(1-39), which bears an N-terminal pyroglutamate residue, is more abundant in the HEK sample by 7.1%. Consistent with this result, HC(1-39) bearing an N-terminal uncyclized glutamine residue is more abundant by 74% in the CHO-derived mAb. The second site of differentiation is in the C-terminal heavy chain peptide HC(439-446). This was due to minor differences in proteolytic processing of Lys446, a common post-translational event in mAbs. The third significant difference is in the relative abundance of various glycopeptides.

To verify these differences, the MAbs were deglycosylated with PNGase F and the oligosaccharides were quantitated by HPLC after labeling with 2-aminobenzoic acid. The differences in oligosaccharide content as determined by the SITRS method versus enzymatic digestion are summarized in FIG. 15. Also included in FIG. 16 is a comparison of the levels of N-terminal glutamine conversion and C-terminal lysine removal between the SITRS and label-free MS analyses, as determined by comparison of the intensities of de-charged and de-isotoped peaks via the MassHunter with Bioconfirm software package from Agilent. The results of these two orthogonal methods agree reasonably well, particularly for abundant peptides.

In contrast, two batches of the mAb that were produced by the same manufacturing process in CHO cells were shown to be very similar (FIG. 14A). Less than 3% difference was observed in the amount of N-terminal pyroglutamate in peptide HC(1-39). Similarly, the relative difference in HC(392-445) was only 3.3%. Unlike the batch produced in HEK cells, the two CHO-derived batches also showed comparable glycosylation patterns, a result that is supported by oligosaccharide profiling.

6.5. Monitoring Effect of Environmental Stress Using SITRS

The SITRS method was also successfully used to assess the effect of stress on an antibody. A comparison of peptides derived from a mAb stored for 6 months or 12 months at 4 C in two different buffers seemed to reveal only minor differences between the two samples (FIG. 16). Nevertheless, these minor differences could be quantitated. For example, there was a 6.2% increase in the amount of pyroglutamate in HC(1-39) for the 12 month sample. This result correlated with the loss of HC(1-39) containing N-terminal Gln to 26.8% of that of the 6 month sample. In addition, HC(370-391) decreased by 4.7% This decrease was attributable to increased deamidation, as the deamidated peptide was in greater abundance in the 12 month sample by 231%. The partially digested peptide HC(60-72) (FIG. 16) was observed in the 12 month sample at 911% greater abundance over what was observed in the 6 month sample. This result correlated with a concomitant decrease in HC(60-65), HC(66-72), and HC(68-72).

6.6. Monitoring of Bioconjugation Using SITRS

The SITRS method was also used to monitor bioconjugation experiments of small molecules, drugs or imaging agents to the protein. For example, FIG. 17 shows data from a SITRS experiment in which the metal-chelating imaging agent, CHX-A"-DTPA, was conjugated to lysine residues of the antibody. In principle, there are 92 possible reaction sites in the mAb. The SITRS experiment however, reveals that only 3 sites (peptides marked with arrows) react to an extent of >20%. These reaction sites are distinguished by the fact that the neighboring C-terminal peptide also decreases in its relative abundance by an approximately equal amount as the N-terminal peptide that was modified. This phenomenon is due to the fact that a trypsin cleavage site is lost upon conjugation with CHX-A"-DTPA.

6.7. Comparison of MAb-1 and MAb-1 Spiked with Mutant MAb-1 Using SITRS

FIG. 18 shows another typical mass spectrum of a peak from a tryptic digest of MAb-1, mixed in an equimolar ratio with the SITRS standard. In addition to the expected m/z of 1070.5085 [M+2H]2+ for the peptide 255-273 of heavy chain, plus monoisotopic peaks from naturally-occurring 13C-containing peptides for the unlabeled peptide, there is an additional set of peaks from the SITRS (m/z of 1073.5184 [M+2H]2+ plus monoisotopic peaks from naturally-occurring 13C-containing peptides). The expected ratio of the peak intensities of MAb-1:SITRS is 1 (if samples were mixed 1:1 ratio and no modification of that particular peptide has occurred). The experimental ratio measurement, made by summing the peak heights of all relevant peaks, is 1.07 (FIG. 19). The same ratio was obtained for the same peptide HC(255-273) in 20% mutant-spiked MAb-1. This number was consistent across the majority of the peptides examined. However, when peptide HC(218-247) was examined (m/z of 835.15), the relative abundance of peak intensities corresponding to the unlabeled peptide in the 20% mutant-spiked MAb-1 was decreased relative to the labeled peptide of the same sequence in the SITRS standard (FIG. 20). The apparent change in peak intensity ratio has been quantitated and presented in FIG. 21. The experimental ratio measurement, made by summing the peak heights of all relevant peaks in the wild-type MAb sample (0% mutant), is 1.11, while the same measurement for the 20% mutant-spiked MAb-1 is 0.87. This decrease in the relative intensity of the unlabeled peptide HC(218-247) from the 20% mutant-spiked MAb-1 is consistent with this peptide being modified in the mutant of MAb-1 (MAb-2 sample).

In addition to quantitative data obtained from the SITRS experiment described above, qualitative information about the sample can also be obtained. FIG. 22 shows a set of monoisotopic peaks without a doublet. This peak corresponds to a peptide HC(218-247) from MAb-2 (double-point mutant of MAb-1) that is not present in a wild-type MAb-1.

All patents, patent applications, publications, product descriptions and protocols, cited in this specification are hereby incorporated by reference in their entirety. In case of a conflict in terminology, the present disclosure controls.

While it will be apparent that the invention herein described is well calculated to achieve the benefits and advantages set forth above, the present invention is not to be limited in scope by the specific embodiments described herein. It will be appreciated that the invention is susceptible to modification, variation and change without departing from the spirit thereof.

What is claimed is:

1. A tangible computer readable medium storing instructions capable of being executed on a processor so as to perform a method for detecting the presence of a mutation, modification, or impurity in a sample of a protein of interest, the method comprising:

measuring, using a mass spectrometer, a mass spectrum of intensity as a function of mass to charge ratio (m/z) of peptides obtained from a digested mixture of:
- a first reference sample consisting essentially of a single protein of interest having a known amino acid sequence, wherein at least one amino acid in the protein of interest is replaced with an isotopically labeled amino acid comprising at least one heavy isotope; and
- a second sample of the single protein of interest comprising an unlabeled amino acid corresponding to the isotopically labeled variant in the reference protein;
- wherein substantially all peptides of the reference sample in the digest comprise at least one isotopically labeled amino acid; and
- wherein the first labeled reference sample of the protein of interest and the second unlabeled sample of the protein of interest are mixed in a 1:1 ratio prior to digestion;
- wherein the m/z values corresponding to the mass spectrum of peptides cover more than 80% of the sequence of the protein of interest;
- determining m/z values within the mass spectrum corresponding to each monoisotopic intensity peak;
- identifying those m/z values that correspond to peptides comprising an isotopically labeled amino acid;
- identifying the presence of each doublet within the mass spectrum, wherein each doublet indicates the presence of a peptide with an isotopically labeled amino acid and a corresponding peptide without an isotopically labeled amino acid; and
- determining an intensity ratio for each identified doublet in the mass spectrum from the ratio of the peak intensity of the m/z value for the unlabeled peptide in the second unlabeled sample of the protein of interest to the m/z value for the corresponding peptide in the first labeled reference sample of the protein of interest; and
- detecting the presence of a mutation, modification, or impurity in the second unlabeled sample of the protein of interest when the intensity ratio for any doublet is less than one.

2. A tangible computer readable medium storing instructions capable of being executed on a processor so as to perform a method for detecting the presence of a mutation, modification, or impurity in a sample of a protein of interest, the method comprising:

measuring, using a mass spectrometer, a first mass spectrum of intensity as a function of mass to charge ratio (m/z) of peptides obtained from a first digested mixture of:
- a first reference sample consisting essentially of a single protein of interest having a known amino acid sequence, wherein at least one amino acid in the reference protein is replaced with an isotopically labeled amino acid comprising at least one heavy isotope; and
- a second sample of the single unlabeled protein of interest comprising an unlabeled amino acid corresponding to the isotopically labeled variant in the reference protein;
- wherein substantially all peptides of the reference protein in the digest comprise at least one isotopically labeled amino acid; and
- wherein the first labeled reference sample of the protein of interest and the second unlabeled sample of the protein of interest are mixed in a 1:1 ratio prior to digestion;
- wherein the m/z values corresponding to the first mass spectrum of peptides cover more than 80% of the sequence of the protein of interest;
- determining m/z values within the first mass spectrum corresponding to each monoisotopic intensity peak;
- identifying those m/z values within the first mass spectrum that correspond to peptides comprising an isotopically labeled amino acid;
- identifying the presence of each doublet within the first mass spectrum, wherein each doublet indicates the presence of a peptide with an isotopically labeled amino acid and a corresponding peptide without an isotopically labeled amino acid; and
- determining a first intensity ratio for each identified doublet in the first mass spectrum from a ratio of the peak intensity of the m/z values for the unlabeled peptide in the second unlabeled sample of the protein of interest to the peak intensity of the m/z value for the corresponding peptide in the first labeled reference sample of the protein of interest;

measuring, using a mass spectrometer, a second mass spectrum of intensity as a function of mass to charge ratio of peptides obtained from a second digested mixture of:
- the first labeled reference sample of the protein of interest; and
- a third sample of the single protein of interest comprising an unlabeled amino acid corresponding to the isotopically labeled variant in the reference protein;

wherein the first labeled reference sample of the protein of interest and the third unlabeled sample of the protein of interest are mixed in a 1:1 ratio prior to digestion;

wherein the m/z values corresponding to the second mass spectrum of peptides covers more than 80% of the sequence of the protein of interest;

determining m/z values within the second mass spectrum corresponding to each monoisotopic intensity peak;

identifying those m/z values that correspond to peptides comprising an isotopically labeled amino acid;

identifying the presence of each doublet within the second mass spectrum, wherein each doublet indicates the presence of a peptide with an isotopically labeled amino acid and a corresponding peptide without an isotopically labeled amino acid;

determining a second intensity ratio for each identified doublet in the second mass spectrum from a ratio of the peak intensity of the m/z values for the unlabeled peptide in the third unlabeled sample of the protein of interest to the peak intensity of the m/z value for the labeled peptide in the first labeled reference sample of the protein of interest;

determining a reference ratio from a ratio of the first intensity ratio to the second intensity ratio; and detecting the presence of a mutation, modification, or impurity in the first sample of the protein of interest when the reference ratio for any doublet is less than one.

3. The tangible computer readable medium storing instructions capable of being executed on a processor of claim 1 wherein the m/z values corresponding to the mass spectrum of peptides cover more than 90% of the sequence of the protein of interest.

4. The tangible computer readable medium storing instructions capable of being executed on a processor of claim 1 wherein the m/z values corresponding to the mass spectrum of peptides cover more than 95% of the sequence of the protein of interest.

5. The tangible computer readable medium storing instructions capable of being executed on a processor of claim 1 wherein the m/z values corresponding to the mass spectrum of peptides cover the entire sequence of the protein of interest.

6. The tangible computer readable medium storing instructions capable of being executed on a processor of claim 1, further comprising obtaining:

a list of retention times corresponding to the mass spectrum.

7. The tangible computer readable medium storing instructions capable of being executed on a processor of claim 2, further comprising obtaining:

a list of retention times corresponding to the first mass spectrum.

8. The tangible computer readable medium storing instructions capable of being executed on a processor of claim 1, further comprising obtaining an error tolerance/deviation for the m/z and the retention time values.

9. The tangible computer readable medium storing instructions capable of being executed on a processor of claim 1, further comprising obtaining a minimum intensity that is allowed for the m/z values.

10. The tangible computer readable medium storing instructions capable of being executed on a processor of claim 1, further comprising obtaining a maximum intensity that is allowed for the m/z values.

11. The tangible computer readable medium storing instructions capable of being executed on a processor of claim 2 wherein the m/z values corresponding to the first mass spectrum of peptides cover more than 90% of the sequence of the protein of interest.

12. The tangible computer readable medium storing instructions capable of being executed on a processor of claim 2 wherein the m/z values corresponding to the first mass spectrum of peptides cover more than 95% of the sequence of the protein of interest.

13. The tangible computer readable medium storing instructions capable of being executed on a processor of claim 2 wherein the m/z values corresponding to the first mass spectrum of peptides cover the entire sequence of the protein of interest.

14. The tangible computer readable medium storing instructions capable of being executed on a processor of claim 2 wherein the m/z values corresponding to the second mass spectrum of peptides cover more than 90% of the sequence of the protein of interest.

15. The tangible computer readable medium storing instructions capable of being executed on a processor of claim 2 wherein the m/z values corresponding to the second mass spectrum of peptides cover more than 95% of the sequence of the protein of interest.

16. The tangible computer readable medium storing instructions capable of being executed on a processor of claim 2 wherein the m/z values corresponding to the second mass spectrum of peptides cover the entire sequence of the protein of interest.

17. The tangible computer readable medium storing instructions capable of being executed on a processor of claim 2, further comprising obtaining a list of retention times corresponding to the second mass spectrum.

18. The tangible computer readable medium storing instructions capable of being executed on a processor of claim 2, further comprising obtaining an error tolerance/deviation for the m/z and the retention time values for the first mass spectrum.

19. The tangible computer readable medium storing instructions capable of being executed on a processor of claim 2, further comprising obtaining an error tolerance/deviation for the m/z and the retention time values for the second mass spectrum.

20. The tangible computer readable medium storing instructions capable of being executed on a processor of claim 2, further comprising obtaining a minimum intensity that is allowed for the m/z values of the first mass spectrum.

21. The tangible computer readable medium storing instructions capable of being executed on a processor of claim 2, further comprising obtaining a minimum intensity that is allowed for the m/z values of the second mass spectrum.

22. The tangible computer readable medium storing instructions capable of being executed on a processor of claim 2, further comprising obtaining a maximum intensity that is allowed for the m/z values of the first mass spectrum.

23. The tangible computer readable medium storing instructions capable of being executed on a processor of claim 2, further comprising obtaining a maximum intensity that is allowed for the m/z values of the second mass spectrum.

* * * * *